United States Patent
Shao et al.

(10) Patent No.: US 9,586,888 B2
(45) Date of Patent: *Mar. 7, 2017

(54) PHENYL SUBSTITUTED CYCLOALKYLAMINES AS MONOAMINE REUPTAKE INHIBITORS

(71) Applicant: Sunovion Pharmaceuticals Inc., Marlborough, MA (US)

(72) Inventors: Liming Shao, Lincoln, MA (US); Fengjiang Wang, Northborough, MA (US); Scott Christopher Malcolm, Southborough, MA (US); Michael Charles Hewitt, Somerville, MA (US); Jianguo Ma, Natick, MA (US); Seth Ribe, Worcester, MA (US); Mark A. Varney, Laguna Nigel, CA (US); Una Campbell, Marlborough, MA (US); Sharon Rae Engel, Hudson, MA (US); Larry Wendell Hardy, Sturbridge, MA (US); Patrick Koch, Marlborough, MA (US); Rudy Schreiber, Watertown, MA (US); Kerry L. Spear, Concord, MA (US)

(73) Assignee: SUNOVION PHARMACEUTICALS INC., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/149,492

(22) Filed: Jan. 7, 2014

(65) Prior Publication Data

US 2014/0121282 A1    May 1, 2014

Related U.S. Application Data

(63) Continuation of application No. 12/131,845, filed on Jun. 2, 2008, now Pat. No. 8,669,291.

(60) Provisional application No. 60/941,242, filed on May 31, 2007.

(51) Int. Cl.
  *C07C 215/42*  (2006.01)
  *C07C 217/52*  (2006.01)
  *C07C 217/76*  (2006.01)
  *A61K 31/135*  (2006.01)

(52) U.S. Cl.
  CPC .......... *C07C 215/42* (2013.01); *A61K 31/135* (2013.01); *C07C 217/52* (2013.01); *C07C 217/76* (2013.01); *C07B 2200/07* (2013.01); *C07C 2101/14* (2013.01)

(58) Field of Classification Search
  None
  See application file for complete search history.

(56) References Cited

U.S. PATENT DOCUMENTS

| | | |
|---|---|---|
| 3,496,181 A | 2/1970 | Skaletzky et al. |
| 3,634,454 A | 1/1972 | Lewis et al. |
| 3,974,157 A | 8/1976 | Shetty et al. |
| 4,540,690 A | 9/1985 | Szmuszkovicz |
| 4,587,258 A | 5/1986 | Gold et al. |
| 4,738,709 A | 4/1988 | Nielsen |
| 4,751,231 A | 6/1988 | Halczenko et al. |
| 4,981,870 A | 1/1991 | Koe |
| 5,373,018 A | 12/1994 | Cugola et al. |
| 5,374,649 A | 12/1994 | Cugola et al. |
| 5,523,278 A | 6/1996 | Wepplo |
| 5,550,255 A | 8/1996 | Urbach et al. |
| 5,578,627 A | 11/1996 | Takeda et al. |
| 5,620,997 A | 4/1997 | Bolton et al. |
| 5,668,162 A | 9/1997 | Domagala et al. |
| 5,686,461 A | 11/1997 | Cugola et al. |
| 5,859,042 A | 1/1999 | Lee et al. |
| 5,962,496 A | 10/1999 | Cugola et al. |
| 5,965,591 A | 10/1999 | Kojima et al. |
| 6,069,176 A | 5/2000 | Tsuchiya et al. |
| 6,096,771 A | 8/2000 | Kojima et al. |
| 6,100,289 A | 8/2000 | Cugola et al. |
| 6,191,138 B1 | 2/2001 | Gutterer |
| 6,331,636 B1 | 12/2001 | Romero et al. |
| 6,372,919 B1 | 4/2002 | Lippa et al. |
| 6,399,601 B1 | 6/2002 | Du Bois |
| 6,410,790 B1 | 6/2002 | Sundermann et al. |
| 6,479,527 B1 | 11/2002 | Barker et al. |
| 6,576,653 B2 | 6/2003 | Du Bois |

(Continued)

FOREIGN PATENT DOCUMENTS

| | | |
|---|---|---|
| BE | 616646 A | 5/1962 |
| CA | 2410077 A1 | 10/1946 |

(Continued)

OTHER PUBLICATIONS

[Database Registry Chemical Abstracts Service, Columbus, Ohio, Accession No. RN 854711-05-0, Entered STN: Jul. 12, 2005.].*
[Ito, Nobuyuki. Cancer Science 94(1), (2003) 3-8.].*
Database Registry Chemical Abstracts Service, Columbus, Ohio, Accession No. RN 284025-73-6, Entered STN: Aug. 8, 2000.*
Abarbri, M. et al., Les Beta-Cétonitriles Groupes Protecteurs de la Fonction Amine: Préparation d'amino-alcools, Helvetica Chimica Acta, 78(1):109-121 (1995).
Aboul-Enein, H.Y. et al., Synthesis and Antiemetic Profile of N-[1-[(diethylamino)methyl]cyclohexy]amides, Scientia Pharmaceutica, 58(3):273-280 (1990).
Alvaro, M. et al., Preparation and Photolysis of Diaryl Esters of Acetylenedicarboxylic Acid, Tetrahedron, 48(16):3437-3444 (1992).

(Continued)

Primary Examiner — Samantha Shterengarts

(57) ABSTRACT

Phenyl-substituted cyclohexylamine derivatives and method for their synthesis and characterization are disclosed. Use of these compounds to treat/prevent neurological disorders as well as methods for their synthesis are set forth herein. Exemplary compounds of the invention inhibit reuptake of endogenous monoamines, such as dopamine, serotonin and norepinephrine (e.g., from the synaptic cleft) and modulate one or more monoamine transporter. Pharmaceutical formulations incorporating compounds of the invention are also provided.

27 Claims, 10 Drawing Sheets

(56) References Cited

U.S. PATENT DOCUMENTS

| | | | |
|---|---|---|---|
| 6,589,949 B1 | 7/2003 | Moriwaki et al. | |
| 6,603,000 B2 | 8/2003 | Yee et al. | |
| 6,828,460 B2 | 12/2004 | Browning et al. | |
| 6,995,144 B2 | 2/2006 | Ozaki et al. | |
| 7,022,739 B2 * | 4/2006 | Buschmann et al. | 514/646 |
| 7,166,725 B2 | 1/2007 | Fang et al. | |
| 7,226,938 B2 | 6/2007 | Cai et al. | |
| 7,273,952 B2 | 9/2007 | Sundermann et al. | |
| 7,488,747 B2 | 2/2009 | Fang et al. | |
| 7,579,370 B2 | 8/2009 | Heffernan et al. | |
| 7,615,572 B2 | 11/2009 | Fang et al. | |
| 8,669,291 B2 * | 3/2014 | Shao et al. | 514/650 |
| 2002/0010198 A1 | 1/2002 | Jerussi et al. | |
| 2002/0085976 A1 | 7/2002 | Elomari | |
| 2002/0123490 A1 | 9/2002 | Howard | |
| 2002/0183369 A1 | 12/2002 | Du Bois | |
| 2003/0087803 A1 | 5/2003 | Yatvin et al. | |
| 2003/0171440 A1 | 9/2003 | Senanayake et al. | |
| 2003/0195361 A1 | 10/2003 | Du Bois | |
| 2003/0215523 A1 | 11/2003 | Ozawa et al. | |
| 2003/0232891 A1 | 12/2003 | Sundermann et al. | |
| 2004/0048878 A1 | 3/2004 | Cai et al. | |
| 2004/0063768 A1 | 4/2004 | Denhart et al. | |
| 2004/0092605 A1 | 5/2004 | Jerussi et al. | |
| 2004/0106681 A1 | 6/2004 | Rao et al. | |
| 2004/0171615 A1 | 9/2004 | Sundermann et al. | |
| 2004/0220229 A1 | 11/2004 | Bussolotti et al. | |
| 2005/0020645 A1 | 1/2005 | Ohta et al. | |
| 2005/0038034 A1 | 2/2005 | Uragg et al. | |
| 2005/0089935 A1 | 4/2005 | Cai et al. | |
| 2005/0143434 A1 | 6/2005 | Fang et al. | |
| 2005/0143443 A1 | 6/2005 | Fang et al. | |
| 2005/0182131 A1 | 8/2005 | Friderichs et al. | |
| 2006/0019944 A1 | 1/2006 | Wu et al. | |
| 2006/0029944 A1 | 2/2006 | Huang et al. | |
| 2006/0135512 A1 | 6/2006 | Boehringer et al. | |
| 2006/0229286 A1 | 10/2006 | Kakigami et al. | |
| 2006/0235002 A1 | 10/2006 | Nagai et al. | |
| 2007/0100135 A1 | 5/2007 | Riggs et al. | |
| 2007/0142452 A1 | 6/2007 | Banner et al. | |
| 2007/0197588 A1 | 8/2007 | Shao et al. | |
| 2007/0203111 A1 | 8/2007 | Shao et al. | |
| 2008/0004327 A1 | 1/2008 | Heffernan et al. | |
| 2008/0004328 A1 | 1/2008 | Dorsey et al. | |
| 2008/0058395 A1 | 3/2008 | Heffernan et al. | |
| 2009/0099248 A1 | 4/2009 | Heffernan et al. | |
| 2009/0149549 A1 | 6/2009 | Zhao et al. | |
| 2010/0016397 A1 | 1/2010 | Fang et al. | |
| 2010/0022612 A1 | 1/2010 | Dorsey et al. | |
| 2010/0029737 A1 | 2/2010 | Heffernan et al. | |
| 2010/0029741 A1 | 2/2010 | Dorsey et al. | |
| 2010/0120740 A1 | 5/2010 | Heffernan et al. | |

FOREIGN PATENT DOCUMENTS

| | | |
|---|---|---|
| CA | 2066593 A1 | 2/1992 |
| CA | 2474451 A1 | 8/2003 |
| CA | 2 492 876 A1 | 1/2004 |
| CA | 2498152 A1 | 3/2004 |
| CA | 2498175 A1 | 3/2004 |
| CA | 2565852 A1 | 11/2005 |
| CA | 2566094 A1 | 12/2005 |
| CA | 2 590 985 A1 | 6/2006 |
| CN | 1106386 A | 8/1995 |
| CN | 1709871 A | 12/2005 |
| CN | 1962656 A | 5/2007 |
| DE | 1124485 B | 3/1962 |
| DE | 3431541 A1 | 3/1986 |
| EP | 0101786 A1 | 3/1984 |
| EP | 0152032 A2 | 8/1985 |
| EP | 0396124 A2 | 11/1990 |
| EP | 1136071 A2 | 9/2001 |
| EP | 1219603 A2 | 7/2002 |
| EP | 1262181 A1 | 12/2002 |
| EP | 1362864 A1 | 11/2003 |
| EP | 1088824 B1 | 1/2004 |
| EP | 1391460 A1 | 2/2004 |
| EP | 1420028 A2 | 5/2004 |
| EP | 2154962 A1 | 2/2010 |
| EP | 2617704 A1 | 7/2013 |
| ES | 2081747 A1 | 3/1996 |
| JP | S50-157342 A | 12/1975 |
| JP | S54-059269 A | 5/1979 |
| JP | S60-172970 A | 9/1985 |
| JP | H01-016786 A | 1/1989 |
| JP | H01-172388 A | 7/1989 |
| JP | H04-077476 A | 3/1992 |
| JP | H05-504769 A | 7/1993 |
| JP | 2000-503996 A | 4/2000 |
| JP | 2004-524276 A | 8/2004 |
| JP | 2005-519037 A | 6/2005 |
| JP | 2006-511453 A | 4/2006 |
| JP | 2007-509097 A | 4/2007 |
| WO | WO-86/00896 A1 | 2/1986 |
| WO | WO-91/11437 A1 | 8/1991 |
| WO | WO-92/09566 A1 | 6/1992 |
| WO | WO-95/17381 A1 | 6/1995 |
| WO | WO-98/42709 A1 | 10/1998 |
| WO | WO-99/10343 A1 | 3/1999 |
| WO | WO-99/18065 A1 | 4/1999 |
| WO | WO-99/40913 A1 | 8/1999 |
| WO | WO-99/40914 A1 | 8/1999 |
| WO | WO-99/48868 A2 | 9/1999 |
| WO | WO-00/25770 A1 | 5/2000 |
| WO | WO-01/02427 A1 | 1/2001 |
| WO | WO-01/27103 A1 | 4/2001 |
| WO | WO-01/42203 A1 | 6/2001 |
| WO | WO-01/49654 A2 | 7/2001 |
| WO | WO-01/79208 A1 | 10/2001 |
| WO | WO-02/12249 A2 | 2/2002 |
| WO | WO-02/20530 A1 | 3/2002 |
| WO | WO-02/30870 A2 | 4/2002 |
| WO | WO-02/31128 A1 | 4/2002 |
| WO | WO-03/002525 A1 | 1/2003 |
| WO | WO-03/016302 A1 | 2/2003 |
| WO | WO-03/039540 A2 | 5/2003 |
| WO | WO-03/063797 A2 | 8/2003 |
| WO | WO-03/074531 A1 | 9/2003 |
| WO | WO-03/074532 A1 | 9/2003 |
| WO | WO-03/091213 A1 | 11/2003 |
| WO | WO-03/092670 A1 | 11/2003 |
| WO | WO-2004/002637 A1 | 1/2004 |
| WO | WO-2004/022537 A2 | 3/2004 |
| WO | WO-2004/026237 A2 | 4/2004 |
| WO | WO-2004/031193 A1 | 4/2004 |
| WO | WO-2004/031194 A1 | 4/2004 |
| WO | WO-2004/039787 A1 | 5/2004 |
| WO | WO-2004/041780 A2 | 5/2004 |
| WO | WO-2004/089470 A2 | 10/2004 |
| WO | WO-2004/113345 A1 | 12/2004 |
| WO | WO-2005/013981 A1 | 2/2005 |
| WO | WO-2005/018637 A1 | 3/2005 |
| WO | WO-2005/020986 A1 | 3/2005 |
| WO | WO-2005/020987 A1 | 3/2005 |
| WO | WO-2005/040166 A1 | 5/2005 |
| WO | WO-2005/046575 A2 | 5/2005 |
| WO | WO-2005/066135 A2 | 7/2005 |
| WO | WO-2005/066143 A2 | 7/2005 |
| WO | WO-2005/089753 A2 | 9/2005 |
| WO | WO-2005/123677 A2 | 12/2005 |
| WO | WO-2006/001958 A2 | 1/2006 |
| WO | WO-2006/004040 A1 | 1/2006 |
| WO | WO-2006/014664 A2 | 2/2006 |
| WO | WO-2006/021000 A2 | 2/2006 |
| WO | WO-2006/077412 A1 | 7/2006 |
| WO | WO-2007/039773 A2 | 2/2007 |
| WO | WO-2007/068621 A1 | 6/2007 |
| WO | WO-2007/081542 A2 | 7/2007 |
| WO | WO-2007/081857 A2 | 7/2007 |
| WO | WO-2007/115185 A2 | 10/2007 |
| WO | WO-2008/005456 A2 | 1/2008 |
| WO | WO-2008/079382 A1 | 7/2008 |
| WO | WO-2008/089453 A2 | 7/2008 |

(56) References Cited

FOREIGN PATENT DOCUMENTS

| WO | WO-2008/151156 A1 | 12/2008 |
|---|---|---|
| WO | WO-2009/020814 A2 | 2/2009 |
| WO | WO-2010/017418 A1 | 2/2010 |

OTHER PUBLICATIONS

Anderson, et al., Resolved 2-arulcuclohexylamines: Effects on Reserpine Akinesia and Central Nervous System Monoamine Synthesis, European Journal of Medicinal Chemistry, 28:63-69 (1993).
Ando, R. et al., 3-Arylacetylamino)-N-methylbenzamides: A Novel Class of Selective Anti-Heliocobacter Pylori Agents, Journal of Medicinal Chemistry, 44(25):4468-4474 (2001).
Arya, V.P. et al., Synthesis of New Heterocycles: Part XV, Synthesis of Novel Cyclic and Acyclic Sulfamides, Indian Journal of Chemistry, 14B(10):766-769 (1976).
Ashton, W.T. et al., Nonpeptide angiotensin II Antagonists Derived from 1H-pyrazole-5-carboxylates and 4-aryl-1H-imidazole-5-carboxylates, Journal of Medicinal Checmistry, 36(23):3595-3605 (1993).
Associate Press, FDA mulls drug to slow late-stage Alzheimer's, CNN.com, http://www.cnn.com/2003/HEALTH/conditions/09/24/alzheimers.drug.ap/index.html> (2003).
Aubert, et al., New Cyclopenta[b]-pyrroles and -pyridines by reaction of 2-azido- and 2-phosphoranylideneaminocyclopent-1 -ene-1-carbaldehydes with aliphatic esters, Journal of the Chemical Society Perkin Transactions, 1(8):1369-1373 (1989).
Azéma, J. et al., Efficient Approach to Acyloxymethyl Esters of Nalidixix Acid and In Vitro Evaluation as Intra-Ocular Prodrugs, Bioorganic Medicinal Chemistry, 14(8):2569-2580 (2006).
Baba, Y. et al., Structure-Based Design of a Highly Selective Catalytic Site-Directed Inhibitor of Ser/Thr Protein Phosphatase 2B (Calcineurin), Journal of the American Chemical Society, 125(3):9740-9749 (2003).
Babu, S. et al., Simple and Facile Oxidation of Aldehydes to Carboxylic Acid Derivatives, Organic Preparations and Procedures International, 26(1):123-125 (1994).
Bagal, S. et al., Radicals from Aldehydes: A Convergent Access to Dienes and σ-Lactones, Synlett, 10:1485-1490 (2006).
Balsamini, C. et al., (e)-3-(2-(N-phenylcarbamonyl)vinyl)pyrrole-2-carboxylic acid derivatives: A Novel Case of Glycine Site Antagonists, Journal of Medicinal Chemistry, 41(6):808-820 (1998).
Balsamini, C. et al., An Improved Route to Cycloalka[b]pyrrole 2-carboxylates, Organic Preparation and Procedure, 29(4):471-473 (1997).
Bambury, R.E. et al., Trifluromethylfurans II, Journal of Hetertocyclic Chemistry, 7(2):269-273 (1970).
Banekovich, C. et al., Synthesis and Biological Activites of Novel Dexibuprofen Tetraacetylriboflavin Conjugates, Bioorganic Chemistry, 17(3):683-687 (2007).
Banfi, et al., Synthesis of New Imidazole Derivatives as Potential Inhibitors of Thromboxane Synthetase, Journal of Heterocyclic Chemistry, 27:215-219 (1990).
Bardakos, et al., Enhydrazine, 10: Einige aliphatische Enhydrazone, Chemie Berlin, 108(7):2161-2170 (1975).
Bartlett, et al., Evaluation of Alternative Approaches for the Synthesis of Macrocyclic Bisindolymaleimides, Organic Biomolecular Chemistry, 2(19):2874-2883 (2004).
BASF Corporation, Borane-tetrahydrofuran Complex (BTHF), Product Bulletin, 1-14 (1975).
Baumes, et al., Recherches sur les enehydrazines: Condensation de methylhydrazones de cetones sur les esters acetyleniques: Synthesis de Carbomethoxypyrroles, Bulletin Society of Chimie France, 227(5-6):1147-1150 (1974).
Beaumont, K. et al., Design of Ester Prodrugs to Enhance Oral Absorption of Poorly Permeable Compounds: Challenges to the Discovery Scientist, Current Drug Metabolism, 4(6):461-485 (2003).

Bedford, et al., Quarternary Salts of 2-[(hydroxyimino)methyl}imidazole: Preparation and in vitro and in vivo evaluation of 1-(alkoxymethyl)-2-[(hydroxyimino)methylimidazolium halides for reactivation of organophosphorus-inhibited acetylecholinesterases, Journal of Medicinal Chemistry, 32(2):493-503 (1989).
Benson, et al., Aliphatic β-Chlorovinyl Aldoximes, Journal of Organic Chemistry, 30)4:1126-1129 (1965).
Bergauer, M. et al., Practical ex-chiral-pool methodology for the synthesis of dopaminergic tetrahydroindoles, Tetrahedron, 60(5):1197-1204 (2004).
Bialer, et al., Pharmacokinetic analysis and antiepileptic activity of tetra-methylcyclopropane analogues of valpromide, Pharmaceutical Research, 13(2):284-289 (1996).
Biggadike, et al., Selective plasma hydrolysis of glucocorticoid gamma-lactones and cyclic carbonates by the enzyme paraoxonase: an ideal plasma inactivation mechanism, Journal of Medicinal Chemistry, 43(1):19-21 (2000).
Birkofer, L. and Ritter, A., The use of silylation in organic syntheses, Angewandte Chemie International Edition, 4(5):417-429 (1965).
Black, D., Product Class 13:1H-Pyrroles, Science of Synthesis: Houben-Weyl Methods of Molecular Transformations, 9:441-552. (2001).
Blanchfield, et al., The Stability of Lipidic Analogues of GnRH in Plasma and Kidnet Preparations: The Stereoselective Release of the Parent Peptide, Bioorganic Medicinal Chemistry Letters, 15(6):1609-1612 (2005).
Bobbitt, et al., Organic Nitrosonium Salts II: Stability Studies and Oxidations of Some Indole Derivatives, Heterocycles, 30(2):1131-1140 (1990).
Bobosik, et al., Synthesis of N-Phenylsulfonyl Protected Furo[3,2-b]pyrroles Collection of Czechoslovakian Chemistry Communications, 59(2):499-502 (1994).
Boeshagen, et al., Ueber 3-Acylimino-3H-1 .2 Benzodithiole, Chemie Berlin, 101(7):2472-2484 (1968).
Borza, et al., Selective NR1/2B N-Methyl-d-asparate Receptor Antagonists Among Indole-2-carboxamides and Benzimidazole-2-carboxamides, Journal of Medicinal Chemistry, 50(5):901-914 (2007).
Braga, et al., Making Crystals from Crystals: A Green Route to Crystal Engineering and Polymorphism, Chemical Communications, 29:3635-3645 (2005).
Bregant, et al., Orthogonally Protected Lanthionines: Synthesis and Use for the Solid-Phase Synthesis of an Analogue of Nisin Ring C, Journal of Organic Chemistry, 70(7):2430-2438 (2005).
Brunner, et al., Asymmetrische Hydrierung von (Z)-α-(Acetylamino)-simtsäure mit einem Rh/norphos-Katalysator, Angewandte Chemie, 91(8):655-656 (1979).
Brunner-Guenat, et al., Esters of L-dopa: Structure-hydrolysis Relationships and Ability to Induce Circling Behaviour in an Experimental Model of Hemiparkinsonism, Journal of Phamaceutical Pharmacology, 47(10):861-869 (1995).
Bueno, et al., Dipeptides as effective prodrugs of the unnatural amino acid (+)-2-aminobicyclo[3.1.0]hexane-2,6-dicarboxylic acid (LY354740), a selective group II metabotropic glutamate receptor agonist, Journal of Medicinal Chemistry, 48(16):5305-5320 (2005).
Bundgaard, et al., Esters of N,N-distributed 2-hydroxyacetamides as a Novel Highly Biolabile Prodrug Type for Carboxylic Acid Agents, Journal of Medicinal Chemistry, 30(3):451-454 (1987).
Byrn, et al., Solid-State Chemistry of Drugs, Social Science Citation Index, Inc., 2:232-247 (1999).
Cai, et al., Synthesis of 2,4,50Trisubstituted Oxazoles, Synthesis, 10:1569-1571 (2005).
Calderon, et al., Novel 1-Phenylcycloalkanecarboxylic Acid Derivatives Are Potent and Selective .sigma. 1 Ligands, Journal of Medicinal Chemistry, 37(15):2285-2291 (1994).
Callis, et al., A Tandem Horner-Emmons Olefination-Conjugate Addition Approach to the Synthesis of 1,5-Disubtituted-6-azabicyclo[3.2.1]octanes Based on the AE Ring Structure of the Noriterpenoid Alkaloid Methyllycaconitine, Journal of Organic Chemistry, 61(14):4634-4640 (1996).

(56) References Cited

OTHER PUBLICATIONS

Cartoon, et al., Lithiation reactions of 1-(2'-bromphenyl)pyrrole and related compounds, Journal of Organometallic Chemistry, 212(1):1-9 (1981).
Chakraborty, et al., Synthesis and Chracteristization of Boc-protected 4-amino and 5-amino-pyrrole-2-carboxylic acid methyl esters, Tetrahedron Letters, 47(27)4631-4634 (2006).
Chapman, et al., The Analytical Reduction of Porphyrins to Pyrroles, Canadian Journal of Chemistry, 49(21):3544-3564 (1971).
Chaubey, et al., Kinetics of the Oxidation of Heterocyclic Aldehydes by Quinolinium Dichromate, Bulletin Chemical Society Japan, 75(10):2215-2220 (2002).
Chen, et al., 4,4-Difluoro-4-bora-3a,4a-diaza-s-indacene (BODIPY) Dyes Modified for Extended Conjugation and Restricted Bond Rotations, Journal of Organic Chemistry, 65(10):2900-2906 (2000).
Chen, et al., Studies on the SAR and pharmacophore of milnacipran derivatives as monoamine transporter inhibitors, Bioorganic Medicinal Chemistry Letters, 18(4):1346-1349 (2008).
Chimichi, et al., New 5-(2-ethenylsubstituted)-3(2H)-furanones with in vitro antiproliferative activity, Tetrahedron, 59(28):5212-5223 (2003).
Cottineau, et al., Synthesis and Hypoglyemic Evaluation of Substituted Pyrazole-5-carboxylic Acids, Bioorganic Medicinal Chemistry Letters, 12(16):2105-2108 (2002).
Crane, S.N. and Corey, E.J., A novel enantioselective synthetic route to omuralide analogues with the potential for species selectivity in proteasome inhibition, Organic Letters, 3(9):1395-1397 (2001).
Cuevas-Yañez, et al., Rhodium(II) catalyzed intramolecular insertion of carbenoids derived from 2-pyrrolyl and 3-indolyl α-diazo-β-ketoesters and α-diazoketones, Tetrahedron, 60(7):1505-1511 (2004).
Cyranski, et al. Aromaticity of dihetero analogues of pentalene dianion. X-Ray and ab initio studies of eight methyl furo[3,2-b]pyrrole-5-carboxylate derivatives and five methyl furo[3,2-b]pyrrole-5-carboxylate derivatives, Tetrahedron, 57(42):8867-8873 (2001).
Damaslo, A.R., Alzheimer's Disease and Related Dementias, Cecil Textbook of Medicine, 20(2):1992-1996 (1996).
Dandarova, et al., 13C NMR spectra of some substituted furo[3,2-b] pyrroles, Magnetic Resonating Chemistry, 28(9):830-831 (1990).
Das, et al., Synthesis of some N-substituted carbazoles and their larvicidal studies, Journal of Indian Chemistry Society, 82:158-160 (2005).
Database Beilstein, Beilstein Institute for Organic Chemistry, Frankfurt-Main, DE; Database Accession No. BRN: 10196160 Abstract, European Journal of Organic Chemistry, 21:4670-4679 (2005).
Database Beilstein, Beilstein Institute for Organic Chemistry, Frankfurt-Main, DE; Database Accession No. BRN: 1074598 Abstract, Canadian Journal of Chemistry, 56(10):1429-1434 (1978).
Database Beilstein, Beilstein Institute for Organic Chemistry, Frankfurt-Main, DE; Database Accession No. BRN: 4185621 Abstract, Collection of Czechoslovakian Chemical Communications, 51(1):106-111 (1986).
Database Beilstein, Beilstein Institute for Organic Chemistry, Frankfurt-Main, DE; Database Accession No. BRN: 4429388 Abstract, Collection of Czechoslovakian Chemical Communications, 49(1):65-70 (1984).
Database Beilstein, Beilstein Institute for Organic Chemistry, Frankfurt-Main, DE; Database Accession No. BRN: 7812555 Abstract, Collection of Czechoslovakian Chemical Communications, 62(10):1612-1622 (1997).
Database CAPLUS on STN, Account No. 1977:83511, Koe, Journal of Pharmacology Experimental Therapies, 199(3):649-661 (1976).
De Luca, et al., A new, simple procedure for the synthesis of formyl amides, Synlett, 14:2570-2572 (2004).
Delgado, A. et al., Synthesis and Conformational Assignment of cis- and trans-2-amino-1-arylcyclohexanols, Cancer Journal of Chemsitry, 63(11):3186-3194 (1985).

Denmark, et al., Organocerium additions to SAMP-hydrazones: General Synthesis of Chiral Amines, Journal of Organic Chemistry, 109(7):2224-2225 (1987).
Denmark, S.E. and Matsuhashi, H., Chiral fluoro ketones for catalytic asymmetric epoxidation of alkenes with oxone, Journal of Organic Chemistry, 67(10):3479-3486 (2002).
Dhanak, et al., Studies in the Protection of Pyrrole and indole Derivatives, Journal of Organic Chemistry, 1:2181-2186 (1986).
Durrer, et al., Structure-metabolism relationships in the hydrolysis of nicotinate esters by rat liver and brain subcellular fractions, Pharmacology Research, 8(7):832-839 (1991).
El-Nagger, et al., Synthesis and Biological Activity of Some New Aminoacylcabazole Derivatives, Journal of Heterocyclic Chemistry, 1(19):1025-1028 (1982).
Elghamry, Synthesis of ethyl pyrrole-2-carboxylates: A regioselective cyclization of enaminones under knorr-type conditions, Synthesis Community, 32(6):897-902 (2002).
Eliel, Infelicitous Stereochemical Nomenclatures, Chirality, 9(5-6):428-430 (1997).
English, et al., Orally effective acid prodrugs of the beta-lactamase inhibitor sulbactam, Journal of Medicinal Chemistry, 33(1):344-347 (1990).
Eras, et al., Reactivity of thienopyrroles: Synthesis of isomeric nirto and bromothienopyrroles, Journal of Heterocyclic Chemistry, 21(1):215-217 (1984).
Estep, An Efficient Synthesis of 4-Hydroxy-1H-indole-2-carbonitrile and its Conversion to DPI 301-106, Synthesis Communications, 25(4):507-514 (1995).
Fagan, et al., A New Approach to the Core of Rosephilin, Tetrahedron Letters, 40(33):6117-6120 (1999).
Ferguson, et al., N-Acetyl-5,6-dihydrofuro[3,2-b]pyrid-2-one: C9H9NO3, Crystalline Structure Communications, 5:911-914 (1976).
Fischer, et al., On Benzisothiazolones: A Series with a Wide Range of Bacteriostatic and Fungistatic Activity, Arznemittel-Forschung, 14(12):1301-1306 (1964).
Fischer, et al., Synthese einiger Pyrrole und ihre Umsetzungen, Justus Liebigs Annals Chemistry, 492(1):128-155 (1931).
Fischer, et al., Synthesen der Opso- und Hämopyrrolcarbonsäure: Neue Synthese von Koproporphyrin II, Justus Liebigs Annals Chemistry, 462(1):240-250 (1928).
Fischer, et al., Synthesen von Koproporphyrin I und II: Sowie Mesoporphyrin II, V und XII, Justus Liebigs Annals Chemistry, 466(1):147-178 (1928).
Fisera, et al., Correlation of Kinetic Data of 1,3-Dipolar Cycloadditions of C-Benzoyl-N-phenylnitrones with the Homo Energies of Furan Derivatives, Collection of Czechoslovakian Chemistry Communications, 46:1504-1512 (1981).
Fisera, et al., Cycloadditions of C-Benzoyl-N-phenylnitrone with Furocondensed Derivatives, Collection of Czechoslovakian Chemistry Communications, 46:2421-2427 (1981).
Flaugh, et al., Synthesis of Porphyrins: Deoxophylloerythrotioporphyrin, Journal of American Chemical Society, 90(24):6877-6879 (1968).
Foucaud, et al., The [1 + 4] cycloaddition of isocyanides with 1-aryl-2-nitro-1-propenes: Methyl 2-nitro-3-arylpropenoates and methyl 2-nitro-2,4-pentadienoates. Synthesis of 1-hydroxypyrroles, Journal of Organic Chemistry, 48(21):3639-3644 (1983).
Fraga-Dubreuil, J. and Bazureau, J.P., Grafted ionic liquid-phase-supported synthesis of small organic molecules, Tetrahedron Letters, 42(35):6097-6100 (2001).
Franciò, et al., Asymmetrica Catalysis with Chiral Phosphane/Phosphoramidite Ligands Derived from Quinoline, Angewandte Chemie International Edition, 39(8):1428-1430 (2000).
Frisell, et al., Flavoenzyme Catalysis: Substrate-Competitive Inhibition of D-Amino Acid Oxidase, Journal of Biological Chemistry, 223:75-83 (1956).
Fu, et al., Design and syntheses of novel bis(I-amino acid) ester prodrugs of 9-[2- (phosphomethoxy)ethyl]adenine (PMEA) with improved anti-HBV activity, Bioorganic Medicinal Chemistry Letters, 17(2):465-470 (2007).

(56) References Cited

OTHER PUBLICATIONS

Fukuda, et al., Tensidols, New Potentiators of Antifungal Miconazolem Activity, Journal of Antibiotics, 59(8):2160-2165 (1964).
Gabbutt, et al., A Facile Synthesis of Some Benzothiopyrano[4,3-b]pyrroles, Journal of Chemical Research, 3:102-103 (2007).
Gale, et al., Preparation and Reactions of 5-Carbethoxythieno[3,2-b]pyrrole and Some of Its Derivatives, Journal of Organic Chemistry. 29(8):2160-2165 (1964).
Garg, et al., Development of an Enantiodivergent Strategy for the Total Synthesis pf (+)- and (-)-Dragmacidin F from a Single Enantiomer of Quinic Acid, Journal of the Americam Chemical Society, 127(16):5970-5978 (2005).
Gelas-Mialhe, et al., Photochemical heterocyclization of functionalized dienamines, Journal of Organic Chemistry, 52(24):5395-5400 (1987).
Gelas-Mialhe, et al., Réactivité des N-vinylaziridines fonctionnalisées: Synthèse de dérivés des α,β-déhydro α-amino acides, Canadian Journal of Chemistry, 60(22):2830-2851 (1982).
Geraldine, et al., How an Increase in the Carbon Chain Length of the Ester Moiety affects the Stability of a Homologous Series of Oxprenolol Esters in the Presence of Biological Enzymes, Journal of Pharmacological Science, 87(7):880-885 (1998).
Gross, et al., Direct Observation of 1-azafulven-6-one and annelated derivative, Journal of Chemical Society Chemical Communications, 6:360-361 (1982).
Grygorenko, et al., Stereoselective synthesis of 2,4-methanoproline homologues, Tetrahedron Asymmetrey, 17(2):252-258 (2006).
Guan, et al., Design and Synthesis of Aminopropyl Tetrahydroindole-based Indolin-2-ones as Selective and Potent Inhibitors of Src and Yes Tyrosine Kinase, Bioorganic Medicinal Chemistry Letters, 14(1):187-190 (2004).
Haginoya, et al., Synthesis and Conformational Analysis of a Non-Amidine Factor Xa Inhibitor that Incorporates 5-methyl-4,5,6,7-tetrahydrothiazolo[5,4-c]pyridine as S4 binding element, Journal of Medicinal Chemsitry, 47(21):5467-5182 (2004).
Haj-Yehia, et al., Pharmacokinetic analysis of the structural requirements for forming "stable" analogues of valpromide, Pharmaceutical Research, 9(8):1058-1063 (1992).
Haj-Yehia, et al., Structure-pharmacokinetic Relationships in a Series of Valpromide Derivatives with Antiepilptic Activity, Pharmaceutical Research, 6(8):683-689 (1989).
Harada, et al., A simple preparation of chloromethyl esters of the blocked amino acids, Synthesis Communications, 24(6):767-772 (1994).
Harrack, et al., PtCl2-Catalyzed Cycloisomerizations of 5-En-1-yn-3-ol Systems, Jounrnal of the American Chemical Society, 126(8):8656-8657 (2004).
Harrison, et al., Cyclopenta[b]indoles: Model Studies Towards the Tremorgenic Mycotoxins, Journal of the Chemical Society, 2(9):1131-1136 (1995).
Harwood, L.M. and Kitchen, L.C., Tandem generation and intramolecular trapping of chiral stabilised azomethine ylids with alkyne dipolarophiles, Tetrahedron Letters, 34(41):6603-6606 (1993).
Hauptmann, et al., Beiträge zum Reaktionsverhalten von 2-Aminovinylcarbonyverbindungen, Journal für Praktische Chemie, 314(2):353-364 (1972).
Hauptmann, et al., Eine neue Synthese Substituierter Thiophene und Pyrrole, Tetrahedron Letters, 9(11):1317-1319 (1968).
Hemetsberger, et al., Syntheses und Thermolyse von α-Azidoacrylestern, Monatshefte für Chemie, 103(1):194-204 (1972).
Hillenweck, et al., Chlorothalonil Biotransformation by Gastrointestinal Microflora: In Vitro Comparative Approach in Rat, Dog, and Human, Pesticidic Biochemical Physiology, 58(1):34-48 (1997).
Hilton, et al., Observatinos on the Reactivity of Thiyl Radicals Derived from 3,6-epidithiodiketopiperazine-2,5-diones and related congeners, Bioorganic Medicinal Chemistry Letters, 15(9):2239-2242 (2005).

Hoffman, Organic Chemistry: An Intermediate Text, Second Edition (2004).
Holmes, E.T. and Snyder, H.R., Reactions of N-Benzylthieno[3,2-b]pyrrole. I. Metalation and an Electrophilic Substitution, Journal of Organic Chemistry, 29(8):2155-2160 (1964).
Hori, M., Syntheses of Analgesics. XIV. Aminocyclohexane Derivatives. 8., Yakugaku Zasshi, 78:11-14 (1958).
Howarth, et al., Pyrroles and Related Compounds. Part XXVI. Pyrrole beta-keto-esters, Journal of Chemical Society Perkin Translation, 1:490-501 (1974).
Hu, et al., Synthesis of a Porphyrin with Fused Five- and Seven-membered Exocyclic Rings from a Cross-conjugated Teracyclic Dipyrrole, Synlett, 11:909-910 (1994).
Iilyin, et al., Synthesis of Annelated Azaheterocycles Containing a 5-Carbamoylpyrazin-3-one Fragment by a Modification of the Four-Component Ugi Reaction, European Journal of Organic Chemsitry, 21:4670-4679 (2005).
Ikegami, et al., Synthesis and Pharmacological Activity of O-(5-isoxazolyl)-L-serine, Chemical Pharmalogy Bulletin, 48(2):278-280 (2000).
Ingram, et al., Investigation of Enzyme Activity by SERRS using Poly-Functionalised Benzotriazole Derivatives as Enzyme Substrates, Organic Biomolecular Chemistry, 4(15):2869-2873 (2006).
International Search Report for PCT/US2008/065571, 2 pages (Sep. 2, 2008).
Inukai, et al., ortho-Disubstituted F-Benzenes. III. Preparation of (F-Benzo)heterocyclic Compounds from F-Benzoic Acid and F-Phenol, and the Reactions of Some Intermediary f-Benzoyl- and F-Phenoxy Compounds, Bulletin Chemical Society of Japan, 45(11):3447-3452 (1981).
Iranpoor, et al., A Rapid and Facile Conversion of Primary Amides and Aldoximes to Nitriles and Ketoximes to Amides with Triphenylphosphine and N-Chlorosuccinimide, Synthesis Communication, 32(16):2535-2541 (2002).
Isoherranen, et al., New CNS-active Drugs which are Second-Generation Valproic Acid: Can They Lead to the Development of a Magic Bullet, Current Opinions in Neurology, 16(2):203-211 (2003).
Jacob, et al., gamma-Aminobutyric Acid Esters. 2. Synthesis, Brain Uptake, and Pharmacological Properties of Lipid Esters of Gamma-Aminobutyric Acid, Journal of Medicinal Chemistry, 28(1):106-110 (1985).
Java, et al., Chimie Organique.—Synthesis de selenolo, furo et pyrrolopyrroles, Comptes Rendus de l'Académie des Sciences, 281(19):793-795 (1975).
Jolicoeur, et al., Pyrrole Protection, Tetrahedron, 62(50):11531-11563 (2006).
Katritzky, et al., Efficient Conversion of Carboxylic Acids into N-Acylbenzotriazoles, Synthesis, 18:2795-2798 (2003).
Katritzky, et al., Novel Synthesis of Bicycles with Fused Pyrrole, Indole, Oxazole, and Imidazole Rings, Journal of Organic Chemistry, 69(26):9313-9315 (2004).
Katritzky, et al., Regiospecific C-Acylation of Pyrroles and Indoles Using N-Acylbezotriazoles, Journal of Organic Chemistry, 68(14):5720-5723 (2003).
Katterle, et al., A heck-type coupling for the synthesis of novel bridged metallochlorin-fullerene C60 dyads, European Journal of Organic Chemistry, 2:414-422 (2006).
Keener, et al., Synthesis of 6-substituted thieno[3,2-b]pyrroles, Journal of Organic Chemistry, 33(4):1355-1359 (1968).
Kesel, Synthesis of Novel Test Compounds for Antiviral Chemotherapy of Severe Acute Respiratory Syndrome (SARS), Current Medicinal Chemistry, 12(18):2095-2162 (1968).
Khanna, et al., Evaluation of Glycolamide Esters of Indomethacin as Potential Cyclooxygenase-2 (COX-2) Inhibitors, Bioorganic Medicinal Chemistry, 14(14):4820-4833 (2006).
Kittredge, et al., alpha-Helical Polypeptide Films Grown From Sulfide or Thiol Linkers on Gold Surfaces, Helvetica Chimica Acta, 85(3):788-798 (2002).
Kleinspehn, et al., The Synthesis of Some β,β-Dipyrrylpropionic Esters, Journal of the American Chemical Society, 76(220:5641-5646 (1954).

(56) References Cited

OTHER PUBLICATIONS

Koe, Molecular Geometry of Inhibitors of the Uptake of Catecholamines and Serotoninin Synaptosomal Preparations of Rat Brain, Journal of Pharmacology Experimental Therapy, 199(3):649-661 (1976).

Kralovicova, et al., Electrophilic Substitution Reactions of Furo[3,2-b]pyrrole Derivatives, Collection of Cezechoslovakian Chemistry Communications, 51(1):106-111 (1986).

Krayushkin, et al., Synthesis of Photochromic 1,2-Dihetarylethene using Regioselective Acylation of Thienopyrroles, Organic Letters, 4(22):3879-3881 (2002).

Kren, et al., Clustered ergot alkaloids modulate cell-mediated cytotoxicity, Bioorganic Medicinal Chemistry, 10(2):415-424 (2002).

Krutosikova, et al., Addition and Cycloaddition Reactions of Furo[3,2-b]pyrroles and Their Benzo[b] Analogues: An NMR Study of Structure of Products, Collection of Czechoslovakian Chemistry Communications, 53(5):1770-1778 (1988).

Krutosikova, et al., Effect of Microwave Irradiation on Reaction of Furo[3,2-b]pyrrole and Furo[3,2-b]pyrrole-2-carbaldehydes with Some Active Methylene Compounds, ARKIVOC, 3:409-420 (2000).

Krutosikova, et al., Reactions of Ethyl 2-(4-chlorophenyl)-4H-furo[3,2-b]pyrrole-5-carboxylate, Collection of Czechoslovakian Chemistry Letters, 45(3):2949-2957 (1980).

Krutosikova, et al., Reactions of furo[3,2-b]pyrroles and their benzo[b] analogues, Chemistry Papers, 42(1):89-95 (1988).

Krutosikova, et al., Reactions of Methyl 2-Formylfuro[3,2-b]pyrrole-5-carboxylates, Chemistry Papers, 50(2):72-76 (1996).

Krutosikova, et al., Substituted 4-Benzylfuro[3,2-b]pyrrole, Collection of Czechoslovakian Chemistry Letters, 57(5):1487-1494 (1992).

Krutosikova, et al., Substituted vinyl azides in the synthesis of condensed nitrogen heterocycles, Chemistry Papers, 48(4):268-273 (1994).

Krutosikova, et al., Synthesis and Reactions of 4-Oxiranylmethylfuro[3,2-b]pyrroles and their benzo derivatives, Chemistry of Heterocyclic Compounds, 37(12):1511-1517 (2001).

Krutosikova, et al., Synthesis and Reactions of 8-Hydrazinofuro[2',3':4,5]pyrrole-[1,2-d][1,2,4]triazines, Collection of Czechoslovakian Chemistry Community, 62(10):1612-1622 (1997).

Krutosikova, et al., Synthesis and Reactions of Flurocodensed Derivatives, Collection of Czechoslovakian Chemistry Community, 49(1):65-70 (1984).

Krutosikova, et al., Synthesis and Reactions of Furo[3,2-b]pyrroles Derivatives, Collection of Czechoslovakian Chemistry Communications, 46:2564-2572 (1981).

Krutosikova, et al., Synthesis and Reactions of Furo[3,2-b]pyrroles, Molecules, 2(4):69-79 (1997).

Kukolja, et al., Orally Absorbable Cephalosporin Antibiotics. 2. Structure-Activity Studies of Bicycle Glycine Derivatives of 7-aminodeacetoxycephalosporanic Acid, Journal of Medicinal Chemistry, 28(12):1896-1903 (1985).

Kumar, et al., Synthesis and Biological Evaluation of Thiophene [3,2-b] pyrrole derivatives as potential anti-inflammatory agents, Bioorganic Medicinal Chemistry, 12(5):1221-1230 (2004).

Kuo, et al., G-Protein Coupled Receptors: SAR Analyses of Neurotransmitters and Antagoinsts, Journal of Clinical Pharmacology Therapy, 29(3):279-298 (2004).

Lamboley, et al., Synthesis and properties of conformationally constrained analogues of floral-type odorants, Helvetica Chimica Acta, 87(7):1767-1793 (2004).

Lash, et al., Influence of carbocyclic rings on porphyrin cyclizations: synthesis of geochemically significant cycloalkanoporphyrins, Energy Fuels, 4(6):668-674 (1990).

Lash, et al., Normal and Abnormal Heme Biosynthesis. 2.1 Synthesis and Metabolism of Type-II Pentacarboxylic Porphyrinogens: Further Experimental Evidence for the Enzymic Clockwise Decarboxylation of Uroporhyrinogen-III, Journal of Organic Chemsitry, 64(2):478-487 (1999).

Lash, et al., Porphyrins with Exocyclic Rings. 1. Chemsitry of 4,5,6,7-tetrahydro-1H-indoles: Synthesis of Acetoxy Derivatives, Dihydroindoles, and Novel Porphyrins with Four Exocyclic Rings, Journal of Organic Chemistry, 57(18):4809-4820 (1992).

Lash, et al., Porphyrins with Exocyclic Rings. Part 3. A reassessment on the Utility of Cyclopenta[b]pyrroles in the synthesis of porphyrin molecular fossils: Preparation of Three Type II Porphyrins related to Deoxyphylloerythroetioporphyrin (DPEP), Tetrahedron Letters, 49(20):4159-4172 (1993).

Lash, et al., Recent advances in the synthesis of porphyrins with five-membered exocyclic rings, Energy Fuels, 7(2):172-178 (1993).

Law, et al., The Synthesis and Chemistry of Azolenines. Part 2. A General Synthesis of Pyrrole-2-carboxylic Acid Derivatives by the Reaction of 2H-Azirines with Enamines, and the Crystal and Molecular Structure of Ethyl 3-phenyl-4,5,6,7-tetrahydroindole-2-carboxylate, Journal of Chemical Society Perkin Translations, 1:111-118 (1984).

Layzer, R.B. et al., Section Five—Degenerative Diseases of the Nervous System, Cecil Textbook of Medicine, 20(2):2050-2057 (1996).

Lee, et al., Amphiphilic Amino Acid Copolymers as Stabilizers for the Preparation of Nanocrystal Dispersion, European Journal of Pharmacological Science, 24(5):441-449 (2005).

Lee, et al., An effective and convenient esterification of cephalosporin derivatives by using quarternary ammonium salts as catalysts, Synthesis Communications, 28(23):4345-4354 (1998).

Lerche, et al., Unsetzungen mit Monohydrazonen von Dicarbonylverbindungen, V: Umsetzungen von Hyrazonoethylidenammonium-Salzen and Hydrazonoaldehyden mit Grignard-Verbindungen, Chemistry Berlin, 111(3):1195-1209 (1978).

Li, et al., Synthesis of Deoxophylloerythroetioporphyrin (DPEP) and three ring homologs by an imprived b-bilene methodology, Tetrahedron Letters, 39(47):8571-8574 (1998).

Liederer, et al., Ensymes involved in the Bioconversion of Ester-based prodrugs, Journal of Phamacological Sciene, 95(6):1177-1195 (2006).

Liederer, et al., Stability of oxymethyl-modified coumarinic acid cyclic prodrugs of diasteretomeric opioid peptides in biological media from various animal species including human, Jounral of Pharmacological Science, 94(10):2198-22206 (2005).

Liu, et al., Facile construction of the pentacyclic framework of subincanadine B. Synthesis of 20-deethylenylated subincanadine B and 19,20-dihydrosubincanadine B, Organic Letters, 8(1):115-118 (2006).

Liu, et al., Indole-phenylcarbamate Derivatives as Human Non-Pancreatic Secretory Phospholipase A2 Inhibitor, Bioorganic Meidincal Chemistry Letters, 15(20:4540-4542 (2005).

Liu, et al., The Synthesis of Camostat Intermediate, Huaxue Shiji, 278(6):371-372 (2006).

Ma, et al., Hydrolysis of Angiotensin II Receptor Blocker Prodrug Olmesartan Medoxomil by Human Serum Albumin and Identification of its Caralytic Active Sites, Drug Metabolism Disposition, 33(12):1911-1919 (2005).

Majumdar, et al., α-(1H-Imidazol-1-yl)alkyl (IMIDA) carboxylic acid esters as prodrugs of carboxylic acid containing drugs, Tetrahedron Letters, 48(26):4609-4611 (2007).

Mal, et al., Regioselective Synthesis of 1-hydroxycarbazoles via anionic [4+2] cycloaddition of furoindolones: A short synthesis of murrayafoline-A, Tetrahedron Letters, 47(7):1070-1075 (2006).

Mamber, et al., Tubulin polymerization by paclitaxel (taxol) phosphate prodrugs after metabolic activation with alkaline phosphatase, Journal of Pharmacology Experimentail Therapy, 274(2):877-883 (1995).

Mandel, et al., Neuroprotective Stategies in Parkinson's Disease: An Update on Progress, CNS Drugs, 17(10):729-762 (2003).

Marrel, et al., L-Dopa esters as potential prodrugs 1. Physicochemical properties, European Journal of Medicinal Chemistry, 20(5):459-465 (1985).

(56) References Cited

OTHER PUBLICATIONS

Marrel, et al., L-Dopa esters as potential prodrugs 2. Chemical and Enzymatic-Hydrolysis, European Journal of Medicinal Chemistry, 20(5):467-470 (1985).
Martin, et al., Das Diazo-chinon von PQQ als mögliches Reagenz für die Kartierung von Chinoproteinen mittels, Photoattinitätsmarkierung, Helvetica Chemica, 76(4):1674-1677 (1993).
Martin, et al., Do Structurally Similar Molecules have Similar Biological Activity, Journal of Medicinal Chemistry, 45(19):4350-4358 (2002).
McConnaughie, et al., Novel Acridine-Triazenes Prototype Combilexins: Synthesis, DNA Binding, and Biological Activity, Journal of Medicinal Chemistry, 38(18):3488-3501 (1995).
McLaughlin, Suzuki-Miyaura Cross-Coupling of Benzylic Phosphates with Arylboronic Acids, Organic Letters, 7(22):4875-4878 (2005).
Medforth, et al., Nonplanar Distortion Modes for highly Substituted Porphyrins, Journal of the American Chemical Society, 114(25):9859-9869 (1992).
Meltzer, et al., The Synthesis of Bivalent 2β-carbomethoxy-3β3(3,4-dicholorophenyl)-8-heterobicyclo[3.2.1]octane as probes for proximal binding sites on dopamine and serotonin transporters, Bioorganic Medicinal Chemistry, 16(4):1832-1841 (2008).
Mergen, et al., Antipileptic Activity of 1,3-dihexadecanoylamino-2-valproyl-propan-2-ol, a prodrug of valproic acid endowed with a tropism for the central nervous system, Journal of Pharmaceutical Pharmacology, 43(11):815-816 (1991).
Merisor, et al., Synthesis of New Derivatives in the Izoxazole Class with Potential Antimicrobial Activity, Revista de Chimie, 52(4):206-209 (2001).
Miao, et al., Benzamide derivatives as blockers of Kv1.3 on channel, Bioorganic Medicinal Chemistry Letters, 13(6):1161-1164 (2003).
Mikhaleva, et al., Expedient Synthesis of 1-vinylpyrrole-2-carbaldehydes, Tetrahedron Letters, 47(22):3693-3696 (2006).
Miki, et al., Synthesis of 3-Methoxyellipticine and Ellipticine by Friedel-Crafts Reaction of Indole-2,3-dicarboxylic Anhydride and Selective Demethylation, Heterocycles, 65(11):2693-2703 (2005).
Milkiewicz, et al., Synthesis of a novel series of tetra-substituted furan[3,2-b]pyrroles, Tetrahedron Letters, 44(22):4257-4260 (2003).
Mishra, et al., Synthesis, Characterization and Pharmacological Evaluation of Amide Prodrugs of Ketorolac, European Journal of Medicinal Chemistry, 43(11):2464-2472 (2008).
Mokhallalati, et al., A single-pot synthesis of 1,1,2-trisubstituted 1,2-dihydronaphthalenes in High Enantiomeric Purity, Tetrahedron Letters, 35(25):4267-4270 (1994).
Montero, et al., Solid-Phase combinatorial synthesis of peptide-biphenyl hybrids as calpain inhibitors, Organic Letters, 6(22):4089-4092 (2004).
Morgan, B. and Dolphin, D., Synthesis of hydrocarbon-strapped porphyrins containing quinone and phenolic groups, Journal of Organic Chemistry, 52(24):5364-5374 (1987).
Morissette, S.L. et al., High-throughput crystallization: polymorphs, salts, co-crystals and solvates of pharmaceutical solids, Advanced Drug Delivery Reviews. 56:275-300 (2004).
Mork, et al., Stereoselective Enzymatic Hydrolysis of Various Ester Prodrugs of Ibuprofen and Flurbiprofen in Human Plasma, Pharmaceutical Research, 9(4):492-496 (1992).
Muchowski, et al., Protecting Groups for the Pyrrole and Indole Nitrogen Atom: The [2-(trimethylsily)ethoxy]methyl moiety, Lithiation of 1-[[2-(trimethylsily)ethoxy]methyl]pyrrole, Journal of Organic Chemistry, 49(1):203-205 (1984).
Murakami, et al., The Friedel-Crafts acylation of ethyl pyrrole-2-carboxylate. Scope, Limitations, and Application to Synthesis of 7-substituted indoles, Heterocycles, 27(8):1855-1860 (1988).
Nacci, et al., Polycondensed Heterocycles. I. Synthesis of 11-Oxo-5H, 11-H-pyrrolo[2,1-c][1,4]benzothiazepine, Journal of Heterocyclic Chemistry, 22(2):259-263 (1985).

Nacci, et al., Polycondensed Heterocycles. II. A New Prepaartive Route to 11-Oxo-5H, 11-H-pyrrolo[2,1-c][1,4]benzothiazepine, Journal of Heterocyclic Chemistry, 23(3):769-773 (1986).
Nagatathnam, et al., Design and Synthesis of Novel αla Adrenoceptor-Selective Dihydrpyridine Antagonists for the Treatment of Benign Prostatic Hyperplasia, Journal of Medicinal Chemistry, 41(26):5320-5333 (1998).
Nagel, et al., Enantioselektive Katalyse, 4. Synthese N-substituierter (R,r)-3,4-Bis(diphenylphosphino)-pyrrolidine and Anwendung ihrer Rhodiumkomplexe zur asymmetridchen Hydrierung von α-(Acylamino)acrylsäure-Derivaten, Chemie Berline, 119(11):3326-3343 (1986).
Narasimhan, et al., A QSAR Approach for the Prediction of Stability of Benzoglycolamide Ester Prodrugs, Chemical Pharmacology Bulletin, 54(8):1067-1071 (2006).
Nelson, et al., Stereoselective Synthesis of a Potent Thrombin Inhibitor by a Novel P2-P3 Lactone Ring Opening, Journal of Organic Chemistry, 69(11):3620-3627 (2004).
New, et al., The thieno[3,2-c]pyridine and furo[3,2-c]pyridine rings: new pharmacophores with potential antipsychotic activity, Journal of Medicinal Chemistry, 32(6):1147-1156 (1989).
Newman-Evans, et al., The Influence of Intramolecular Dynamics on Branching Ratios in Thermal Rearrangements, Journal of Organic Chemistry, 55(2):695-711 (1990).
Nielsen, et al., Glycolamide Esters as Biolabile Prodrugs of Carboxylic Acid Agents: Synthesis, Stability, Bioconversion, and Physicochemical Properties, Journal of Pharmacology Science, 77(4):285-298 (1988).
Nielson, et al., Bioreversible quarernery N-acyloxymethyl derivatives of the tertiary amines bupivacaine and lidocaine—synthesis, aqueous solubility and stability in buffer, human plasma and simulated intestinal fluid, European Journal of Pharmacology Science, 24(5):433-440 (2005).
Nudelman, et al., Novel Anticancer Prodrugs of Butyric Acid. 2., Journal of Medicinal Chemistry, 35(4):687-694 (1992).
Nudelman, et al., The role of intracellularly released formaldehyde and butyric acid in the anticancer activity of acylocyalkyl esters, Journal of Medicinal Chemistry, 48(4):1042-1054 (2005).
Ogawa, et al., Preparation of oxygen-bridged aza[15]- and aza[17]annulene dicarboxylates by intramolecular azide cyclization, Tetrahedron Letters, 29(2):219-222 (1988).
Ojida, et al., Highly Enantioselective Reformatsky Reaction of Ketones: Chelation-Assisted Enantioface Discrimination, Organic Letters, 4(18):3051-3054 (2002).
Ouyang, et al., Steric hindrance is a key factor in the coupling reaction of (acyloxy) alkyl-α-halides with phenols to make a new promoiety for prodrugs, Tetrahedron Letters, 43(4):577-579 (2002).
Paine, et al., Regioselectivity of pyrrole synthesis from diethyl aminomalonate and 1,3-diketones: Further Observations, Journal of Organic Chemistry, 52(18):3986-3993 (1987).
Parikh, et al., The Use of Amino Acid Oxidases for the Small-scale Preparation of the Optical Isomers of Amino Acids, Journal of the American Chemical Society, 80(4):953-958 (1958).
Paxéus, et al., Screening for non-regulated organic compounds in municipal wastewater in Göteborg, Sweden, Water Science Technology, 33(6):9-15 (1996).
Pfeiffer, et al., Synthesen and Eigenschaften von Pyrrolindigo-Verbindugen, Liebigs Annals Chemie, 4:564-589 (1980).
Poszávácz, et al., New Synthesis of Naratriptan, Heterocycles, 68(4):713-719 (2006).
Puterova, et al., Reaction of Substituted Furan-2-carboxaldehydes and Furo[b]pyrrole Type Aldehydes with Hippuric Acids, Molecules, 9(1):11-21 (2004).
Puterova, et al., Reactions of Substituted Furan-2-caboxaldehydes and Furo[b]pyrrole Type Aldehydes with Benzothiazolium Salts, Molecules, 9(4):241-255 (2004).
Pérez-Balderas, et al., Synthesis of Multivalent Neoglycoconjugates by 1,3 Dipolar Cycloaddition of Nitrile Oxides and Alkynes and Evaluation of their Lectin-Binding Affinities, Tetrahedron, 61(39):9338-9348 (2005).

(56) References Cited

OTHER PUBLICATIONS

Quizon-Colquitt, et al., Porphyrins with Exocyclic Rings. Part 4. An Improved One Step Synthesis of Cyclopenta[b]pyrroles, Collection of Czechslovakian Chemical Communications, 66(11):1615-1622 (2001).
Rautio, et al., Synthesis and in Vitro Evaluation of Novel Morpholinyl- and Methylpiperzinylacyloxyalkyl Prodrugs of 2-(6-Methoxy-2-naphthyl)propionic Acid (Naproxen) For Topical Drug Delivery, Journal of Medicinal Chemistry, 43(8):1489-1494 (2000).
Rodriguez, et al., Confirmational and Molecular Study of the 4-(2-carboxyethyl)-1,2,3,4-tetrahydrocyclopent[b]indole, Tetrahedron, 41(18):3813-3823 (1985).
Romanova, et al., DC Polargraphic and UV Spectrometric Studies of Substituted Furo[3,2-b]- and Furo[2,3-b]pyrroles, Collection of Czechoslovakian Chemical Communications, 66(11):1615-1622 (2001).
Rosati, et al., Cephalosporins to Carbapenems: 1-oxygenated carbapenems and carbapenams, Journal of Medicinal Chemistry, 33(1):291-297 (1997).
Rose, et al., Preclinical Antitumor Activity of Water-Soluble Paclitaxel Derivatives, Cancer Chemotherapy Pharmacology, 39(6):486-492 (1997).
Salim, et al., Pharmacokinetic Analysis of Esteric Prodrugs of Valproic Acid, Pharmaceutical Research, 7(9):222 (1990).
Sambasivarao, et al., Synthetic approach to pentaleno[2,1-b:5,4-b']diindoles, Journal of Organic Chemistry, 55(12):3858-3866 (1990).
Sandham, et al., Synthesis and Biological Properties of Novel Glucocrticoid Androstene C-17 furoate esters, Bioorganic Medicinal Chemistry, 12(19):5213-5224 (2004).
Sandler, et al., Organic Functional Group Preparations, Academic Press, 3:372-381 (1972).
Satake, et al., The Reaction of Electron Excess Aromatic Heterocycle, 1,4-Dihydropyrrolo[3,2-b]pyrrole and Some Related Compounds with Chlorosulfonyl Isocyanate (CSI), Hetercycles, 43(11):2361-2365 (1996).
Scott, et al., Preparation and Reductive Cyclization of Some Carbon-Alkylated Derivatives of Ethyl 3-Nitro-2-thienylpyruvate, Journal of Organic Chemistry, 29(8):2165-2168 (1964).
Sergievskaya, et al., N-Bis(chloroethyl)amines with Alicyclic and Aromatic Radicals in the Molecules. II., Shurnal Obshchei Kimii, 28:1845-1849 (1958).
Severin, et al., Umsetzungen von Ketonen mit azavinylogen Säureamiden, Chemie Berline, 108(5):1756-1767 (1975).
Sewald, N. and Wendisch, V., Synthesis of Homochiral Camphor Annulated Pyrrole Derivatives, Tetrahedron Asymmetry, 7(5):1269-1272 (1996).
Sha, et al., Synthesis of 2,4-Dihydropyrrolo[3,4-b]pyrroles and 4,6-Dihydro-2H-dipyrrolo[3,4-b:3',4'-d]pyrroles, Heterocycles, 31(4):603-609 (1990).
Shaaya, et al., Anhydride prodrugs for nonsteroidal anti-inflammatory drugs, Pharmaceutical Reserach, 20(2):205-2044 (2003).
Shek, Chemical delivery systems and prodrugs of anticonvulsive drugs, Advancement in Drug Delivery Reviews, 14(2-3):227-241 (1994).
Shirai, et al., Reduction of 1-(m-methoxyphenyl)-4-oxocycloalkanecarbonitriles with lithium aluminum hydride, Nagoya-shirtisu Daigaku Yakugakubu Kenkyu Nenpo, 17:33-37 (1969).
Shirai, et al., Synthesis of spiro[4-hydroxycyclohexane-1,4,2'3'-dihydro-6'-methoxy-1'-substituted-2'-methyl-1'H-isoquinoline], Chemical Pharmaceutical Bulletin, 20(1):41-46 (1972).
Shvedov, et al., Monoarylhydrazone of di- and tricarbonyl compounds in the Knorr synthesis of pyrroles, Kimiya Geterotsiklicheskikh Soedinenii, 3:342-344 (1972).
Silvestri, et al., Simple, short peptide derivatives of a sulfonylindolecarboxamide (L-737,126) active in vitro agaisnt HIV-1 wild type and variants carrying nonOnucleoside reverse transcriptase inhibitor resistance mutations, Journal of Medicinal Chemistry, 47(15):3892-3896 (2004).
Sivy, et al., Structure of a furo[3,2-b]pyrrole derivative, Acta Crytallography, 44(11):2032-2033 (1988).
Skolnick, et al., Antidepressant-like actions of DOV 21,947: A "triple" reuptake inhibitor, European Journal of Pharmacology, 461(2-3):99-104 (2003).
Slawik, et al., Lipophilicity of a Series of 1,2-benzisothiazol-3(2H)-ones determined by reverse-phase thin-layer chromatography, Journal of Chromatography, 952(1-2):295-299 (2002).
Sleath, et al., Synthesis of 7,9-didecarboxytmethoxatin (4,5-dioxo-1H-pyrrolo[2,3-f]quinoline-2-carboxylic acid) and comparison of its chemical properties with those of methoxatin and analogous o-quinoenes. Model Studies directed toward the action of PQQ requiring bacterial oxidoreductases and mammalian plasma amine oxidase, Journal of American Chemical Society, 107(11):3328-3338 (1985).
Sleziak, et al., Furo[2,3-b]pyrrole Derivatives. Syntheses and Reactions in the Furan and Pyrrole Ring, Polymer Journal of Chemistry, 74(2):207-217 (2000).
Sleziak, et al., Reactions of Furo[2,3-b]pyrrole and Furo[2,3-b]pyrrole-Type Aldehydes, Collection of Czechoslovakian Chemical Communications, 64(7):1135-1146 (1999).
Smith, et al., Deacylation and deformylation of pyrroles, Journal of Organic Chemistry Society, 48(24):4779-4781 (1983).
Snyder, et al., Synthesis of the Thieno [3,2-b]pyrrole System, Journal of the American Chemistry Society, 79(10):2556-2559 (1957).
Sohma, et al., Controlled Drug Release: Design and Application of New Water-soluble Prodrugs, Peptide Science: The Japanese Peptide Dociety, 249-252 (2002).
Sorotskaya, et al., The Series of Substituted Butanolides and Butenolides. IV. 4-Arylidene(heteroarylidene)-2-butenolides, Zhurnal Organicheskoi Shimii, 25(1):175-182 (1989).
Soth, et al., Recherches en série hétérocycque. XXIX. Sure des voies d'accès à des thiéno, sélénolo, furo et pyrrolopyrroles, Canadian Journal of Chemistry, 56(10):1429-1434 (1978).
Sparey, et al., The Discovery of Fused Pyrrole Carboxylic Acids as Novel, Potent d-Amino Acid Oxidase (DAO) Inhibitors, Bioorganic Medicinal Chemistry Letters, 18(11):3386-3391 (2008).
STN Registry File No. 67268-37-5. Registry File. Retrieved from STN Mar. 17, 2008. One page.
STN Registry No. 109252-80-4, entered STN Jul. 18, 1987 (1 page).
STN Registry No. 132857-67-1, entered STN Mar. 29, 1991 (1 page).
STN Registry No. 33317-33-8, entered STN Nov. 16, 1984 (1 page).
STN Registry No. 33317-36-1, entered STN Nov. 16, 1984 (1 page).
STN Registry No. 34779-67-4, entered STN Nov. 16, 1984 (1 page).
STN Registry No. 34779-69-6, entered STN Nov. 16, 1984 (1 page).
STN Registry No. 36373-63-4, entered STN Nov. 16, 1984 (1 page).
STN Registry No. 36373-65-6, entered STN Nov. 16, 1984 (1 page).
STN Registry No. 51074-69-2, entered STN Nov. 16, 1984 (1 page).
STN Registry No. 51074-71-6, entered STN Nov. 16, 1984 (1 page).
STN Registry No. 51074-72-7, entered STN Nov. 16, 1984 (1 page).
STN Registry No. 51074-73-8, entered STN Nov. 16, 1984 (1 page).
STN Registry No. 57955-59-6, entered STN Nov. 16, 1984 (1 page).
STN Registry No. 57955-60-9, entered STN Nov. 16, 1984 (1 page).
STN Registry No. 58379-13-8, entered STN Nov. 16, 1984 (1 page).
STN Registry No. 60068-32-8, entered STN Nov. 16, 1984 (1 page).
STN Registry No. 60068-33-9, entered STN Nov. 16, 1984 (1 page).
STN Registry No. 60068-34-0, entered STN Nov. 16, 1984 (1 page).
STN Registry No. 67312-98-5, entered STN Nov. 16, 1984 (1 page).
STN Registry No. 67312-99-6, entered STN Nov. 16, 1984 (1 page).
STN Registry No. 67313-00-2, entered STN Nov. 16, 1984 (1 page).
STN Registry No. 69640-80-8, entered STN Nov. 16, 1984 (1 page).
STN Registry No. 69640-82-0, entered STN Nov. 16, 1984 (1 page).
STN Registry No. 69640-83-1, entered STN Nov. 16, 1984 (1 page).
STN Registry No. 69640-84-2, entered STN Nov. 16, 1984 (1 page).
STN Registry No. 69640-85-3, entered STN Nov. 16, 1984 (1 page).
STN Registry No. 69640-86-4, entered STN Nov. 16, 1984 (1 page).
STN Registry No. 69640-87-5, entered STN Nov. 16, 1984 (1 page).
STN Registry No. 69640-88-6, entered STN Nov. 16, 1984 (1 page).

(56) References Cited

OTHER PUBLICATIONS

STN Registry No. 69640-89-7, entered STN Nov. 16, 1984 (1 page).
STN Registry No. 69640-90-0, entered STN Nov. 16, 1984 (1 page).
STN Registry No. 69640-94-4, entered STN Nov. 16, 1984 (1 page).
STN Registry No. 69740-90-5, entered STN Nov. 16, 1984 (1 page).
STN Registry No. 83957-32-8, entered STN Nov. 16, 1984 (1 page).
STN Registry No. 83957-46-4, entered STN Nov. 16, 1984 (1 page).
STN Registry No. 92321-04-5, entered STN Dec. 17, 1984 (1 page).
STN Registry No. 93144-92-4, entered STN Dec. 18, 1984 (1 page).
Stuart, et al., Cobalt-mediated Akylation of Siloxy Furans, Heterocycles, 32(5):949-963 (1991).
Svahn, et al., Tranexaminc Acid Derivatives with Enhanced Absorption, Journal of Medicinal Chemsitry, 29(4):448-453 (1986).
Takahashi, et al., Asymmetric α-Substituted Phenethylamines. I. Synthesis of Optically Pure 1-Aryl-N-(2'-hydroxy-1'-isopropylethyl)-2-phenylethlamines, Chemical Pharmaceutical Bulletin, 30(9):31660-3166 (1982).
Tammara, et al., Morpholinoalkyl ester prodrugs of diclofenac: Synthesis, in Vitro and in Vivo Evaluation, Journal of Phamaceutical Sciences, 83(5):644-648 (1994).
Triebs, et al., Über einige Pyrrolderivative mit angegliedertem isocyclischem Ring. Bz-Tetrahydrindole and Cyclopentenopyrrole, Justus Liebigs Annals Chemie, 517:152-169 (1935).
Trost, et al., Palladium-Catalyzed Enantioselective C-3 Allylation of 3-Substituted-1H-Indoles Using Trialkyboranes, Journal of the American Chemical Society, 128(19):6314-6315 (2006).
Ueda, et al., Novel Water Soluble Phosphate Prodrugs of Taxol® Possessing in Vivo Antitumor Activity, Bioorganic Medicinal Chemistry Letters, 3(8):1761-1766 (1993).
Ueda, et al., Novel Water-Soluable Phosphate Derivatives of 2'-ethoxy carbonylpaclitaxel as Potential Prodrugs of Paclitaxel: Synthesis and Antitumor Evaluation, Bioorganic Medicinal Chemistry Letters, 5(3):247-252 (1995).
Urbach, et al., Eine einfache diastereoselektive Synthese von (1SR,3SR,5SR)-2-Azabicyclos [3.3.0] octan-3-carbonsäure, Tetrahedron Letters, 26(15):1839-1842 (1985).
Van Herk, et al., Pyrazole Derivatives as Partial Agonists for the Nicotinc-Acid Receptor, Journal of Medicinal Chemistry, 46(18):3945-3951 (2003).
Vincini, et al., Biological Studies on 1,2-benzisothiazole derivatives. I. Evaluation of antibacterial, antifungal and DNA-damaging activity, Farmaco, 44(5):511-517 (1989).
Vincini, et al., Sintesi e proprieta antiflogistiche antipiretiche ed analgesiche di 5-(1,2-benzisotiazolil)tetrazoli, Farmaco, 41(2):111-118 (1986).
Vincini, et al., Sintesi e proprieta antiflogistiche antipiretiche ed analgesiche di acidi 5-benzisotiazolilalcanoici e di loro deivati funzionali, Farmaco, 39(10):817-829 (1984).
Vippagunta, S.R. et al., Crystalline Solids, Advanced Drug Delivery Reviews, 48:3-26 (2001).
Viswanathan, et al., Free Radical-Mediated Aryl Amination and Its Use in a Convergent [3 + 2] Strategy for Enantioselective Indoline α-Amino Acid Synthesis, Journal of the American Chemical Society, 125(1):163-168 (2003).
Vitali, et al., Richerche nella classes dei ditocidi 3-benzisotiazolacetici, Farmaco Science, 28(1):163-168 (2003).
Vogel, et al., Cycloalkano-2H-pyrrole als stabile Zwischenstufen bei der Umwandlung von β-Cycloalkenyl-α-azidoacrylestern in Cycloalkano-1H pyrrole, Angewandte Chemie, 105(7):1116-1117 (1993).
Vogel, et al., Cycloalkano-2H-pyrrole as a Stable Intermediate in the Conversion of beta-Cycloalkenyl-alpha-azidoacrylates to Cycloalkano-1H pyrroles, Angewandte Chemie International Edition England, 32(7):1051-1052 (1993).
Wang, et al., Synthesis of ethyl cyclopenteno- or cyclohexeno[b]pyrrolyl-2-caboxylates, Youji Huaxue, 17(6):524-528 (1997).

Watanabe, et al., Enantioselective Addition of Chirally Modified Allylborances to N-(trimethylsilyl)benzaldehyde inmine, Tetrahedron Asymmetry, 6(7):1531-1534 (1995).
Welch, et al., Improved Syntheses of [3,2-b]-and [2,3-b]-fused Slenolo-and Thienopyrroles, and of Furo[3,2-b]pyrrole, Heterocyclic Communications, 5(4):305-310 (1999).
Wen, et al., Cell differentiation enhancement by hydrophilic derivatives of 4,8-Dihydrobenzo[1,2-b:5,4-b']dithiophene-4,8-diones in HL-60 leukemia cells, Bioorganic Medicinal Chemistry Letters, 17(10):20908-20912 (2007).
Wensbo, et al., Indole-3-acetic acids and and hetero analogues by one pot synthesis inlcuding heck cyclisation, Tetrahedron, 51(37):10323-10342 (1995).
Wensbo, et al., Indole-3-pyruvic acid oxime ethers and thieno analogues by heck cyclisation. Application to the Synthesis of thia-tryptophans, Tetrahedron, 52(47):14975-14988 (1996).
Wernly-Chung, et al., Structure-reactivity relationships in the chemical hydrolysis of prodrug esters of nicotinic acid, International Journal of Pharmacology, 63(2):129-134 (1990).
West, A.R., Solid State Chemistry and its Applications, Wiley New York, 358-365 (1988).
Wright, et al., Derivatives of 11-(1-piperazinyl)-5H-pyrrolo[2,1-c][1,4]benzodiazepine as central nervous system agents, Journal of Medicinal Chemistry, 23(4):462-465 (1980).
Written Opinion for PCT/US2008/065571, 5 pages (Sep. 2, 2008).
Xue, et al., An Efficient Synthesis of Glycoprotein IIb/IIIa Inhibitor DMP728. A Novel Synthesis of N.alpha-Methylarginine-Containing Peptide, Journal of Organic Chemistry, 60(4):946-952 (1995).
Yardley, et al., 2-Phenyl-2-(1-hydroxycycloalkyl)ethylamine derivatives: synthesis and antidepressant activity, Journal of Medicinal Chemistry, 33(10):2899-2905 (1990).
Yarovenko, et al., Regioselective acylation of methyl 2-methyl-4H-thieno[3,2-b]pyrrole-5- carboxylates, Russian Chemical Bulletin International Edition, 52(2):451-456 (2003).
Yashuhara, et al., Prodrugs of 3-(3,4-dichlorobenzyloxy)-2-amino-6-flurobicyclo[3.1.0]hexane-2,6-dicarboxylic acid (MGS0039): A Potent and Orally Active Group II mGluR antagonist with antidepressant-like potential, Bioorganic Medicinal Chemistry, 14(12):4196-4207 (2006).
Yevich, et al., Synthesis and Biological Evaluation of 1-(1,2-benzisothiazol-3-yl)- and (1,2-benzisoxazol-3-yl)piperazine derivatives as potential antipsychotic agents, Journal of Medicinal Chemistry, 29(3):359-369 (1986).
Yu, et al., The regiospecific C-4 lithiation of 2-(tert-butyldimethylsilyl)-3 furoic acid, Journal of the Chemical Society Perkin Translations, 1(10):2600-2601 (1991).
Yudina, L.N. and Bergman, J., Synthesis and alkylation of indolo[3,2-b]carbazoles, Tetrahedron, 59(8):1265-1275 (2003).
Zani, et al., Biological Studies on 1,2-benzisothiazole derivatives. VI. Antimicrobial Activity of 1,2-benzisothiazole and 1,2-benzisothiazolin-3-one derivatives and some corresponding 1,2-benzisoxazoles, Farmaco, 51(11):707-713 (1996).
Zaragoza, D.F., Side Reactions in Organic Synthesis, Wiley-VCH: Weinheim, 4-41 (2005).
Zhang, et al., Synthesize the china 3-pyrridyl ester analogs of anaddicted analgesic Epobatidine, Journal of Shangqiu Teachers College, 20(5):90-94 (2004).
Zhang, et al., Total Synthesis of the Porphyrin Mineral Abelsonite and Related Petroporphyrins with Five-Membered Exocyclic Rings, Tetrahedron Letters, 44(39):7253-7256 (2003).
Zinoune, et al., Aminoalkylation of Aldehydes with Glyoxal N,N-Dimethlmonohydrazone Yields Stable 4-Substituted Pyrrolin-3-ones, Hetercycles, 28(2):1077-1084 (1989).
Zong, et al., A New and Efficient Synthetic Route Toward 3,4-alkylenedioxypyrrole (XDOP) derivatives via Mitsunoby chemistry, Tetrahedron Letters, 74(21):3521-3523 (2006).

* cited by examiner

PHENYL SUBSTITUTED CYCLOALKYLAMINES AS MONOAMINE REUPTAKE INHIBITORS

CROSS-REFERENCE TO RELATED APPLICATIONS

This application is a continuation of U.S. application Ser. No. 12/131,845, filed on Jun. 2, 2008, which claims priority to U.S. Provisional Application No. 60/941,242, filed on May 31, 2007, the entireties of which are incorporated herein by reference.

FIELD OF THE INVENTION

The invention relates to compounds and compositions for the treatment of neurological disorders.

BACKGROUND OF THE INVENTION

Psychiatric disorders are pathological conditions of the brain characterized by identifiable symptoms that result in abnormalities in cognition, emotion, mood, or affect. These disorders may vary in severity of symptoms, duration, and functional impairment. Psychiatric disorders afflict millions of people worldwide resulting in tremendous human suffering and economic burden due to lost productivity and dependent care.

Over the past several decades, the use of pharmacological agents to treat psychiatric disorders has greatly increased, largely due to research advances in both neuroscience and molecular biology. In addition, chemists have become increasingly sophisticated at creating chemical compounds that are more effective therapeutic agents with fewer side effects, targeted to correct the biochemical alterations that accompany mental disorders.

Yet, despite the many advances that have occurred, many psychiatric diseases remain untreated or inadequately treated with current pharmaceutical agents. In addition, many of the current agents interact with molecular targets not involved with the psychiatric disease. This indiscriminate binding can result in side effects that can greatly influence the overall outcome of therapy. In some cases the side effects are so severe that discontinuation of therapy is required.

Depression is an affective disorder, the pathogenesis of which cannot be explained by any single cause or theory. It is characterized by a persistently low mood or diminished interests in one's surroundings, accompanied by at least one of the following symptoms: reduced energy and motivation, difficulty concentrating, altered sleep and appetite, and at times, suicidal ideation (American Psychiatric Association; *Diagnostic and Statistical Manual of Mental Disorders*, ed. 4. Washington, American. Psychiatric Association, 1994). Major depression is associated with high rates of morbidity and mortality, with suicide rates of 10-25% (Kaplan H I, Sadock B J (eds): *Synopsis of Psychiatry*. Baltimore, Williams & Wilkins, 1998, p. 866). Dual reuptake inhibitors may also be used to reduce fatigue commonly associated with depression (see, for example, "Bupropion augmentation in the treatment of chronic fatigue syndrome with coexistent major depression episode" Schonfeldt-Lecuona et al., *Pharmacopsychiatry* 39(4); 152-4, 2006; "Dysthymia: clinical picture, extent of overlap with chronic fatigue syndrome, neuropharmacological considerations, and new therapeutic vistas" Brunello et al., *J. Affect. Disord.* 52(1-3):275-90, 1999; "Chronic fatigue syndrome and seasonal affective disorder: comorbidity, diagnostic overlap, and implications for treatment" Terman et al., *Am. J. Med.* 105(3A):115S-124S, 1998.).

Depression is believed to result from dysfunction in the noradrenergic or serotonergic systems, more specifically, from a deficiency of certain neurotransmitters (NTs) at functionally important adrenergic or serotonergic receptors.

Neurotransmitters produce their effects as a consequence of interactions with specific receptors. Neurotransmitters, including norepinephrine (NE) and/or serotonin (5-hydroxytryptamine, or 5-HT), are synthesized in brain neurons and stored in vesicles. Upon a nerve impulse, NTs are released into the synaptic cleft, where they interact with various postsynaptic receptors. Regional deficiencies in the synaptic levels of 5-HT and/or NE are believed to be involved in the etiology of depression, wakefulness, and attention.

Norepinephrine is involved in regulating arousal, dreaming, and moods. Norepinephrine can also contribute to the regulation of blood pressure, by constricting blood vessels and increasing heart rate.

Serotonin (5-HT) is implicated in the etiology or treatment of various disorders. The most widely studied effects of 5-HT are those on the CNS. The functions of 5-HT are numerous and include control of appetite, sleep, memory and learning, temperature regulation, mood, behavior (including sexual and hallucinogenic behavior), cardiovascular function, smooth muscle contraction, and endocrine regulation. Peripherally, 5-HT appears to play a major role in platelet homeostasis and motility of the GI tract. The actions of 5-HT are terminated by three major mechanisms: diffusion; metabolism; and reuptake. The major mechanism by which the actions of 5-HT is terminated is by reuptake through presynaptic membranes. After 5-HT acts on its various postsynaptic receptors, it is removed from the synaptic cleft back into the nerve terminal through an uptake mechanism involving a specific membrane transporter in a manner similar to that of other biogenic amines. Agents that selectively inhibit this uptake increase the concentration of 5-HT at the postsynaptic receptors and have been found to be useful in treating various psychiatric disorders, particularly depression.

Approaches to the treatment of depression over the years have involved the use of agents that increase the levels of NE and 5-HT, either by inhibiting their metabolism (e.g., monoamine oxidase inhibitors) or reuptake (e.g., tricyclic antidepressants or selective serotonin reuptake inhibitors (SSRIs).

There are more than twenty approved antidepressant drugs available in the United States. The classical tricyclic antidepressants (TCAs) currently available block primarily the uptake of NE and also, to varying degrees, the uptake of 5-HT, depending on whether they are secondary or tertiary amines. Tertiary amines such as imipramine and amitriptyline are more selective inhibitors of the uptake of 5-HT than of catecholamines, compared with secondary amines such as desipramine.

Selective serotonin reuptake inhibitors have been investigated as potential antidepressants. Fluoxetine (PROZAC®), sertraline (ZOLOFT®), and paroxetine (PAXIL®) are three examples of SSRIs currently on the U.S. market. These agents do not appear to possess greater efficacy than the TCAs, nor do they generally possess a faster onset of action; however, they do have the advantage of causing less side-effects. Of these three SSRIs, paroxetine is the most potent inhibitor of 5-HT uptake, fluoxetine the least. Sertaline is the most selective for 5-HT versus NE uptake, fluoxetine the least selective. Fluoxetine and sertraline produce active metabolites, while paroxetine is metabolized to inactive metabolites. The SSRIs, in general, affect only the uptake of serotonin and display little or no affinity for various receptor systems including muscarinic, adrenergic, dopamine, and histamine receptors.

In addition to treating depression, several other potential therapeutic applications for SSRIs have been investigated. They include treatment of Alzheimer's disease, aggressive behavior, premenstrual syndrome, diabetic neuropathy, chronic pain, fibromyalgia, and alcohol abuse. For example, fluoxetine is approved for the treatment of obsessive-compulsive disorder (OCD). Of particular significance is the observation that 5-HT reduces food consumption by increasing meal-induced satiety and reducing hunger, without producing the behavioral effects of abuse liability associated with amphetamine-like drugs. Thus, there is interest in the use of SSRIs in the treatment of obesity.

Venlafaxine (EFFEXOR®) is a dual-reuptake antidepressant that differs from the classical TCAs and the SSRIs chemically and pharmacologically in that it acts as a potent inhibitor of both 5-HT and NE uptake. Neither venlafaxine nor its major metabolite have a significant affinity for adrenergic alpha-1 receptors. Venlafaxine possesses an efficacy equivalent to that of the TCAs, and a benign side effect profile similar to those of the SSRIs.

Dopamine is hypothesized to play a major role in psychosis and certain neurodegenerative diseases, such as Parkinson's disease, where a deficiency in dopaminergic neurons is believed to be the underlying pathology. Dopamine affects brain processes that control movement, emotional response, and ability to experience pleasure and pain. Regulation of DA plays a crucial role in our mental and physical health. Certain drugs increase DA concentrations by preventing DA reuptake, leaving more DA in the synapse. An example is methylphenidate (RITALIN®) used therapeutically to treat childhood hyperkinesias and symptoms of schizophrenia. Dopamine abnormalities are believed to underlie some of the core attentional abnormalities seen in acute schizophrenics.

A therapeutic lag is associated with the use of these drugs. Patterns must take a drug for at least three (3) weeks before achieving clinically meaningful symptom relief. Furthermore, a significant number of patients do not respond to current therapies at all. For example, it is currently estimated that up to thirty percent (30%) of clinically diagnosed cases of depression are resistant to all forms of current drug therapy.

SUMMARY OF THE INVENTION

The present invention relates to novel cycloalkylamines and salts thereof. It also relates to novel pharmaceutical compositions, and their use in the treatment of disorders and conditions. Exemplary indications for the compounds of the invention include neurological disorders such as depression (e.g., major depressive disorder, bipolar disorder), fibromyalgia, pain (e.g., neuropathic pain), sleep apnea, attention deficit disorder (ADD), attention deficit hyperactivity disorder (ADHD), restless leg syndrome, schizophrenia, anxiety, obsessive compulsive disorder, posttraumatic stress disorder, seasonal affective disorder (SAD), premenstrual dysphoria as well as neurodegenerative disease (e.g., Parkinson's disease, Alzheimer's disease). The compounds of the invention are also of use to treat or prevent obesity or to treat substance abuse, dependency or addiction, including but not limited to nicotine and cocaine abuse, dependency or addiction.

Hence, in a first aspect the invention provides a compound having the formula:

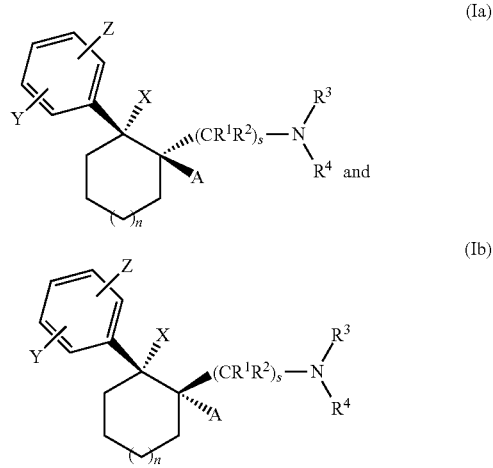

wherein the index n is an integer selected from the group consisting of 0 to 2; and s is an integer selected from the group consisting of 0 to 2. A is a member selected from the group consisting of H, substituted or unsubstituted alkyl, halogen and substituted or unsubstituted haloalkyl, X is a member selected from the group consisting of H, halogen, substituted or unsubstituted alkyl, substituted or unsubstituted aryl, substituted or unsubstituted haloalkyl and $OR^5$, in which $R^5$ is a member selected from the group consisting of H, substituted or unsubstituted, alkyl substituted or unsubstituted heteroalkyl substituted or unsubstituted aryl, substituted or unsubstituted heteroaryl, acyl and $S(O)_2R^{5a}$, in which $R^{5a}$ is a member selected from the group consisting of substituted or unsubstituted alkyl, substituted or unsubstituted heteroalkyl, substituted or unsubstituted aryl, substituted or unsubstituted heteroaryl and substituted or unsubstituted heterocycloalkyl.

Y and Z are members independently selected from the group consisting of halogen, $CF_3$, CN, $OR^9$, $SR^9$, substituted or unsubstituted alkyl, substituted or unsubstituted heteroalkyl, substituted or unsubstituted aryl, substituted or unsubstituted heteroaryl, substituted or unsubstituted heterocycloalkyl $NR^{10}R^{11}$ and $NO_2$. $R^9$ represents H, substituted or unsubstituted alkyl, substituted or unsubstituted heteroalkyl, substituted or unsubstituted aryl, substituted or unsubstituted heteroaryl, or substituted or unsubstituted heterocycloalkyl. The radicals $R^{10}$ and $R^{11}$ independently represent H, $OR^{12}$, acyl, $S(O)_2R^{13}$, substituted or unsubstituted alkyl, substituted or unsubstituted heteroalkyl, substituted or unsubstituted aryl, substituted or unsubstituted heteroaryl or substituted or unsubstituted heterocycloalkyl. $R^{10}$ and $R^{11}$, together with the nitrogen to which they are attached, are optionally joined to form a 3- to 7-membered ring, optionally having from 1 to 3 heteroatom in addition to the nitrogen to which $R^{10}$ and $R^{11}$ are joined.

The symbol $R^{12}$ is a member selected from H, substituted or unsubstituted alkyl, substituted or unsubstituted heteroalkyl, substituted or unsubstituted aryl, substituted or unsubstituted heteroaryl or substituted or unsubstituted heterocycloalkyl. $R^{13}$ is a member selected from substituted or unsubstituted alkyl, substituted or unsubstituted heteroalkyl, substituted or unsubstituted aryl, substituted or unsubstituted heteroaryl and substituted or unsubstituted heterocycloalkyl.

Y and Z, together with the atoms to which they are attached, are optionally joined to form a 5- to 7-membered ring, which can optionally have from 1 to 3 heteroatoms therein. As will be apparent to those of skill in the art, when Y and Z are joined into a ring, the substituents (e.g., $R^9$, $R^{10}$ and $R^{11}$) on atoms incorporated into the ring will be present (e.g., incorporated into the cyclic structure of the ring) or absent as necessary to satisfy the valence of the atom to which these substituents are attached.

$R^1$ and $R^2$ are members independently selected from H, halogen, CN, $CF_3$, $OR^6$, substituted or unsubstituted alkyl, substituted or unsubstituted heteroalkyl, substituted or unsubstituted aryl, substituted or unsubstituted heteroaryl or substituted or unsubstituted heterocycloalkyl. $R^6$ is a member selected from H, substituted or unsubstituted alkyl, substituted or unsubstituted heteroalkyl, substituted or unsubstituted aryl, substituted or unsubstituted heteroaryl or substituted or unsubstituted heterocycloalkyl.

$R^3$ and $R^4$ are members independently selected from H, $OR^7$, acyl, $S(O)_2R^8$, substituted or unsubstituted alkyl, substituted or unsubstituted heteroalkyl, substituted or unsubstituted aryl, substituted or unsubstituted heteroaryl or substituted or unsubstituted heterocycloalkyl. $R^7$ is a member selected from H, substituted or unsubstituted alkyl, substituted or unsubstituted heteroalkyl, substituted or unsubstituted aryl, substituted or unsubstituted heteroaryl or substituted or unsubstituted heterocycloalkyl. $R^8$ is a member selected from substituted or unsubstituted alkyl, substituted or unsubstituted heteroalkyl, substituted or unsubstituted aryl, substituted or unsubstituted heteroaryl and substituted or unsubstituted heterocycloalkyl.

Two or more of $R^1$, $R^2$, $R^3$ and $R^4$, together with the atoms to which they are attached, are optionally joined to form a 3- to 7-membered ring, which optionally includes from 1 to 4, preferably from 1 to 3 heteroatoms.

Any pharmaceutically acceptable salt, solvate, enantiomer, diastereomer, racemic mixture, enantiomerically enriched mixture, and enantiomerically pure form of the above described compounds falls within the scope of the invention.

In a second aspect, the invention provides a pharmaceutical composition including a compound of the invention or a pharmaceutically acceptable salt or solvate thereof, and a pharmaceutically acceptable carrier.

In a third aspect, the invention provides a method of inhibiting binding of a monoamine transporter ligand to a monoamine transporter, such as serotonin transporter, dopamine transporter and norepinephrine transporter. The method includes contacting the monoamine transporter and a compound of the invention. In an exemplary embodiment the monoamine transporter ligand is a monoamine, such as serotonin, dopamine and norepinephrine.

In a fourth aspect, the invention provides a method of inhibiting the activity of at least one monoamine transporter, such as serotonin transporter, dopamine transporter and norepinephrine transporter. The method includes contacting the monoamine transporter and a compound of the invention.

In another aspect, the invention provides a method of inhibiting uptake of at least one monoamine, such as serotonin, dopamine and norepinephrine, by a cell. The method includes contacting the cell with a compound of the invention. In an exemplary embodiment, the cell is a brain cell, such as a neuronal cell or a glial cell.

In yet another aspect, the invention provides a method of treating depression by inhibiting the activity at least one monoamine transporter. The method includes administering to a mammalian subject a compound of the invention. In an exemplary embodiment, the compound of the invention inhibits the activity of at least two different monoamine transporters. In another preferred embodiment, the mammalian subject is a human.

In a further aspect, the invention provides a method of treating a neurological disorder. The method includes administering to a subject in need thereof a therapeutically effective amount of a compound of the invention or a pharmaceutically acceptable salt or solvate thereof. In an exemplary embodiment, the subject is a human.

DETAILED DESCRIPTION OF THE INVENTION

I. Definitions

Figure 1A:
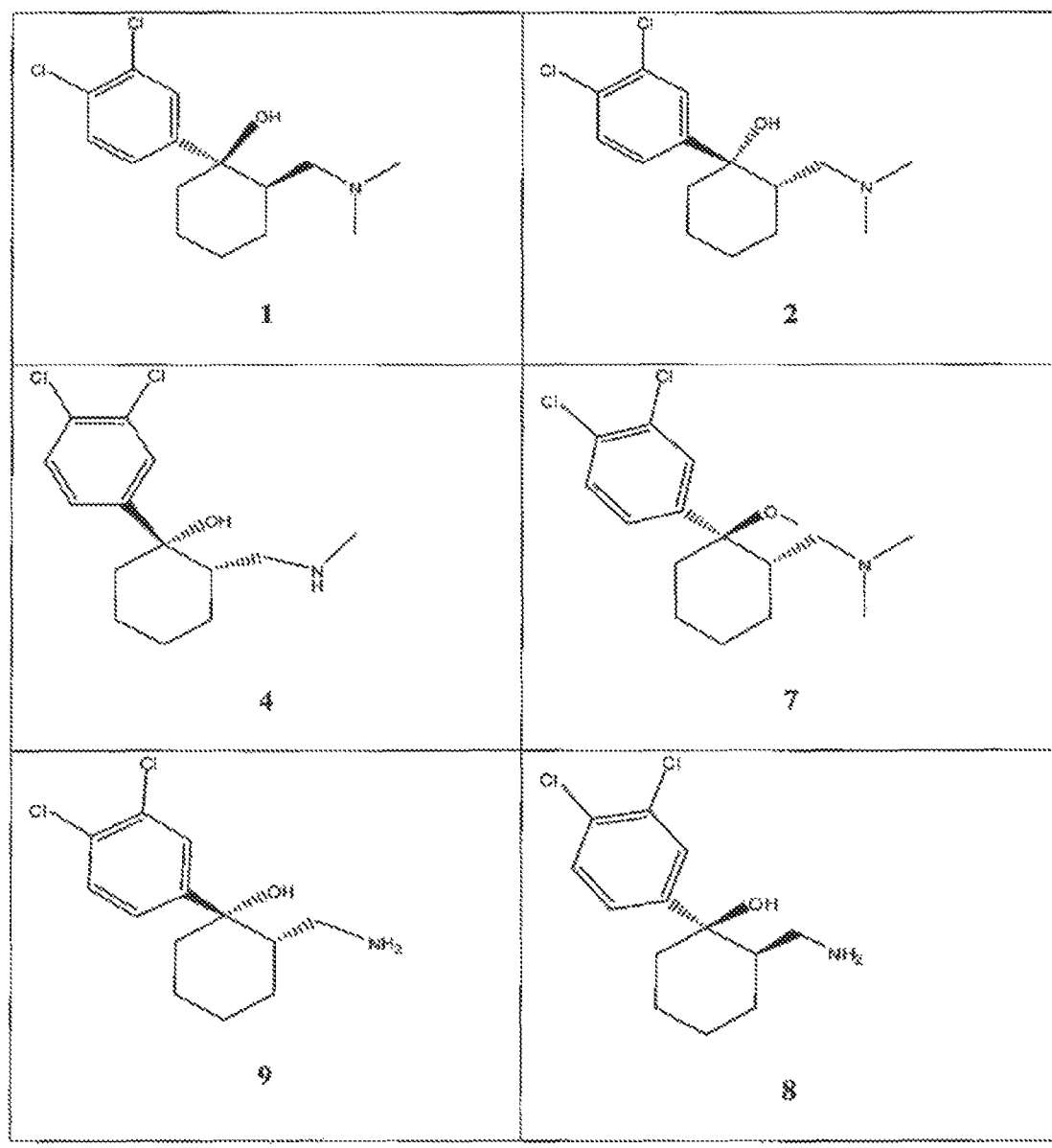
FIG. 1 (A-E) is a table of exemplary compounds of the invention.
Figure 1B:
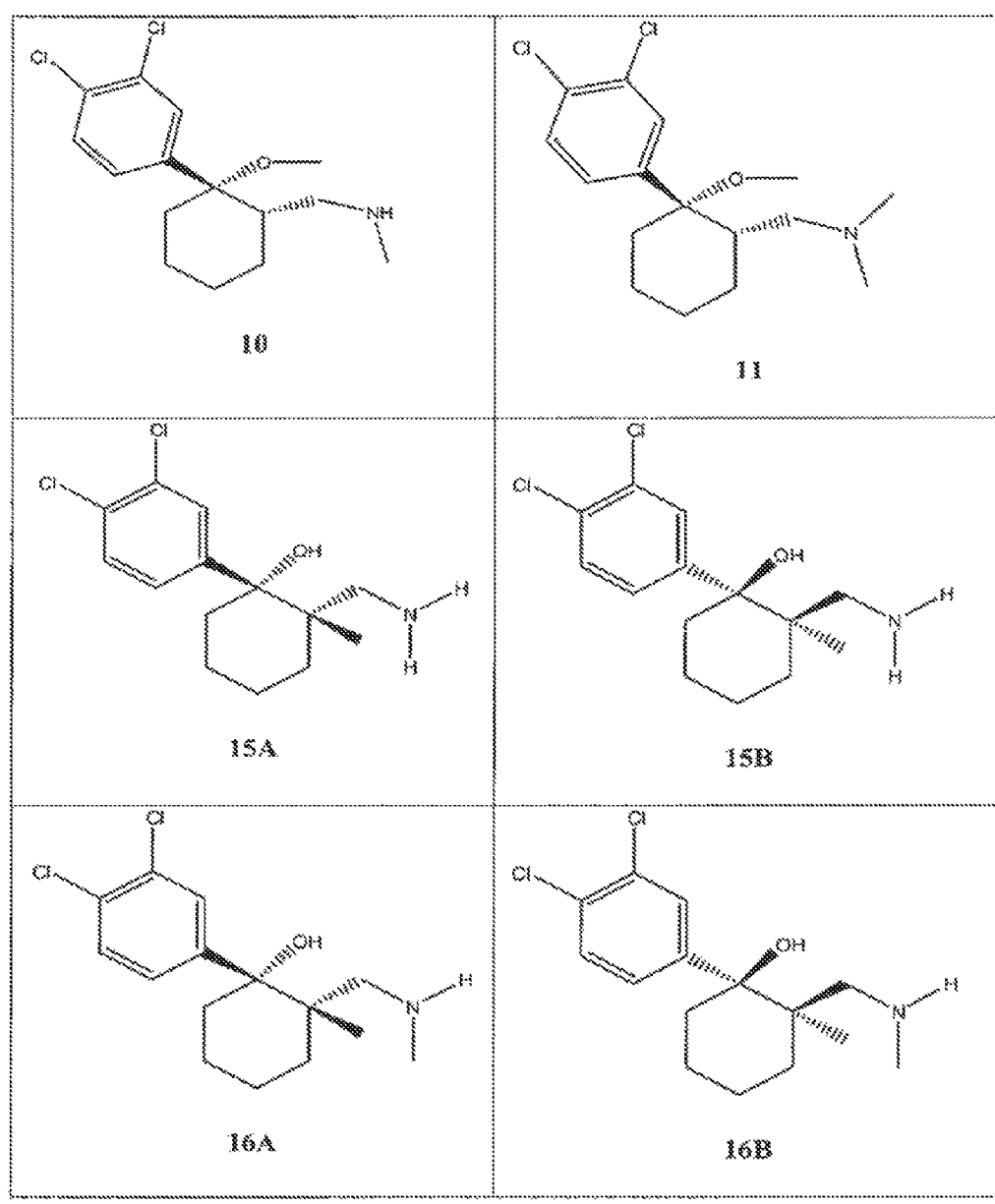
Figure 1C:
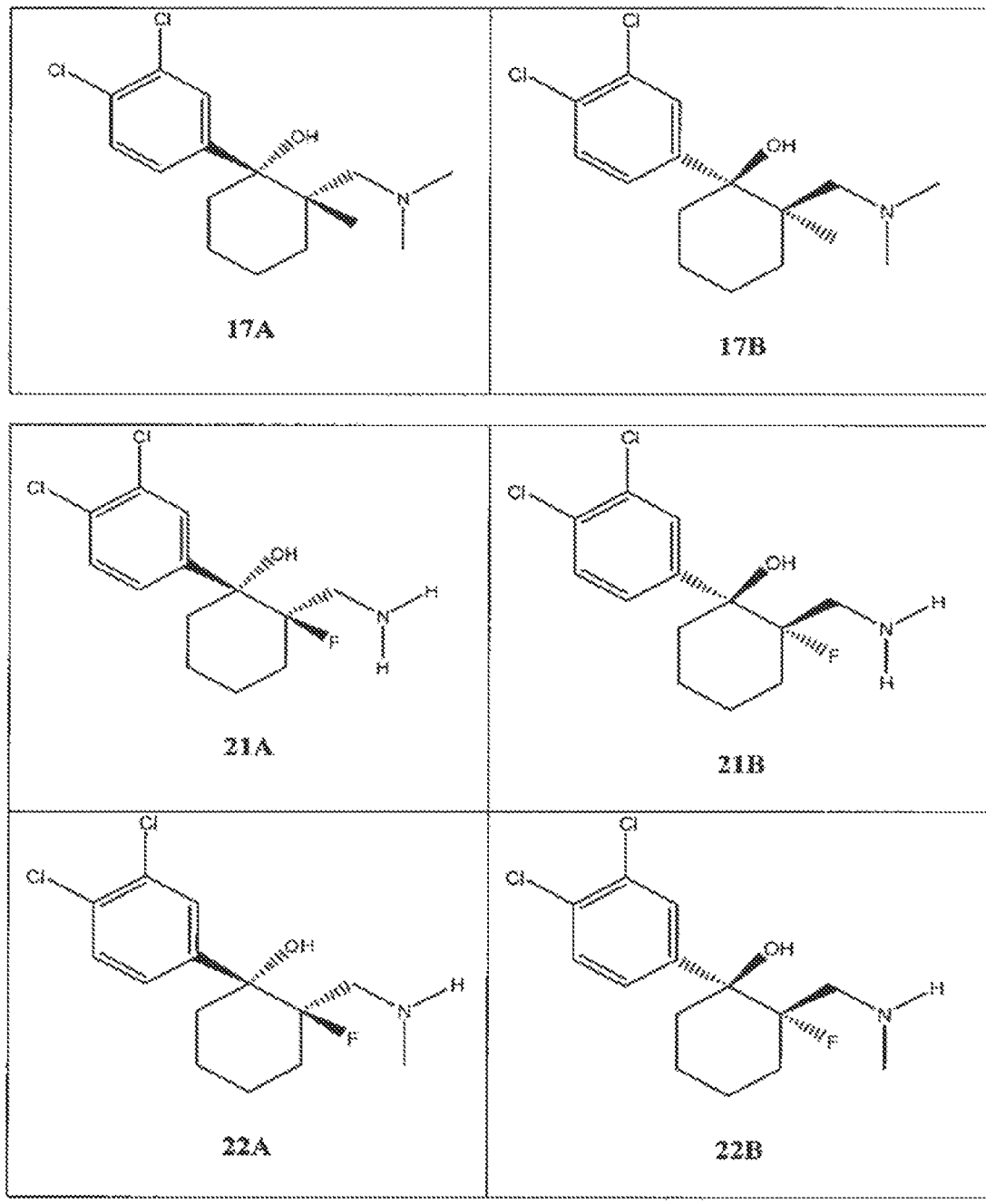
Figure 1D:
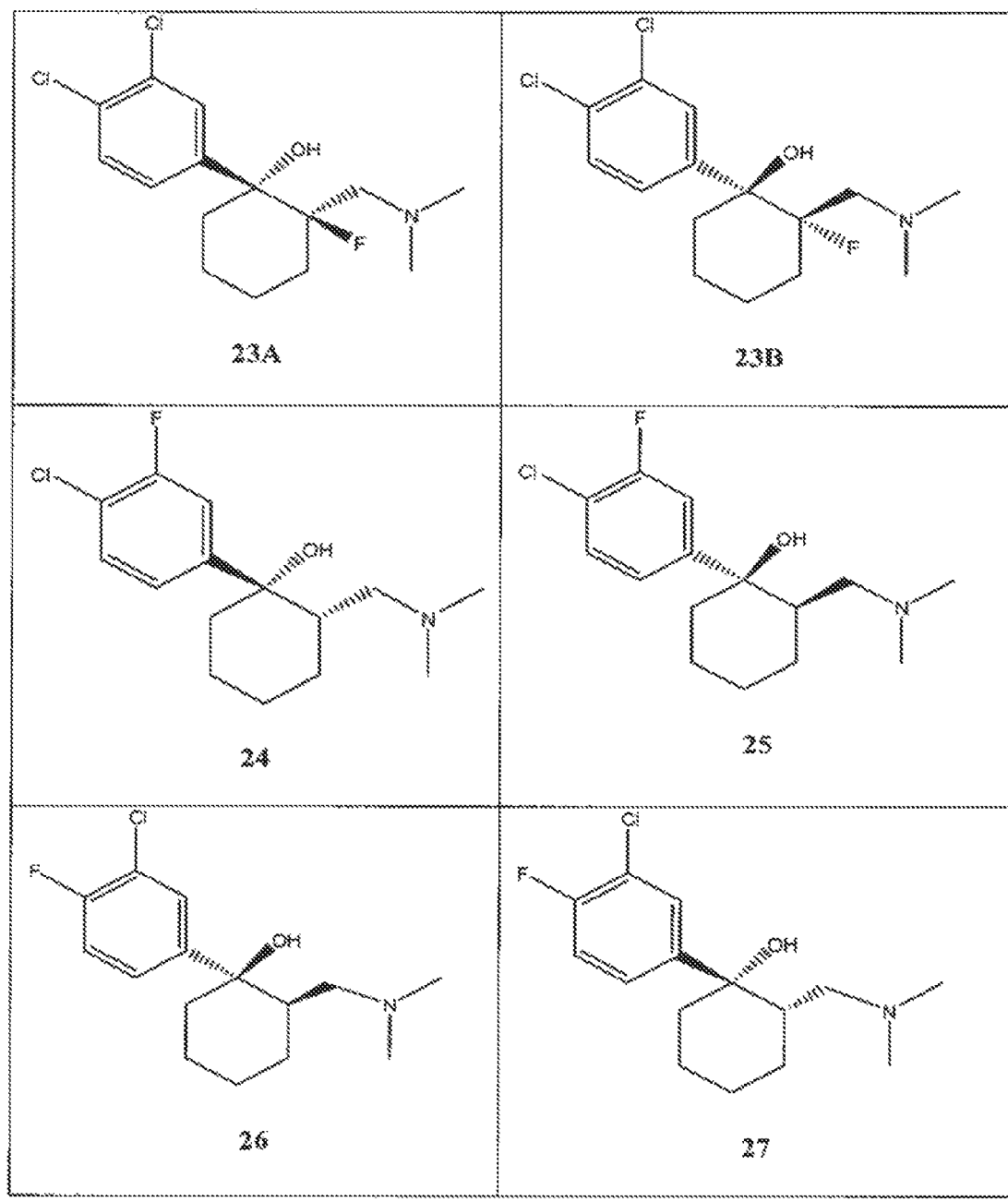
Figure 1E:
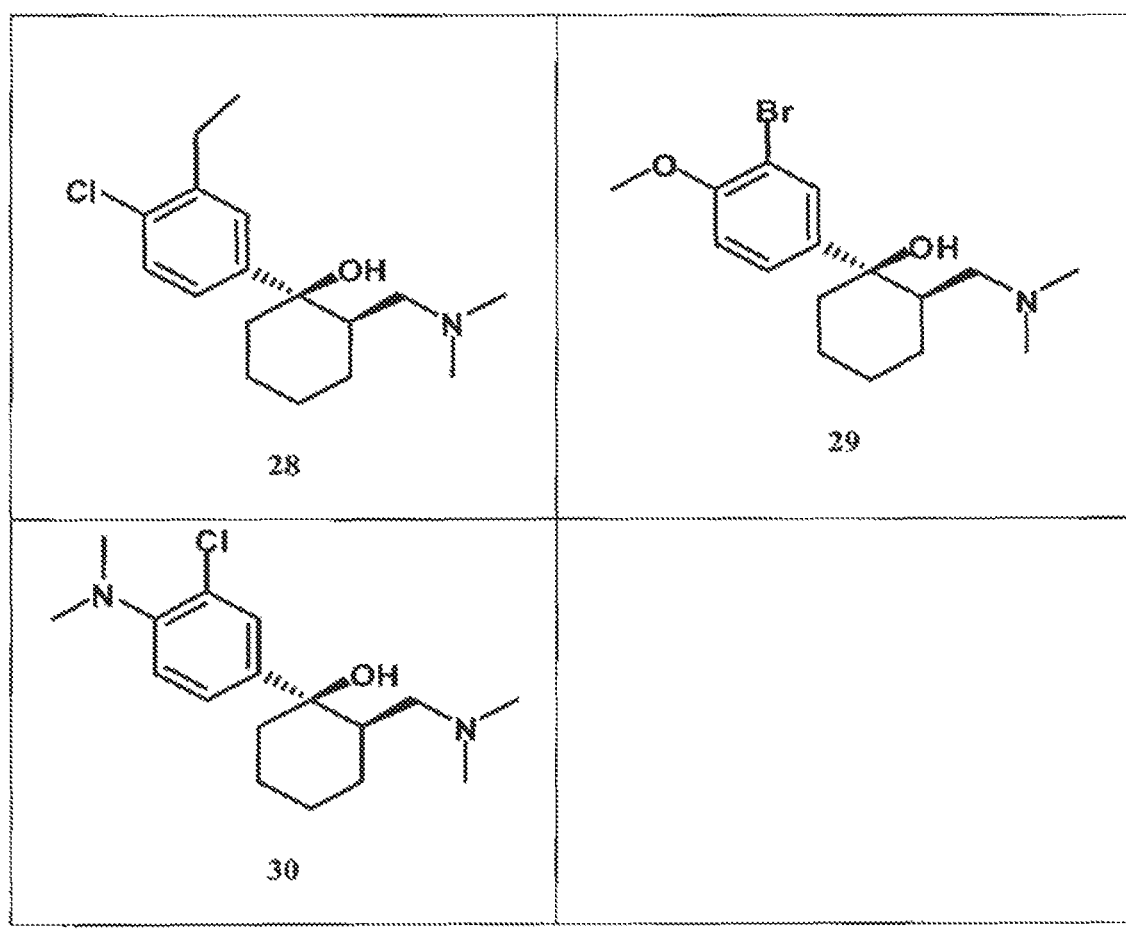

The term "alkyl," by itself or as part of another substituent, means, unless otherwise stated, a straight or branched chain, or cyclic hydrocarbon radical, or combination thereof, which may be fully saturated, unsaturated, e.g., mono- or polyunsaturated and can include di- and multivalent radicals. Alkyl radicals are optionally designated as having a number of carbons within a stated range—i.e., $C_1$-$C_{10}$ means a substituted or unsubstituted alkyl moiety having from one to ten carbons. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl; cyclic alkyl, e.g., cyclohexyl, (cyclohexyl) methyl, cyclopropylmethyl, fused ring species including, e.g., fused cycloalkyl (e.g., decalin) and the like. An unsaturated alkyl group is one having one or more double bonds or triple bonds, e.g., "alkenyl" and "alkynyl". Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl". Exemplary substituents found on "substituted alkyl" moieties are set forth below.

The term "alklyene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl" by itself or in combination with another term, means, unless otherwise stated, is a subgenus of "alkyl" as set forth above, a straight or branched chain, or cyclic alkyl radical, or combinations thereof, saturated or unsaturated alkyl radical consisting of a number of carbon atoms (optionally stated) and at least one heteroatom, preferably selected from B, O, N, P, Si and S, and wherein the nitrogen and sulfur atoms may optionally be oxidized and the nitrogen heteroatom may optionally be quaternized. The heteroatom(s) B, O, N, P, Si and S may be at any internal position of the heteroalkyl group or at the position at which the heteroalkyl group is attached to the remainder of the molecule, or at the antipodal terminus thereof. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Two or more heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2$R'— optionally represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" is mean to include, but not be limited to, tri-flouromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. "Aryl" species include structures that include aryl rings fused with cycloalkyl, heterocycloalkyl and heteroaryl rings. The term "heteroaryl" is subgeneric to "aryl" and refers to aryl groups that contain from one to four heteroatoms, preferably selected from B, O, N, P, Si and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used to define a substituent (e.g., aryloxy, arylthioxy, arylalkyl) optionally includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents" and they can be one or more of a variety of groups selected from, but not limited to: substituted or unsubstituted alkyl, substituted or unsubstituted heteroalkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —$NO_2$ in a number preferably ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_2$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted heteroalkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, flouro(C$_1$-C$_4$)alkoxy and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$-U-, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$-D-, wherein A and D are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X"—(CR"R'")$_d$—, where s and d are independently integers of from 0 to 3, and X" is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the terms "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic (i.e., aryl or heteroaryl) as well as saturated or unsaturated non aromatic rings (i.e., cycloalkyl heterocycloalkyl). Examples of "fused ring systems" are naphthalenes, indoles, quinolines, chromenes, decalin and the like.

As used herein, the term "heteroatom" includes oxygen (O), nitrogen (N), sulfur (S), silicon (Si), boron (B), and phosphorous (P).

The symbol "R" is a general abbreviate on that represents an "alkyl group substituent" or "aryl group substituent" (e.g., a substituent group that is selected from substituted or unsubstituted alkyl, substituted or unsubstituted heteroalkyl substituted or unsubstituted aryl, substituted or unsubstituted heteroaryl, and substituted or unsubstituted heterocycloalkyl groups).

The phrase "therapeutically effective amount" as used herein means that amount of a compound, or composition comprising a compound of the present invention which is effective for producing some desired therapeutic effect (e.g., by inhibiting uptake of a monoamine from the synaptic cleft of a mammal, thereby modulating the biological consequences of that pathway in the treated organism) at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in human beings and animals without excessive toxicity, irritation, allergic response, or other problem or complication, commensurate with a reasonable benefit/risk ratio.

The phrase "pharmaceutically acceptable carrier" as used herein means any pharmaceutically acceptable material, which may be liquid or solid. Exemplary carriers include vehicles, diluents, additives, liquid and solid fillers, excipients, solvents, solvent encapsulating materials. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, sulfamate, bisulfate, phosphate, nitrate, acetate, valerate, oleate, palmitate, stearate, laurate, benzoate, lactate, tosylate, citrate, maleate, ascorbate, palmitate, fumarate, succinate, tartrate, napthylate, mesylate, hydroxymaleate, phenylacetate, glutamate, glucoheptonate, salicyclate, sulfanilate, 2-acetoxybenzoate, methanesulfonate, ethane disulfonate, oxalate, isothionate, lactobionate, and laurylsulphonate salts and the like. See, for example, Berge et al. (1977) "Pharmaceutical Salts", J. Pharm. Sci. 66:1-19.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., Journal of Pharmaceutical Science, 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention. "Compound or a pharmaceutically acceptable salt or solvate of a compound" intends the inclusive meaning of "or", in that a material that is both a salt and a solvate is encompassed.

Certain compounds of the present invention possess asymmetric carbon atoms (optical centers) or double bonds; the racemates, diastereomers, geometric isomers and individual isomers are encompassed within the scope of the present invention. Optically active (R)- and (S)-isomers may be prepared using chiral synthons or chiral reagents, or resolved using conventional techniques. When the compounds described herein contain resolved double bonds or other centers of geometric asymmetry, and unless specified otherwise, it is intended that the compounds include both E and Z geometric isomers. Likewise, all tautomeric forms are also intended to be included.

The graphic representations of racemic, ambiscalemic and scalemic or enantiomerically pure compounds used herein are taken from Maehr, J. Chem. Ed., 62: 114-120 (1985); wavy lines indicate disavowal of any stereochemical implication which the bond it represents could generate; solid and broken wedges are geometric descriptors indicating the relative configuration shown but not implying any absolute stereochemistry; and wedge outlines and dotted or broken lines denote enantiomerically pure compounds of indeterminate absolute configuration.

The terms "enantiomeric excess" and "diastereomeric excess" are used interchangeably herein. Compounds with a single stereocenter are referred to as being present in "enantiomeric excess," those with at least two stereocenters are referred to as being present in "diastereomeric excess."

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "monoamine transporter ligand" refers to any compound, which binds to a monoamine transporter. Ligands include endogenous monoamines, which are the natural ligands for a given monoamine transporter as well as drug molecules and other compounds, such as synthetic molecules known to bind to a particular monoamine transporter. In one example, the ligand includes a radioisotope, such as tritium or is otherwise (e.g., fluorescently) labeled. It is within the abilities of the skilled person to select an appropriate ligand for a given monoamine transporter. For example, known ligands for the dopamine transporter include dopamine and WIN35428, known ligands for the serotonin transporter include 5-hydroxytryptamine (serotonin) and citalopram, and ligands for the norepinephrine transporter include norepinephrine and nisoxetine.

The term "eating disorder" refers to abnormal compulsions to avoid eating or uncontrollable impulses to consume abnormally large amounts of food. These disorders affect not only the social well-being, but also the physical well-being of sufferers. Examples of eating disorders include anorexia nervosa, bulimia, and binge eating.

The term "neurological disorder" refers to any condition of the central or peripheral nervous system of a mammal. The term "neurological disorder" includes neurodegenerative diseases (e.g., Alzheimer's disease, Parkinson's disease and amyotrophic lateral sclerosis), neuropsychiatric diseases (e.g. schizophrenia and anxieties, such as general anxiety disorder). Exemplary neurological disorders include MLS (cerebellar ataxia), Huntington's disease, Down syndrome, multi-infarct dementia, status epilecticus, contusive injuries (e.g. spinal cord injury and head injury), viral infection induced neurodegeneration, (e.g. AIDS, encephalopathies), epilepsy, benign forgetfulness, closed head injury, sleep disorders, depression, (e.g., bipolar disorder), dementias, movement disorders, psychoses, alcoholism, post-traumatic stress disorder and the like. "Neurological disorder" also includes any condition associated with the disorder. For instance, a method of treating a neurodegenerative disorder includes methods of treating loss of memory and/or loss of cognition associated with a neurodegenerative disorder. An exemplary method would also include treating or preventing loss of neuronal function characteristic of neurodegenerative disorder. "Neurological disorder" also includes any disease or condition that is implicated, at least in part, in monoamine (e.g., norepinephrine) signaling pathways (e.g., cardiovascular disease).

"Pain" is an unpleasant sensory and emotional experience. Pain classifications have been based on duration, etiology or pathophysiology, mechanism, intensity, and symptoms. The term "pain" as used herein refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain (see, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia.

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic pain" is a heterogeneous group of neurological conditions that result from damage to the nervous system. "Neuropathic" pain, as described above, refers to pain, resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Common types of peripheral neuropathic pain include diabetic neuropathy (also called diabetic peripheral neuropathic pain, or DN, DPN, or DPNP), post-herpetic neuralgia (PHN), and trigeminal neuralgia (TGN). Central neuropathic pain, involving damage to the brain or spinal cord, can occur following stroke, spinal cord injury, and as a result of multiple sclerosis. Other types of pain that are meant to be included in the definition of neuropathic pain include pain from neuropathic cancer pain, HIV/AIDS induced pain, phantom limb pain, and complex regional pain syndrome. In an exemplary embodiment, the compounds of the invention are of use for treating neuropathic pain.

Common clinical features of neuropathic pain include sensory loss, allodynia (non-noxious stimuli produce pain), hyperalgesia and hyperpathia (delayed perception, summation, and painful aftersensation). Pain is often a combination of nociceptive and neuropathic types, for example, mechanical spinal pain and radiculopathy or myelopathy.

"Acute pain", is the normal, predicted physiological response to a noxious chemical, thermal or mechanical stimulus typically associated with invasive procedures, trauma and disease. It is generally time-limited, and may be viewed as an appropriate response to a stimulus that threatens and/or produces tissue injury. "Acute pain", as described above, refers to pain which is marked by short duration or sudden onset.

"Chronic pain" occurs in a wide range of disorders, for example, trauma, malignancies and chronic inflammatory diseases such as rheumatoid arthritis. Chronic pain usually lasts more than about six months. In addition, the intensity of chronic pain may be disproportionate to the intensity of the noxious stimulus or underlying process. "Chronic pain", as described above, refers to pain associated with a chronic disorder, or pain that persists beyond resolution of an underlying disorder or healing of an injury, and that is often, more intense than the underlying process would predict. It may be subject to frequent recurrence.

"Inflammatory pain" is pain in response to tissue injury and the resulting inflammatory process. Inflammatory pain is adaptive in that it elicits physiologic responses that promote healing. However, inflammation may also affect neuronal function. Inflammatory mediators, including $PGE_2$ induced by the COX2 enzyme, bradykinins, and other substances, bind to receptors on pain-transmitting neurons and alter their function, increasing their excitability and thus increasing pain sensation. Much chronic pain has an inflammatory component. "Inflammatory pain", as described above, refers to pain which is produced as a symptom or a result of inflammation or an immune system disorder.

"Visceral pain", as described above, refers to pain which is located in an internal organ.

"Mixed etiology" pain, as described above, refers to pain that contains both inflammatory and neuropathic components.

"Dual mechanism" pain, as described above, refers to pain that is amplified and maintained by both peripheral and central sensitization.

"Causalgia" as described above, refers to a syndrome of sustained burning, allodynia, and hyperpathia after a traumatic nerve lesion, often combined with vasomotor and sudomotor dysfunction and later trophic changes.

"Central" pain, as described above, refers to pain initiated by a primary lesion or dysfunction in the central nervous system.

"Hyperesthesia" as described above, refers to increased sensitivity to stimulation, excluding the special senses.

"Hyperpathia", as described above, refers to a painful syndrome characterized by an abnormally painful reaction to a stimulus, especially a repetitive stimulus, as well as an increased threshold. It may occur with allodynia, hyperesthesia, hyperalgesia, or dysesthesia.

"Dysesthesia", as described above, refers to an unpleasant abnormal sensation, whether spontaneous or evoked. Special cases of dysesthesia include hyperalgesia and allodynia.

"Hyperalgesia", as described above, refers to an increased response to a stimulus that is normally painful. It reflects increased pain on suprathreshold stimulation.

"Allodynia", as described above, refers to pain due to a stimulus that does not normally provoke pain.

The term "pain" includes pain resulting from dysfunction of the nervous system: organic pain states that share clinical features of neuropathic pain and possible common pathophysiology mechanisms, but are not initiated by an identifiable lesion in any part of the nervous system.

The term "Diabetic Peripheral Neuropathic Pain" (DPNP, also called diabetic neuropathy, DN or diabetic peripheral neuropathy) refers to chronic pain caused by neuropathy associated with diabetes mellitus. The classic presentation of DPNP is pain or tingling in the feet that can be described not only as "burning" or "shooting" but also as severe aching pain. Less commonly, patients may describe the pain as itching, tearing, or like a toothache. The pain may be accompanied by allodynia and hyperalgesia and an absence of symptoms, suck as numbness.

The term "Post-Herpetic Neuralgia", also called "Postherpetic Neuralgia" (PHN) is a painful condition affecting nerve fibers and skin. It is a complication of shingles, a second outbreak of the varicella roster virus (VZV), which initially causes chickenpox.

The term "neuropathic cancer pain" refers to peripheral neuropathic pain as a result of cancer, and can be caused directly by infiltration or compression of a nerve by a tumor, or indirectly by cancer treatments such as radiation therapy and chemotherapy (chemotherapy-induced neuropathy).

The term "HIV/AIDS peripheral neuropathy" or "HIV/AIDS related neuropathy" refers to peripheral neuropathy caused by HIV/AIDS, such as acute or chronic inflammatory demyelinating neuropathy (AIDP and CIDP, respectively), as well as peripheral neuropathy resulting as a side effect of drugs used to treat HIV/AIDS.

The term "Phantom Limb Pain" refers to pain appearing to come from where an amputated limb used to be. Phantom limb pain can also occur in limbs following paralysis (e.g., following spinal cord injury). "Phantom Limb Pain" is usually chronic in nature.

The term "Trigeminal Neuralgia" (TN) refers to a disorder of the fifth cranial (trigeminal) nerve that causes episodes of intense, stabbing, electric-shock-like pain in the areas of the face where the branches of the nerve are distributed (lips, eyes, nose, scalp, forehead, upper jaw, and lower jaw). It is also known as the "suicide disease".

The term "Complex Regional Pain Syndrome (CRPS)," formerly known as Reflex Sympathetic Dystrophy (RSD), is a chronic pain condition. The key symptom of CRPS is continuous, intense pain out of proportion to the severity of the injury, which gets worse rather than better over time. CRPS is divided into type 1, which includes conditions caused by tissue injury other than peripheral nerve, and type 2, in which the syndrome is provoked by major nerve injury, and is sometimes called causalgia.

The term "Fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

The term "convulsion" refers to a neurological disorder acid is used interchangeably with "seizure," although there are many types of seizure, some of which have subtle or mild symptoms instead of convulsions. Seizures of all types may be caused by disorganized and sudden electrical activity in the brain. Convulsions are a rapid and uncontrollable shaking. During convulsions, the muscles contract and relax repeatedly.

The term "depression" includes all forms of depression, which include major depressive disorder (MDD), bipolar disorder, seasonal affective disorder (SAD) and dysthymia. "Major depressive disorder" is used herein interchangeably with "unipolar depression" and "major depression. "Depression" also includes any condition commonly associated with depression, such as all forms of fatigue (e.g., chronic fatigue syndrom) and cognitive deficits.

II. Introduction

One strategy to develop effective therapies for neurological disorders is the use of broad spectrum antidepressants that simultaneously inhibit the reuptake of more than one biogenic amine, such as serotonin (5-HT), norepinephrine (NE) and dopamine (DA). The rationale for this approach is based upon clinical and preclinical evidence showing that deficiencies in dopaminergic function can be correlated with anhedonia, which is a core symptom of depression. Baldessarini, R. J. "Drugs and the Treatment of Psychiatric Disorders: Depression and Mania, in Goodman and Gilman's The Pharmacological Basis of Therapeutics 431-459 ($9^{th}$ ed 1996) Hardman et al. eds.

An advantage of exemplary compounds and compositions of the present invention is their ability to increase availability of at least two neurotransmitters (e.g., NE, 5-HT and DA) by inhibiting their dual (re)uptake, e.g., from the synaptic cleft. Skolnick and coworkers report on a body of preclinical evidence suggesting that the therapeutic profile of an antidepressant concurrently increasing the synaptic availability of DA, NE and 5-HT will differ from a compound inhibiting only NE and/or 5-HT. Skolnick, P. et al., "Antidepressant-like actions of DOV-21,947: a "triple" reuptake inhibitor, "*Eur. J. Pharm.* 2003, 461, 103.

For example, Skolnick and coworkers have reported that a compound, DOV 21,947 ((+)-1-(3,4-dichlorophenyl)-3-azabicyclo[3.1.0]hexane), inhibits the reuptake of serotonin, norepinephrine, and dopamine in human embryonic kidney (HEK293) cells expressing the corresponding human recombinant transporters ($IC_{50}$ values of 12, 23 and 96 nM, respectively). Skolnick, P. et al., "Antidepressant-like actions of DOV-21,947: a "triple" reuptake inhibitor," *Eur. J. Pharm.* 2003, 461, 99. In addition, DOV 21,947 reduces the duration of immobility in the forced swim test (in rats) and also produces a dose-dependent reduction in immobility in the tail suspension test. Additional evidence can be found in preclinical data for new triple reuptake inhibitors such as DOV 21,947 in, e.g., U.S. Pat. No. 6,372,919, wherein DOV 21,947 was disclosed as having a significantly greater affinity for the norepinephrine and serotonin uptake sites than the racemic compound, (±)-1-(3,4-dichlorophenyl)-3-azabicyclo[3.1.0]hexane.

Taken together, the preclinical data for compounds such as DOV 21,947 indicate that dual or triple reuptake inhibitors hold potential as novel treatments for depression in the clinic.

III. Compositions

A. Cycloalkyl Amines

In an exemplary embodiment, the invention provides a compound having the formula:

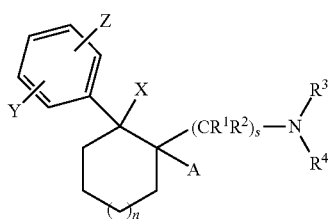

wherein the index n is an integer selected from the group consisting of 0, 1, and 2; and s is an integer selected from the group consisting of 0, 1 and 2. A is a member selected from H, substituted or unsubstituted alkyl, halogen and substituted or unsubstituted haloalkyl. X is selected from H, halogen, substituted or unsubstituted alkyl, substituted or unsubstituted aryl, substituted or unsubstituted haloalkyl and $OR^5$, in which $R^5$ is selected from H, substituted or unsubstituted alkyl, substituted or unsubstituted heteroalkyl, substituted or unsubstituted aryl, substituted or unsubstituted heteroaryl, acyl and $S(O)_2R^{5a}$, in which $R^{5a}$ is selected from substituted or unsubstituted alkyl, substituted or unsubstituted heteroalkyl, substituted or unsubstituted aryl, substituted or unsubstituted heteroaryl and substituted or unsubstituted heterocycloalkyl.

Y and Z independently represent H, halogen, $CF_3$, CN, $OR^9$, $SR^9$, substituted or unsubstituted alkyl, substituted or unsubstituted heteroalkyl, substituted or unsubstituted aryl, substituted or unsubstituted heteroaryl, substituted or unsubstituted heterocycloalkyl, $NR^{10}R^{11}$ or $NO_2$. Y and Z, together with the atoms to which they are attached, are optionally joined to form a 5- to 7-membered ring, which can optionally have 1, 2 or 3 heteroatoms therein. $R^9$ represents H, substituted or unsubstituted alkyl, substituted or unsubstituted heteroalkyl, substituted or unsubstituted aryl, substituted or unsubstituted heteroaryl, or substituted or unsubstituted heterocycloalkyl. The radicals $R^{10}$ and $R^{11}$ independently represent H, $OR^{12}$, acyl, $S(O)_2R^{13}$, substituted or unsubstituted alkyl, substituted or unsubstituted heteroalkyl, substituted or unsubstituted aryl, substituted or unsubstituted heteroaryl or substituted or unsubstituted heterocycloalkyl. $R^{10}$ and $R^{11}$, together with the nitrogen to which they are attached, are optionally joined to form a 3-, 4-, 5- 6- or 7-membered ring, optionally having 1, 2 or 3 heteroatoms in addition to the nitrogen to which $R^{10}$ and $R^{11}$ are joined. The symbol $R^{12}$ represents H, substituted or unsubstituted alkyl, substituted or unsubstituted heteroalkyl, substituted or unsubstituted aryl, substituted or unsubstituted heteroaryl or substituted or unsubstituted heterocycloalkyl. $R^{13}$ is selected from substituted or unsubstituted alkyl, substituted or unsubstituted heteroalkyl, substituted or unsubstituted aryl, substituted or unsubstituted heteroaryl and substituted or unsubstituted heterocycloalkyl.

$R^1$ and $R^2$ are independently H, halogen, CN, $CF_3$, $OR^6$, substituted or unsubstituted alkyl, substituted or unsubstituted heteroalkyl, substituted or unsubstituted aryl, substituted or unsubstituted heteroaryl or substituted or unsubstituted heterocycloalkyl. $R^6$ is selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

$R^3$ and $R^4$ independently represent H, $OR^7$, acyl, $S(O)_2R^8$, substituted or unsubstituted alkyl, substituted or unsubstituted heteroalkyl, substituted or unsubstituted aryl, substituted or unsubstituted heteroaryl or unsubstituted heterocycloalkyl. $R^7$ is H, substituted or unsubstituted alkyl, substituted or unsubstituted heteroalkyl, substituted or unsubstituted aryl, substituted or unsubstituted heteroaryl or substituted or unsubstituted heterocycloalkyl. $R^8$ is a member selected from substituted or unsubstituted alkyl, substituted or unsubstituted heteroalkyl, substituted or unsubstituted aryl, substituted or unsubstituted heteroaryl and substituted or unsubstituted heterocycloalkyl.

Two or more of $R^1$, $R^2$, $R^3$ and $R^4$, together with the atoms to which they are attached, are optionally joined to form a 3-, 4-, 5-, 6- or 7-membered ring, which optionally includes 1, 2, 3 or 4 heteroatoms.

Y and Z, together with the atoms to which they are attached, are optionally joined to form a 5-, 6- or 7-membered ring, which can optionally have 1, 2 or 3 heteroatoms therein. As will be apparent to those of skill in the art, when Y and Z are joined into a ring, the substituents (e.g., $R^9$, $R^{10}$ and $R^{11}$) on atoms incorporated into the ring will be present (e.g., incorporated into the cyclic structure of the ring) or absent as necessary to satisfy the valence of the atom to which these substituents are attacked.

In an exemplary embodiments Y and Z independently represent halogen, $CF_3$, CN, $OR^9$, substituted or unsubstituted alkyl, substituted or unsubstituted heteroalkyl, substituted or unsubstituted aryl, substituted or unsubstituted heteroaryl, substituted or unsubstituted heterocycloalkyl, $NR^{10}R^{11}$ and $NO_2$. Y and Z, together with the atoms to which they are attached, are optionally joined to form a 5-, 6- or 7-membered ring, which can optionally have 1, 2 or 3 heteroatoms therein.

In an exemplary embodiment, the compound of the invention does not have a structure according to the following formulae:

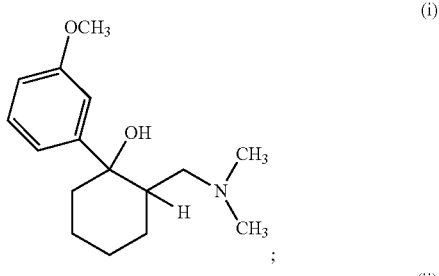

(i)

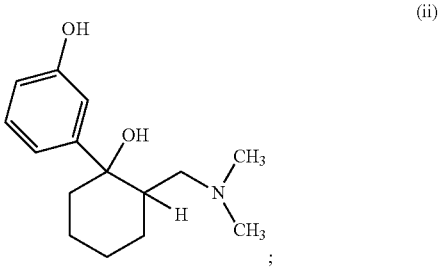

(ii)

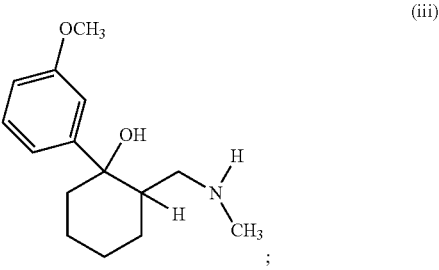

(iii)

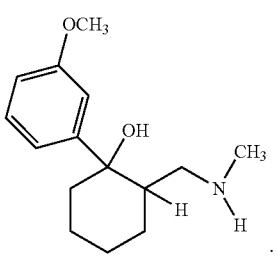
(iv)
;

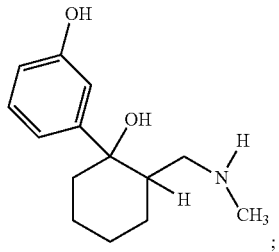
(v)
;

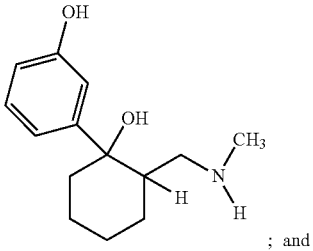
(vi)
; and

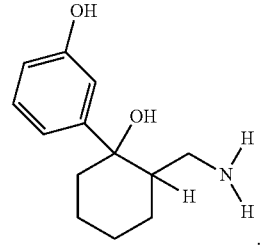
(vii)
.

In another exemplary embodiment, the compound does not have a structure according to the following formula:

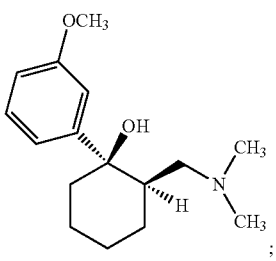
(viii)
;

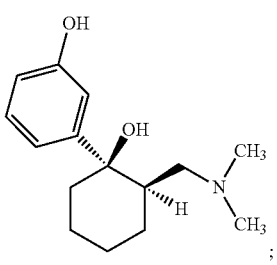
(ix)
;

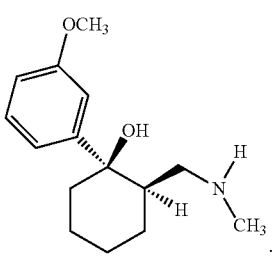
(x)
;

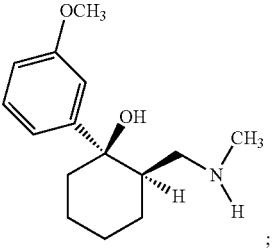
(xi)
;

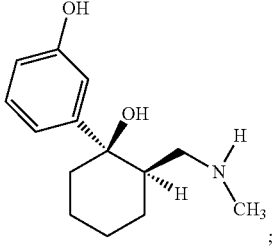
(xii)
;

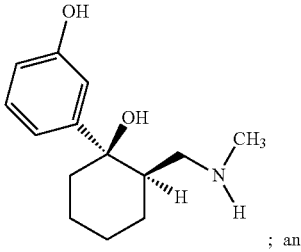
(xiii)
; and

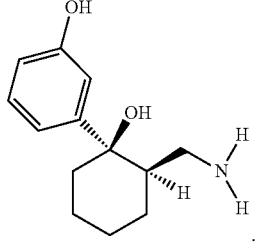
(xiv)
.

In an exemplary embodiment, the compound has a structure such that when either Y or Z is H, then $R^9$ is other than a member selected from H and substituted or unsubstituted alkyl. In an exemplary embodiment, the compound has a structure such that when either Y or Z is H, then $R^9$ is other than a member selected from H and unsubstituted alkyl. In an exemplary embodiment, the compound has a structure such that when either Y or Z is H, then $R^9$ is other than a member selected from H, methyl and ethyl.

In an exemplary embodiment, the compound has a structure such that $R^5$ is other than a member selected from H and substituted or unsubstituted alkyl. In an exemplary embodiment, the compound has a structure such that $R^5$ is other than a member selected from H and unsubstituted alkyl. In an exemplary embodiment, the compound has a structure such that $R^5$ is other than a member selected from H, methyl and ethyl.

In various exemplary embodiments, the index s is 1. In an exemplary embodiment, the index n is 1. In various embodiments, both s and n are 1.

In an exemplary embodiment, Y and Z are independently selected from H, halogen, CN and $CF_3$. In various embodiments, at least one of Y and Z is other than H. In exemplary embodiments, both Y and Z are other than H.

In an exemplary embodiment, $R^3$ and $R^4$ are members independently selected from substituted or unsubstituted $C_1$-$C_4$ alkyl and substituted or unsubstituted $C_1$-$C_4$ heteroalkyl. In an exemplary embodiment, $R^3$ and $R^4$ are members independently selected from the group consisting of substituted or unsubstituted alkenyl, substituted or unsubstituted alkynyl and substituted or unsubstituted cycloalkyl.

In various embodiments, the compounds of the invention have a structure which is a member selected from the group consisting of:

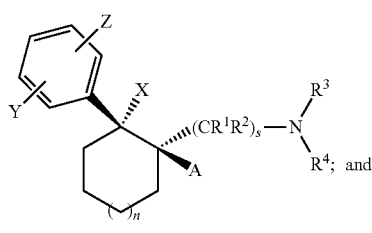

(Ia)

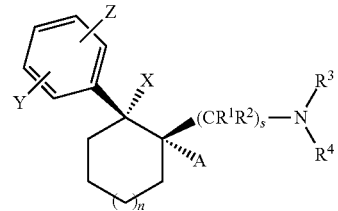

(Ib)

In selected embodiments, the compounds of the invention have a structure selected from Formulae II and IIa:

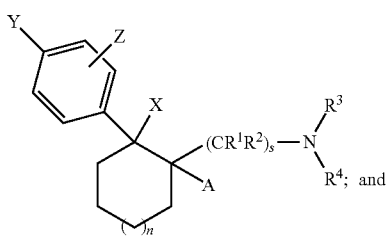

(II)

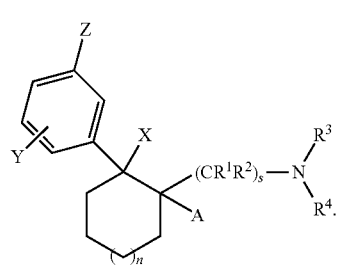

(IIa)

Exemplary compounds according to Formulae II and IIa include:

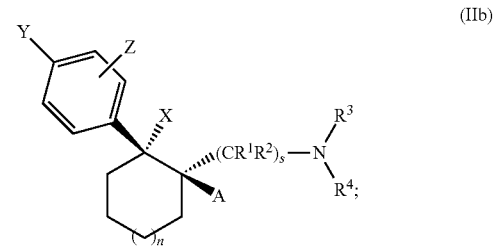

(IIb)

(IIc)

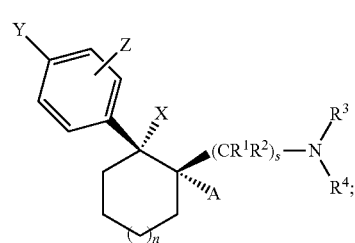

(IIf)

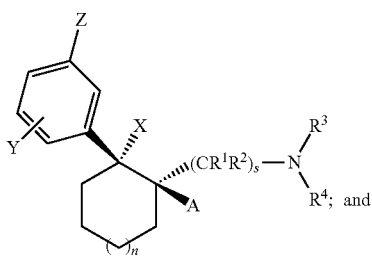

(IIg)

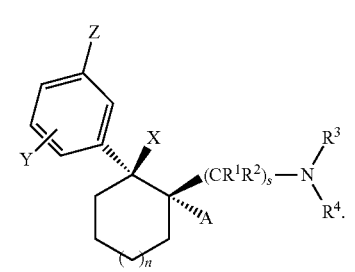

In an exemplary embodiment, Y and Z are members independently selected from the group consisting of H, halogent, CN and $CF_3$. In an exemplary embodiment, Y and Z are halogen. In an exemplary embodiment, Y and Z are chloro. In an exemplary embodiment, s is 1. In an exemplary embodiment, n is 1. In an exemplary embodiment, $R^1$ and $R^2$ are H. In an exemplary embodiment, A is H. In another exemplary embodiment, $R^1$ and $R^2$ are H, and A is H.

In selected embodiments, the compounds of the invention have a structure selected from Formulae III and IIIa:

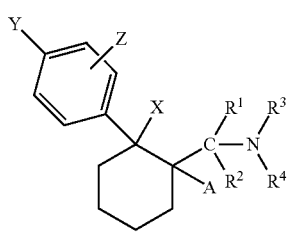

(III)

Exemplary compounds according to Formulae III and IIIa, include:

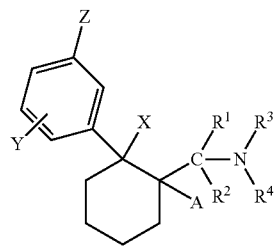
(IIIa)

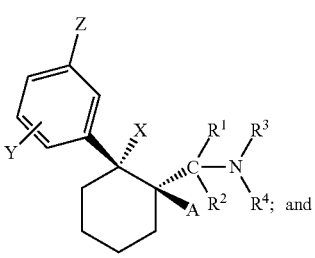
(IIIb)

(IIIc)

(IIIf)

(IIIg)

In an exemplary embodiment, Y and Z are members independently selected from the group consisting of H, halogen, CN and $CF_3$. In an exemplary embodiment, Y and Z are halogen. In an exemplary embodiment, Y and Z are chloro. In an exemplary embodiment, s is 1. In an exemplary embodiment, n is 1. In an exemplary embodiment, $R^1$ and $R^2$ are H. In an exemplary embodiment, A is H. In another exemplary embodiment, $R^1$ and $R^2$ are H, and A is H.

In an exemplary embodiment, the compound has a structure according to Formula (IV):

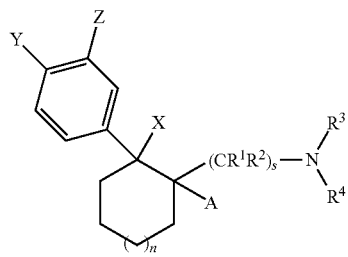
(IV)

wherein Y and Z are independently selected halogens. In an exemplary embodiment, the compounds have a structure according to:

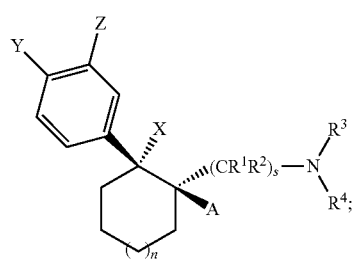
(IVa)

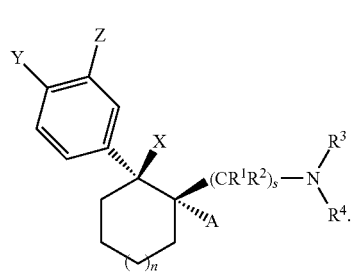
(IVb)

In an exemplary embodiment, the compounds have a structure according to:

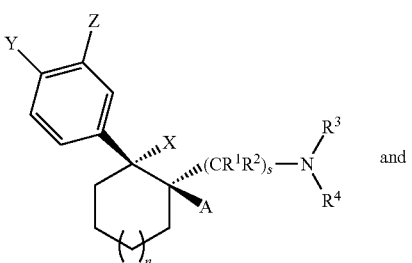
(IVa)

and

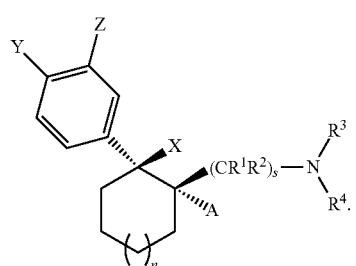
(IVb)

In another embodiment, Y is a member selected from F and Cl. In another embodiment, Z is a member selected from F and Cl. In another embodiment, Y is Cl and Z is Cl. In another embodiment, Y is F and Z is Cl. In another embodiment, Y is Cl and Z is F.

In an exemplary embodiment, the compound has a structure according to Formula (V):

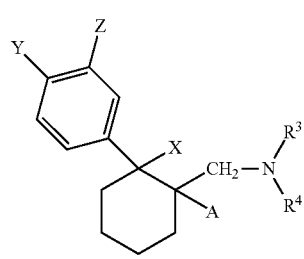
(V)

wherein Y and Z are independently selected halogens. In an exemplary embodiment, the compounds have a structure according to:

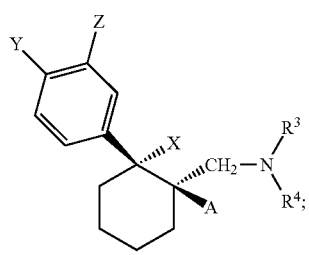
(Va)

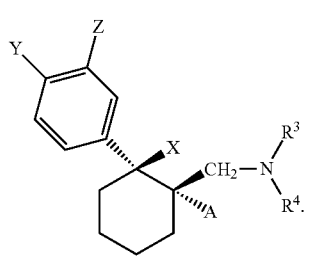
(Vb)

In an exemplary embodiment, the compounds have a structure according to:

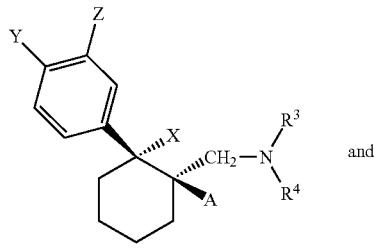
(Va)

and

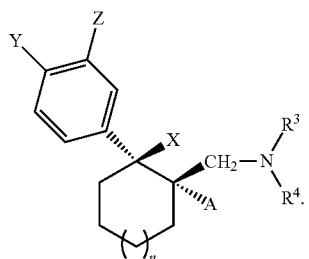
(Vb)

In another embodiment, Y is a member selected from F and Cl. In another embodiment, Z is a member selected from F and Cl. In another embodiment Y is Cl and Z is Cl. In another embodiment, Y is F and Z is Cl. In another embodiment, Y is Cl and Z is F.

An exemplary compound of the invention has the formula:

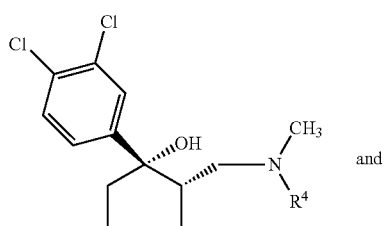
(Ve)

and

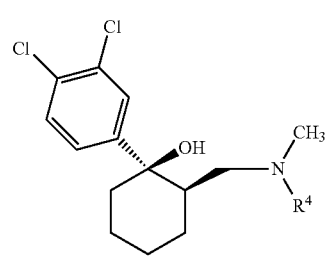
(Vf)

in which $R^4$ is either H or $CH_3$.

In an exemplary embodiment, the compound has a structure according to Formula (VI):

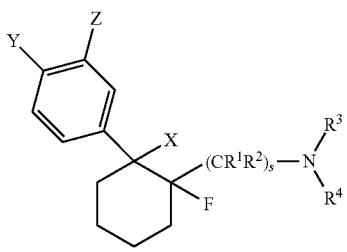
(VI)

In another exemplary embodiment, the compound having this structure has at least one member selected from Y and Z which is a halogen. In another exemplary embodiment, Y and Z are halogen. In another embodiment, Y is a member selected from F and Cl. In another embodiment, Z is a member selected from F and Cl. In another embodiment, Y is Cl and Z is Cl. In another embodiment, Y is F and Z is Cl. In another embodiment, Y is Cl and Z is F.

In an exemplary embodiment, the compound has a structure according to Formula (VII):

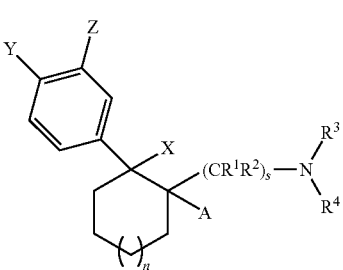
(VII)

wherein Y and Z are not H and A is a member selected from substituted or unsubstituted alkyl. In another exemplary embodiment, the compound having this structure has at least one member selected from Y and Z which is a halogen. In another exemplary embodiment, Y and Z are halogen. In another embodiment, Y is a member selected from F and Cl. In another embodiment, Z is a member selected from F and Cl. In another embodiment, Y is Cl and Z is Cl. In another embodiment, Y is F and Z is Cl. In another embodiment, Y is Cl and Z is F. In an exemplary embodiment, A is substituted or unsubstituted methyl. In an exemplary embodiment, A is methyl.

In an exemplary embodiment, the compound has a structure according to Formula (VIII):

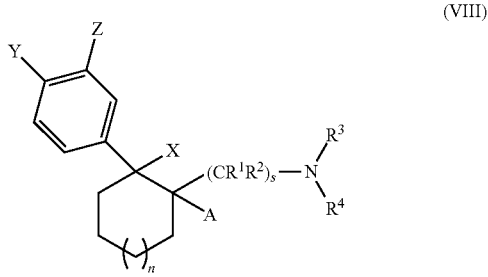

(VIII)

wherein Y and Z are not H and $R^3$ and $R^4$ are each independently selected from H and substituted or unsubstituted alkyl. In another exemplary embodiment, $R^3$ and $R^4$ are each independently selected from H and substituted or unsubstituted methyl. In another exemplary embodiment, $R^3$ and $R^4$ are each independently selected from H and methyl. In another exemplary embodiment, the compound having this structure has at least one member selected from Y and Z which is a halogen. In another exemplary embodiment, Y and Z are halogen. In another embodiment, Y is a member selected from F and Cl. In another embodiment, Z is a member selected from F and Cl. In another embodiment, Y is Cl and Z is Cl. In another embodiment, Y is F and Z is Cl. In another embodiment, Y is Cl and Z is F.

Exemplary compounds of the invention have a structure according to the following formulae:

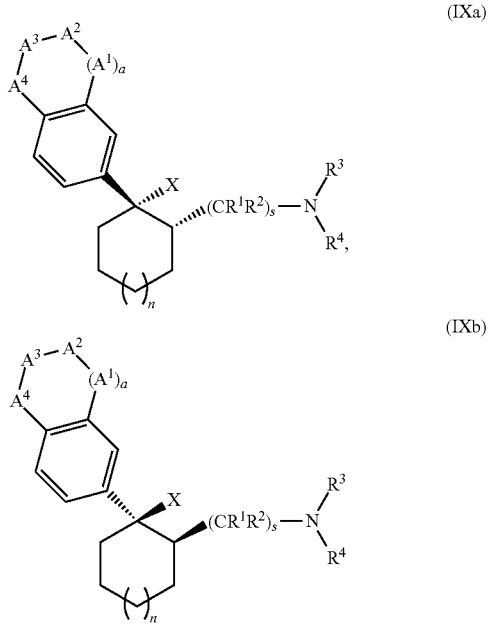

(IXa)

(IXb)

in which $A^1$, $A^2$, $A^3$ and $A^4$ are each independently selected from O, S, $N(R^b)_b$, and $C(R^b)_b(R^c)$. The index a is an integer selected from 0, 1 and 2. The index b is 0 or 1 as needed to satisfy the valence requirements of the atom to which it is attached. $R^b$ and $R^c$ are members independently selected from H, halogen, $CF_3$, CN, $OR^{14}$, $SR^{14}$, $NR^{15}R^{16}$, $NR^{15}S(O)_2R^{14}$, $NR^{15}C(O)R^{14}$, $S(O)_2R^{14}$, acyl, $C(O)OR^{14}$, $C(O)NR^{15}R^{16}$, $S(O)_2NR^{15}R^{16}$, substituted or unsubstituted alkyl, substituted or unsubstituted heteroalkyl, substituted or unsubstituted aryl, substituted or unsubstituted heteroaryl and substituted or unsubstituted heterocycloalkyl. Each $R^{14}$, $R^{15}$ and $R^{16}$ is a member independently selected from the group consisting of H, acyl, substituted or unsubstituted alkyl, substituted or unsubstituted heteroalkyl, substituted or unsubstituted aryl, substituted or unsubstituted heteroaryl, substituted or unsubstituted heterocycloalkyl, wherein two of $R^{14}$, $R^{15}$ and $R^{16}$ together with the atoms to which they are attached, are optionally joined to form a 3-, 4-, 5-, 6- or 7-membered ring, which optionally includes 1, 2 or 3 heteroatoms.

In an exemplary embodiment, $R^b$ and $R^c$ are members independently selected from the group consisting of H, halogen, CN, halogen substituted $C_1$-$C_4$ alkyl (e.g., $CF_3$) and $C_1$-$C_4$ alkoxy (e.g., OMe, OEt, $OCF_3$).

In an exemplary embodiment, Y and Z are joined to form a fused ring system having 5, 6 or 7 members and, optionally including 1, 2 or 3 heteroatoms. Hence, in one embodiment, the phenyl ring substituent has the structure:

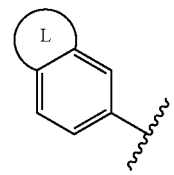 [SMILES: *c1ccccc1]

in which, ring L is substituted or unsubstituted, saturated or unsaturated cycloalkyl or heterocycloalkyl, or it is substituted or unsubstituted aryl or heteroaryl.

An exemplary fused ring structure is:

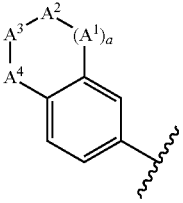

in which $A^1$, $A^2$, $A^3$ and $A^4$ and a are described herein.

The compounds of the invention include an amine moiety (e.g., a primary, secondary or tertiary amino group) and as such can be converted into a salt form by contacting the compound (e.g., the free base) with an acid. In an exemplary embodiment, the salt form is generated to convert an otherwise oily or viscous compound into a solid substance for easier handling. In another exemplary embodiment, converting the free base of a compound of the invention into a corresponding salt increases solubility of the compound in aqueous media, winch can effect biological characteristics, such as bioavailability, pharmacokinetics and pharmacodynamics. Hence, any salt forms, such as pharmaceutically acceptable salts, including salts of inorganic acids (e.g., hydrochloride salts) or organic acids, of the compounds of the invention are within the scope of the current invention. Also within the scope of the invention are any prodrugs of the compounds of the invention. For example, $R^3$ and $R^4$ can be any group, which is cleavable in vivo to result in an amine, e.g., a primary or secondary amine.

B. Compositions Including Stereoisomers

The compound of the invention can include one or more stereocenter and may exist in particular geometric or stereoisomeric form's. Compounds can be chiral, racemic or be present in a composition including one or more stereoisomer. The current invention encompasses enantiomers, diastereomers, racemic mixtures, enantiomerically enriched mixtures, and diastereomerically enriched mixture. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivatization with a chiral auxiliary, where the resulting diastereomeric mixture is separated and the auxiliary group cleaved to provide the pure desired enantiomers. Alternatively, where the molecule contains basic functional group, such as an amino group, or an acidic functional group, such as a carboxyl group, diastereomeric salts may be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

As used herein, the term, "enantiomerically enriched" or "diastereomerically enriched" refers to a compound having an enantiomeric excess (ee) or a diastereomeric excess (de) greater than about 50%, preferably greater than about 70% and more preferably greater than about 90%. In general, higher than about 90% enantiomeric or diastereomeric purity is particularly preferred, e.g., those compositions with greater than about 95%, greater than about 97% and greater than about 99% ee or de.

The terms "enantiomeric excess" and "diastereomeric excess" are used interchangeably herein. Compounds with a single stereocenter are referred to as being present in "enantiomeric excess"; those with at least two stereocenters are referred to as being present in "diastereomeric excess".

For example, the term "enantiomeric excess" is well known in the art and is defined as:

$$ee_a = \left(\frac{conc.\ of\ a - conc.\ of\ b}{conc.\ of\ a + conc.\ of\ b}\right) \times 100$$

The term "enantiomeric excess" is related to the older term "optical purity" in that both are measures of the same phenomenon. The value of ee will be a number from 0 to 100, zero being racemic and 100 being enantiomerically pure. A compound which in the past might have been called 98% optically pure is now more precisely characterized by 96% ee. A 90% ee reflects the presence of 95% of one enantiomer and 5% of the other(s) in the material in question.

Hence, in one embodiment, the invention provides a composition including a first stereoisomer and at least one additional stereoisomer of a compound of the invention. The first stereoisomer may be present in a diastereomeric or enantiomeric excess of at least about 80%, preferably at least about 90% and more preferably at least about 95%. In a particularly preferred embodiment, the first stereoisomer is present in a diastereomeric or enantiomeric excess of at least about 96%, at least about 97%, at least about 98%, at least about 99% or at least about 99.5%. Enantiomeric or diastereomeric excess may be determined relative to exactly one other stereoisomer, or may be determined relative to the sum of at least two other stereoisomers. In an exemplary embodiment, enantiomeric or diastereomeric excess is determined relative to all other detectable stereoisomers, which are present in the mixture. Stereoisomers are detectable if a concentration of such stereoisomer in the analyzed mixture can be determined using common analytical methods, such as chiral HPLC.

C. Synthesis of the Compounds

1. General

Compounds of the invention may be synthesized as pure cis isomers or a racemic mixture, or a mixture of two or more diastereomers. Stereoisomers may be separated at an appropriate synthetic stage, for example, by chiral column chromatography, such as HPLC to give enantiomerically/diastereomerically enriched or enantiomerically or diastereomerically pure forms of the respective stereoisomers. Stereochemical assignments may be made on the basis of NMR coupling patterns optionally in conjunction with literature values. Absolute configurations can be determined by synthesis from chiral precursor of known configuration, or by X-ray crystallographic determination using crystallized materials.

Stereochemical-configurations are defined according to the relative configuration of the amine-bearing side chain and the substituent on the cycloalkyl ring. When more than one substituent is present, the higher order (IUPAC) substituent is used for the determination of stereochemical-configuration.

Compounds of the invention may be synthesized according to the schemes set forth below, it is within the abilities of a person skilled in the art to select appropriate alternative reagents replacing the exemplary reagents shown in the schemes in order to synthesize a desired compound of the invention. It is also within the abilities of a skilled artisan to omit or add synthetic steps when necessary.

2. General Synthesis of Cycloalkylamines

In one embodiment, the compounds of the Invention were synthesized from the corresponding amino ketone a as shown in Scheme 1, below.

Scheme 1: Exemplary Synthesis of Cycloalkylamines from Ketones

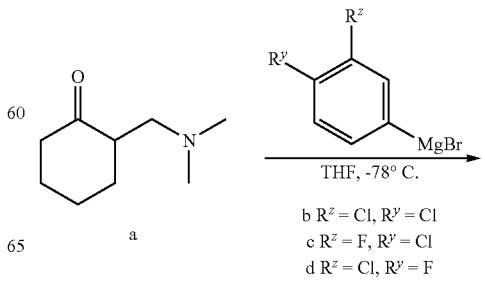

b $R^z$ = Cl, $R^y$ = Cl
c $R^z$ = F, $R^y$ = Cl
d $R^z$ = Cl, $R^y$ = F

31

-continued

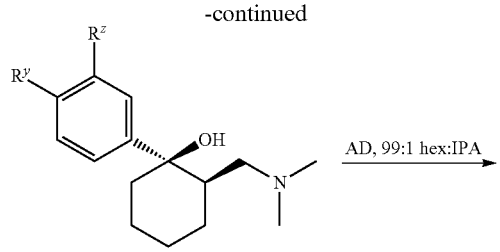

+/- e $R^z$ = Cl, $R^y$ = Cl
+/- f $R^z$ = F, $R^y$ = Cl
+/- g $R^z$ = Cl, $R^y$ = F

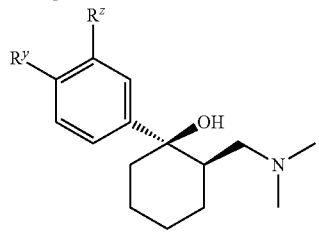

1 $R^z$ = Cl, $R^y$ = Cl
24 $R^z$ = F, $R^y$ = Cl
26 $R^z$ = Cl, $R^y$ = F

32

-continued

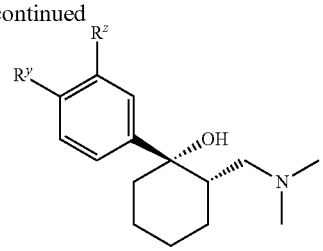

2 $R^z$ = Cl, $R^y$ = Cl
25 $R^z$ = F, $R^y$ = Cl
27 $R^z$ = Cl, $R^y$ = F

Dimethylaminomethyl cyclohexanone a was condensed with aryl Grignard reagents b-d to give racemic amino alcohols. The racemic products were purified by chiral chromatography on a semi-preparative chiralpak AD column to give enantiomers 1, 24 and 28, and 2, 26 and 27. In addition to the values of $R^y$ and $R^z$ disclosed in Scheme 1, $R^y$ and $R^z$ are members independently selected from substituted or unsubstituted alkyl, Cl, Br, P, $NR^{10}R^{11}$, $OR^9$, $SR^9$ and substituted or unsubstituted aryl.

Scheme 2: Exemplary Resolution and Derivatization of Cycloalkylamines
All absolute configurations arbitrarily assigned

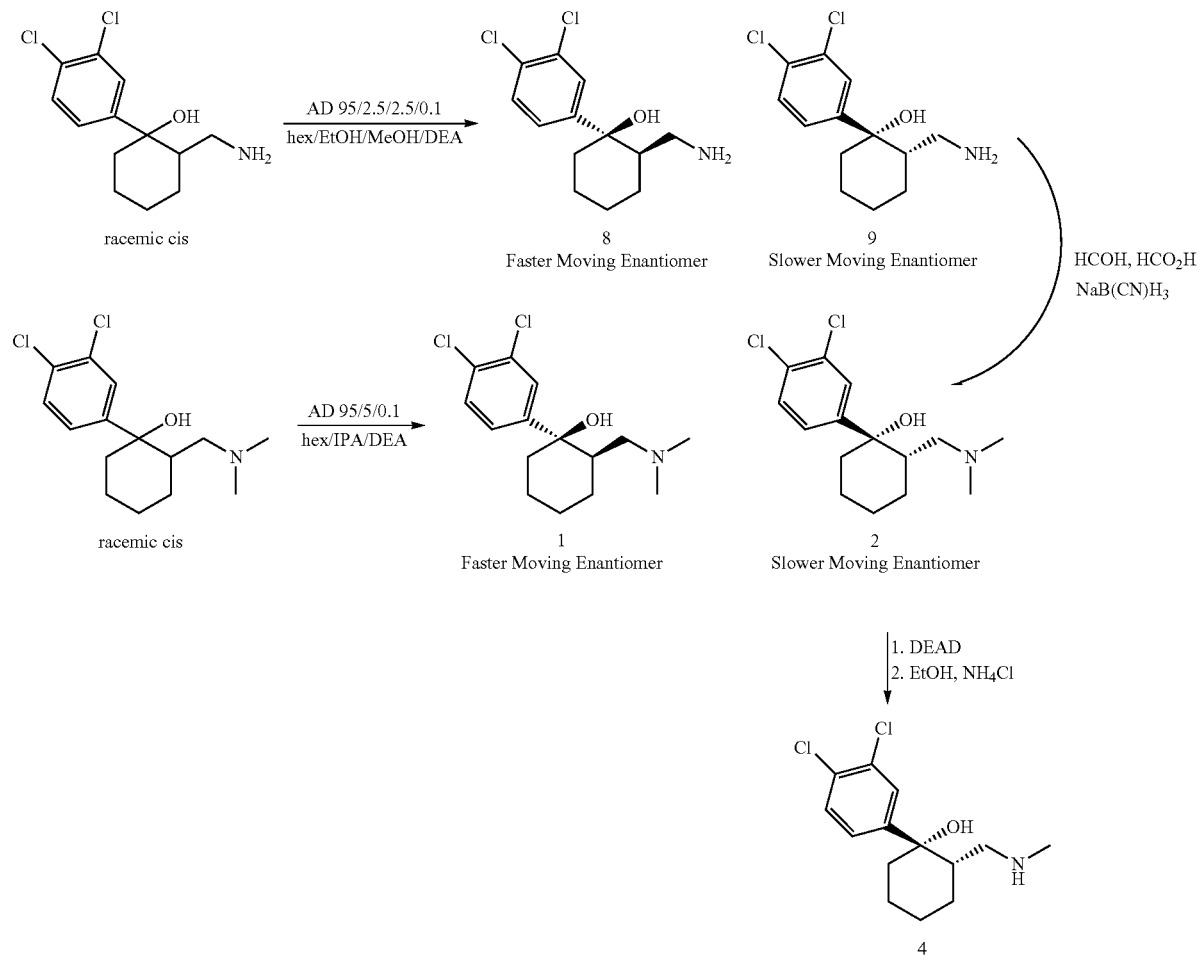

Referring to Scheme 2, the parent primary amine for 2, compound 9, was obtained via chiral HPLC separation of racemic cis-3-(aminomethyl)-1-(3,4-dichlorophenyl)cyclohexanol into constitutive isomers 8 (faster moving enantiomer) and 9 (slower moving enantiomer). 9 was converted to 2 via reductive animation with formic acid, formaldehyde and sodium cyanoborohydride 2 was also obtained as the slower moving enantiomer after chiral HPLC separation of racemic cis-1-(3,4-dichlorophenyl)-2-((dimethylamino)methyl)cyclohexanol; reduction of 2 in a two step procedure with DEAD and acidic EtOH provided mono-methyl derivative 4.

D. Pharmaceutical Compositions

In an exemplary aspect, the invention provides a pharmaceutical composition including a compound described herein or a pharmaceutically acceptable salt or solvate thereof, and at least one pharmaceutically acceptable carrier. In various embodiments, the compound is a cis isomer. In an exemplary embodiment, the compound has a structure which is a member selected from Formulae (I) to (IX).

As described in detail below, the pharmaceutical compositions of the present invention may be specially formulated for administration in solid or liquid form, including those adapted for oral administration, e.g., tablets, drenches (aqueous or non-aqueous solutions or suspensions), parenteral, administration, (including intravenous and intramuscular), or epidural injection as, for example, a sterile solution or suspension, or sustained release formulation. The pharmaceutical compositions of the present invention may also be specifically formulated for administration transdermally.

The pharmaceutical compositions of the invention may be administered orally, parenterally, subcutaneously, transdermally, nasally, or by anal suppository. The pharmaceutical compositions of the invention may also be administered using controlled delivery devices.

Formulations of the present invention include those suitable for oral and parenteral administration, particularly intramuscular, intravenous and subcutaneous administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect, without being toxic to the patient. Generally, out of one hundred percent, this amount will range from about 1 percent to about ninety-nine percent of active ingredient.

Exemplary unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose (in single or divided doses) ranges from about 1 mg per day to about 7000 mg per day, preferably about 1 mg per day to about 100 mg per day, and more preferably, from about 10 mg per day to about 100 mg per day, and even more preferably from about 20 mg to about 100 mg, to about 80 mg or to about 60 mg. In some embodiments, the total daily dose may range from about 50 mg to about 500 mg per day, and preferably, about 100 mg to about 500 mg per day. It is further recommended that children, patients over 65 years old, and those with impaired renal or hepatic function, initially receive low doses and that the dosage be titrated based on individual responses and/or blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, caplets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a compound of the present invention as an active ingredient. A compound of the present invention may also be administered as a bolus, electuary or paste.

In solid dosage forms of the invention for oral administration (capsules, tablets, caplets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, sialic acid and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium, stearate, magnesium stearate, solid polyethylene glycols, sodium lauryl sulfate, and mixtures thereof and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally, with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known. In the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention, include water, ethanol, polyols (such as glycerol, propylene glycol, polyethylene glycol, and the like), and suitable mixtures thereof, vegetable oils, such as olive oil and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. Pharmaceutical compositions or unit dosage forms of the present invention in the form of prolonged-action tablets may comprise compressed tablets formulated to release the drug substance in a manner in provide medication over a period of time. There are a number of tablet types that include delayed-action tablets in which the release of the drug substance is prevented for an interval of time after administration or until certain physiological conditions exist. Repeat action tablets may be formed that periodically release a complete dose of the drug substance to the gastrointestinal fluids. Also, extended release tablets that continuously release increments of the contained drug substance to the gastrointestinal fluids may be formed.

Compounds of the invention can be also administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the compounds of this invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side e.g., adverse) effects.

Most controller-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Compounds of the present invention may also be formulated as transdermal, topical, and mucosal dosage forms, which forms include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed. Lea & Febiger, Philadelphia (1985). Transdermal dosage forms include "reservoir type" or "matrix type" patches, which can be applied to the skin and worn for a specific period of time to penult the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers can be used to assist in delivering the active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

When the compounds of the present invention are administered as pharmaceuticals, to humans and animals, they can be given per se or as a pharmaceutical composition, containing, for example, 0.1 to 99.5% of active ingredient in combination with a pharmaceutically acceptable carrier.

The preparations of the present invention may be given orally and parenterally. They are of course given in forms suitable for each administration route. For example, they are administered in tablets or capsule form, by injection, and by intravenous administration. In one embodiment, oral administrations are preferred.

The phrases "parenteral administration" and "administered parenterally" as used herein means modes of administration other than enteral and topical, administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian, having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.005 mg per kilogram to about 5 mg per kilogram of body weight per day. In an exemplary embodiment, the oral dose of a compound of the invention will range from about 10 mg to about 300 mg per day. In an exemplary embodiment, the oral dose of a compound of the invention will range from about 20 mg to about 250 mg per day. In an exemplary embodiment, the oral dose of a compound of the invention will range from about 100 mg to about 300 mg per day. In an exemplary embodiment, the oral dose of a compound of the invention will range from about 10 mg to about 100 mg per day. In an exemplary embodiment, the oral dose of a compound of the invention will range from about 25 mg to about 50 mg per day. In an exemplary embodiment, the oral dose of a compound of the invention will range from about 50 mg to about 200 mg per day. Bach of the above-recited dosage ranges may be formulated as a unit dosage formulation.

The terms "treatment" or "treating" is intended to encompass therapy, preventing relapse, and amelioration of acute symptoms. Note that "treating" refers to either or both of the amelioration of symptoms and the resolution of the underlying condition. In many of the conditions of the invention, the administration of a compound or composition of the invention may act not directly on the disease state, but rather on some pernicious symptom, and the improvement of that symptom leads to a general and desirable amelioration of the disease state. The compounds of the invention can also be used to prevent a disease (prophylaxis).

The patient receiving this treatment is any animal in need, including primates, in particular humans, and other mammals such as equines, cattle, swine and sheep, as well as poultry and pets in general.

The compounds and pharmaceutical compositions of the invention can be administered in conjunction with other pharmaceutical agents, for instance antimicrobial agents, such as penicillins, cephalosporins, aminoglycosides and glycopeptides. Conjunctive therapy thus includes sequential, simultaneous and separate administration of the active compound in a way that the therapeutic effects of the first administered agent have not entirely disappeared when the subsequent agent is administered.

In an exemplary embodiment, the subject exhibiting an indication for which a compound of the invention is therapeutically efficacious is not otherwise in need of treatment with a compound of the invention or a compound falling within the structural genus encompassing the compounds of the invention.

IV. Methods

A. Binding to Monoamine Transporter

In various aspects the invention provides a method of binding a compound of the invention to a monoamine transporter. The method includes contacting the monoamine transporter and a compound of the invention.

The invention further provides a method of inhibiting binding of a monoamine transporter ligand to a monoamine transporter (such as serotonin transporter, dopamine transporter and norepinephrine transporter). The method includes contacting the monoamine transporter and a compound of the invention. In an exemplary embodiment the monoamine transporter ligand is an endogenous monoamine, such as serotonin, dopamine or norepinephrine. In another exemplary embodiment the ligand is a drug molecule or another small molecule known to have binding affinity to a monoamine transporter. In another exemplary embodiment, the monoamine transporter ligand is a radioactively labeled compound, known to bind to the monoamine transporter.

In an exemplary embodiment, inhibition of ligand binding is shown using an ex vivo binding assay, such as those described herein. In an exemplary embodiment, the compound of the invention. Inhibits mean binding by between about 1% and about 100%, preferably by between about 10% and about 100%, more preferably by between about 20% and about 90% when compared to vehicle. Inhibition of mean binding is preferably dose dependent.

B. Inhibition of Monoamine Transporter Activity

In various embodiments, the invention provides a method of modulating (e.g., inhibiting, augmenting) the activity of at least one monoamine transporter, such as serotonin transporter, dopamine transporter and norepinephrine transporter. The method includes contacting the monoamine transporter and a compound of the invention. In an exemplary embodiment, the monoamine transporter is contacted with a compound of the invention, by administering to a subject a therapeutically effective amount of the compound of the invention, or a pharmaceutically acceptable salt or solvate thereof. The subject can be a human. In an exemplary embodiment, the monoamine transporter is dopamine transporter (DAT), serotonin transporter (SERT) or norepinephrine transporter (NET). In various exemplary embodiments, the compound of the invention inhibits the activity of at least two different monoamine transporters. Inhibition of monoamine transporter activity may be measured using assays known in the art. Exemplary assay formats include in vitro functional uptake assays. In an exemplary embodiment, the functional uptake assay utilizes an appropriate cell-line expressing a desired monoamine transporter. In various exemplary embodiments, the functional uptake assay utilizes synaptosomes isolated from brain tissue of an appropriate organism. Alternatively, inhibition of monoamine transporter activity may be assessed using receptor binding experiments known in the art, e.g., utilizing appropriate membrane preparations. An exemplary assay involves treatment of a test subject (e.g., a rat) with a compound of the invention as well as a reference compound, followed by isolation of brain tissue and ex vivo analysis of receptor occupancy, as described herein.

C. Inhibition of Monoamine Uptake

In various aspects, the invention provides a method of inhibiting uptake of at least one monoamine (e.g., dopamine, serotonin, norepinephrine) by a cell. The method includes contacting the cell with a compound of the invention. In an exemplary embodiment, the cell is a brain cell, such as a neuron or a glial cell. In one example, inhibition of monoamine uptake occurs in vivo. In an organism, neuronal uptake (also termed reuptake) of a monoamine such as dopamine or serotonin occurs, for example, from the synaptic cleft. Thus, in one embodiment, the neuronal cell is in contact with a synaptic cleft of a mammal. In another exemplary embodiment, inhibition of monoamine uptake occurs in vitro. In those methods the cell, may be a brain cell, such as a neuronal cell or a cell-type, which expresses a recombinant monoamine transporter.

In one embodiment, the compound inhibits uptake of at least two different monoamines. This can, for example, be shown by performing various in vitro functional uptake assays utilizing a cell-type, which simultaneously expresses multiple different monoamine transporters (such as isolated synaptosomes), or may be shown by using two different cell types, each expressing a different monoamine transporter, such as a recombinant dopamine transporter, together with an appropriate, labeled monoamine. Inhibition of monoamine uptake is demonstrated when the inhibitor (e.g., a compound of the invention) has an $IC_{50}$ of between about 0.1 nM and about 10 µM, preferably between about 1 nM and about 1 µM, more preferably between about 1 nM and about 500 nM, and even more preferably between about 1 nM and about 100 nM in a functional monoamine uptake assay, such as those described herein below.

D. Treatment of Neurological Disorders

In another aspect, the invention provides a method of treating a neurological disorder by inhibiting the activity at least one monoamine transporter. The method includes administering to a subject in need thereof a therapeutically effective amount of a composition or compound of the invention, or a pharmaceutically acceptable salt or solvate thereof. In an exemplary embodiment, the mammalian subject is a human. In another exemplary embodiment, the compound of the invention inhibits the activity of at least two different monoamine transporters. For example, the compound of the invention inhibits the activity of at least two of serotonin transporter, dopamine transporter and norepinephrine transporter. Inhibition of monoamine transporter activity may be shown by functional monoamine uptake assays as described herein below.

Demonstration of compound activity can be performed in various art-recognized animal models. For example, anti-depressant activity of a compound of the invention may be shown by utilizing an appropriate animal model of depression, such as the Rat Forced Swim Test, the Mouse Tail Suspension Test and Rat Locomotor Activity Analyses. The Rat Forced Swim Test is also suitable for the analysis of compounds having activities against more than one monoamine transporter (mixed monoamine transporter activity). For example, an increase in swimming activity is indicative of serotonin reuptake inhibition, while an increase in climbing activity is indicative of norepinephrine reuptake inhibition.

In an various embodiments, the compounds of the invention are active in at least one animal model, which can be used to measure the activity of the compounds and estimate their efficacy in treating a neuroligal disorder. For example, when the animal model is for depression (e.g., mean immobility), the compounds of the invention are active when they inhibit mean immobility by between about 5% and about 90%, preferably between about 10% and about 70% more preferably between about 10% and about 50%, more preferably between about 15% and about 50% in at least one animal model, when compared to vehicle. In various embodiments, the compounds of the invention produce a similar disparity in measured endpoint between treated animals and animals administered vehicle.

In various embodiments, the invention provides a method of effecting an anti-depressant-like effect. The method includes administering to a mammalian subject in need thereof a therapeutically effective amount of a compound or composition of the invention, or a pharmaceutically acceptable salt or solvate thereof. Anti-depressant-like effects may be measured using an animal model of disease, such as those described herein.

In various exemplary embodiments, the neurological disorder is a member selected from the group consisting of depression (e.g., major depressive disorder, bipolar disorder, unipolar disorder, dysthymia and seasonal affective disorder), cognitive deficits, fibromyalgia, pain (e.g., neuropathic pain), sleep related disorders (e.g., sleep apnea, insomnia, narcolepsy, cataplexy) including those sleep disorders, which are produced by psychiatric conditions, chronic fatigue syndrome, attention deficit disorder (ADD), attention deficit hyperactivity disorder (ADHD), restless leg syndrome, schizophrenia, anxieties (e.g. general anxiety disorder, social anxiety disorder, panic disorder), obsessive compulsive disorder, posttraumatic stress disorder, seasonal affective disorder (SAD), premenstrual dysphoria, postmenopausal vasomotor symptoms (e.g., hot flashes, night sweats), and neurodegenerative disease (e.g., Parkinson's disease, Alzheimer's disease and amyotrophic lateral sclerosis), manic conditions, dysthymic disorder, cyclothymic disorder, obesity and substance abuse or dependency (e.g., cocaine addiction, nicotine addiction). In an exemplary embodiment, the neurological disorder is depression, such as major depressive disorder. In an exemplary embodiment, the compounds of the invention are useful to treat two conditions/disorders, which are comorbid, such as cognitive deficit and depression.

Neurological disorder includes cerebral function disorders, including without limitation, senile dementia, Alzheimer's type dementia, cognition, memory loss, amnesia/amnestic syndrome, epilepsy, disturbances of consciousness, coma, lowering of attention, speech disorders, Lennox syndrome, autism, and hyperkinetic syndrome.

Neuropathic pain includes without limitation post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use).

Other exemplary diseases and conditions that may be treated using the methods of the invention include obesity; migraine or migraine headache; urinary incontinence, including without limitation involuntary voiding of urine, dribbling or leakage of urine, stress urinary incontinence (SUI), urge incontinence, urinary exertional incontinence, reflex incontinence, passive incontinence, and overflow incontinence; as well as sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psycho-sexual dysfunction, including without limitation, inhibited sexual desire, inhibited sexual excitement, inhibited female orgasm, inhibited male orgasm, functional dyspareunia, functional vaginismus, and atypical psychosexual dysfunction.

In an exemplary embodiment, the neurological disorder is obesity, and the therapeutically effective amount of compound to supply to a patient is enough so that said patient feels satiated.

In an exemplary embodiment, the compounds described herein treat/prevent a central nervous disorder, without causing addiction to said compounds.

The following examples are provided to illustrate the exemplary features of the invention.

EXAMPLES

The following examples are provided to illustrate selected embodiments of the invention and are not to be construed as limiting its scope.

Example 1

1a. General Procedures

In the examples, below, the following general experimental procedures were used unless otherwise noted: All commercial reagents were used without further purification. Anhydrous reactions were performed in flame-dried glassware under $N_2$. NMR spectra were recorded on a Varian 400 MHz spectrometer in deuterochloroform or methanol-$d^4$ with trimethylsilane (TMS) as an internal reference. Silica gel column chromatography was performed using an ISCO Combiflash system with detection at 254 nm or using ISCO normal phase silica gel cartridges.

1b. Analytical HPLC

Analytical HPLC was performed on a Hewlett Packard Series 1100 pump connected to an Agilent Zorbax RX-C18 5 µm, 4.6×250 mm column, with detection on a Hewlett Packard Series 1100 UV/Vis detector monitoring at 214 and 254 nm. Typical flow rate=1 ml/mm. Three different HPLC columns and various elution protocols were used. For example, (1) Agilent Zorbax RX-C18 5 µm, 4.6×250 mm column running a linear gradient. Solvent A=$H_2O$ w/0.05% TFA, Solvent B=MeCN w/0.05% TFA, Time 0 min=5% Solvent B, time 4 min=40% Solvent B, time 8 min=100% Solvent B, 12 min=5% Solvent B, 20 min=5% Solvent B; (2) Phenomenex 3µ C18 column running a 3 minute gradient of 5→100% B (acetonitrile/0.1% formic acid) and solvent A (water/0.1% formic acid); (3) Phenomenex 5µ C18 column running a 5 minute gradient of 5→100% B where solvent B (acetonitrile/0.1% formic acid) and solvent A (water/0.1% formic acid).

1c. Reverse Phase HPLC Implication

Reverse phase HPLC purification was performed on a Gibson system using a Phenomenex 5μ C18 (50×21.2 mm) column. The standard separation method was: 10 minute gradient of 10→100% B (acetonitrile/0.1% formic acid) in solvent A (water/0.1% formic acid). Crude samples were typically dissolved in MeOH. Fractions were concentrated by Genovac (centrifugation at low pressure).

1d. GC-MS

Gas chromatography was performed on a Hewlett Packard 6890 Series GC System with an HP1 column (30 meters, 0.15μ film thickness) couples to a Hewlett Packard 5973 Series Mass Selective Detector. The following linear temperature gradient was used: 100° C. for 5 minutes, then 20° C./min to 320° C. Hold@320° C. for 10 minutes.

1e. LCMS

LCMS was performed on an Agilent 1100 Series system connected to a Micromass Platform LC. The following column and gradient was used: Column: Luna C18(2), 3 um particle size 30×2.0 mm column dimension. Flow rate=0.5 mL/min, Solvent A=0.1 M NH$_4$Ac in 95% H$_2$O, 5% MeOH, pH 6.0, Solvent B=Solvent B: 0.1 M NH$_4$Ac in MeOH. Linear gradient with 6 entries: Time 0 min=100% Solvent A, time 10 min=100% Solvent B, time 12 min=100% Solvent B, time 12 min 10 sec=100% Solvent A, time 14 min=100% Solvent A, time 14 min 20 sec=100%. Solvent A.

1f. Microwave (μW) Recrystallization

The crude salt (e.g., HCl salt) was loaded into a microwave vessel with a stir bar. The recrystallization solvent was added and the vessel was heated at the target temperature for a given time. The vessel was cooled to 50° C. in the reactor, was then removed and allowed to slowly cool to RT. N,N-dimethyl amines were typically recrystallized in EtOAc or EtOAc:CH$_3$CN (2:1). N—Me or primary amines were typically recrystallized in CH$_3$CN.

Example 2

2a. Experimental Procedures and Characterization Data

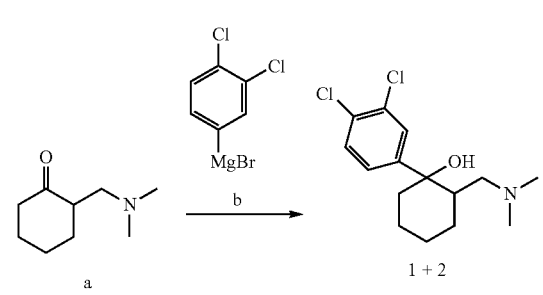

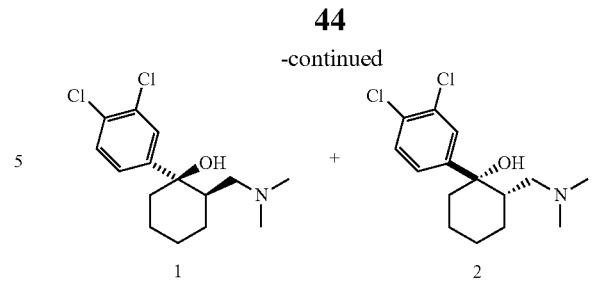

To a solution of ketone a (2.0 g, 13 mmol) in THF (20 mL) at −78° C. was added 3,4-dichlorophenylmagnisium bromide (0.5 M in THF, 38 mL, 19 mmol). The reaction mixture was stirred for 30 mm at −78° C. before being warmed to 0° C. over 30 min. A saturated solution of NH$_4$Cl (30 mL) was added to the reaction mixture to quench the reaction. The resulting product was extracted with diethyl ether (2×100 mL). The combined extracts were dried and concentrated. The residue was subjected to silica gel column chromatography (ethyl acetate/hexane/Et$_3$N=1:10:0.1) to give the racemic mixture of 1 and 2 (3.5 g, 90%). The racemic mixture was separated by chiral AD column (hexane/iPrOH/DEA=95/5/0.1 as eluent) to give pure 1 (Faster moving enantiomer) and 2 (Slower moving enantiomer).

2a1. Data For 1/2

$^1$H NMR (400 MHz, CD$_3$OD) δ 7.73 (d, J=1.6 Hz, 1H), 7.52 (d, J=8.4 Hz, 1H), 7.47 (dd, J=1.6, 8.4 Hz, 1H), 3.01 (dd, J=13.2, 10.4 Hz, 1H), 2.76 (s, 3H), 2.65 (s, 3H), 2.57 (dd, J=2.0, 13.2 Hz, 1H), 2.28 (m, 2H), 1.9 (m, 2H), 1.70 (m, 2H), 1.6 (m, 2H); $^{13}$C NMR (100 MHz, CD$_3$OD) δ 148.86, 132.32, 130.32, 127.49, 125.08, 74.11, 60.22, 45.03, 41.22, 40.29, 25.71, 24.64, 21.16; ESI MS m/z 302.1, 304.0.

2. Dealkylation of Cycloalkyamines

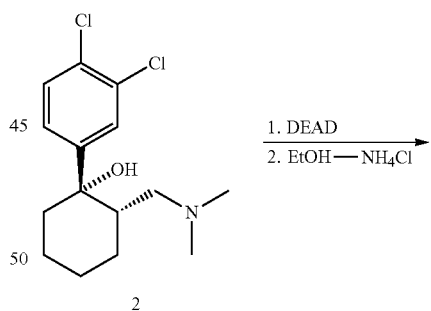

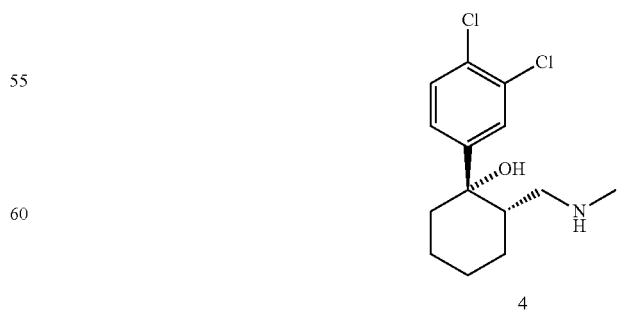

To a solution of 2 (0.8 g, 2.65 mmol) in toluene was added DEAD (0.69 g, 0.63 mL, 3.90 mmol). The reaction mixture was heated at 100° C. for 4 h before being concentrated. The residue was dissolved in 30 mL of EtOH and a saturated solution of NH₄Cl (30 mL) was added. The reaction mixture was stirred at 50° C. for 6 h before being concentrated. NaOH solution (2 M, 10 mL) was added to the resulting mixture and the product was extracted with diethyl ether (2×80 mL). The combined extracts were dried and concentrated. The residue was purified by reserve phase column chromatography (CH₃CN/H₂O=5/95 to 95/5) to give 4 (0.32 g, 42%).

2b1. Data for 4

$^1$H NMR (400 MHz, CD$_3$OD) δ 7.60 (s, 1H), 7.37 (m, 2H), 2.57 (dd, J=2.0, 12.4 Hz, 1H), 2.28 (dd, J=2.8, 12.4 Hz, 1H), 2.23 (s, 3H), 1.88 (m, 2H), 1.78 (m, 2H), 1.62 (m, 1H), 1.56 (m, 2H), 1.40 (m, 1H); $^{13}$C NMR (100 MHz, CD$_3$OD) δ 150.86, 132.40, 130.21, 130.09, 127.56, 124.77, 77.03, 53.54, 43.95, 40.82, 36.81, 26.45, 26.05, 22.05; ESI MS m/z 288.1.

2c. Synthesis of Cyclohexylamines from Cyclohexanone

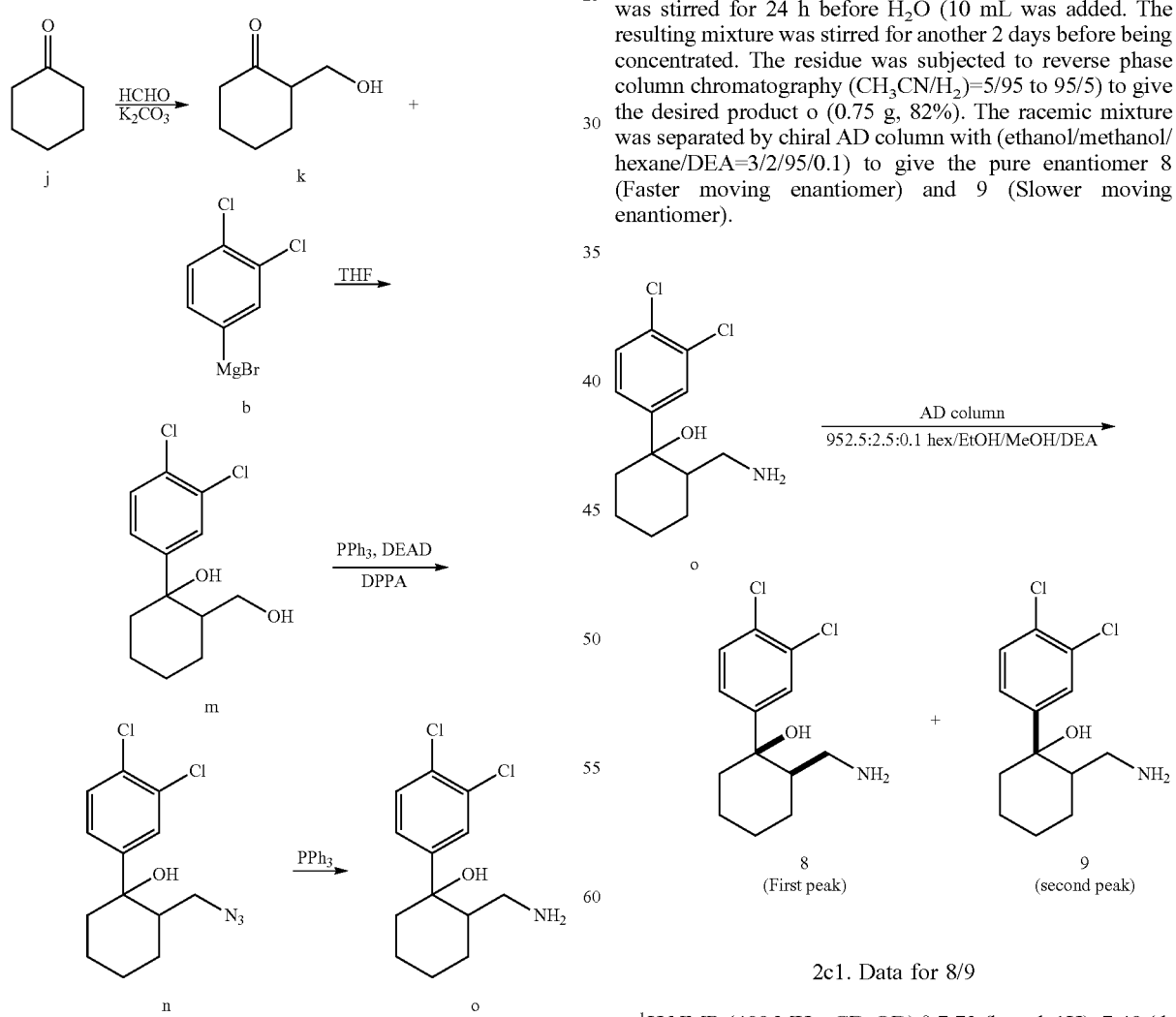

To a solution of cyclohexanone (23.7 g, 25.0 mL, 0.242 mol) in H₂O (50 mL) was added HCHO (37%, 37.5 mL, 0.46 mol) and K₂CO₃ (0.52 g, 3.70 mmol). The reaction mixture was stirred for three hours at 60° C. Then the product was extracted with diethyl ether (2×300 mL). The combined extracts were dried and concentrated. The residue was purified by silica gel column chromatography (ethyl acetate/hexane=1:7 to 1:2) to give k (10.8 g, 33%).

To a solution of k (3.2 g, 25 mmol) in THF (60 mL) at −20° C. was added 3,4-dichlorophenylmagnesium bromide solution (0.5 M, 100 mL, 50 mmol). The reaction mixture was stirred for 30 min before being quenched by NH₄Cl solution (20 ml). The product was then extracted by diethyl ether (2×100 mL). The combined extracts were dried and concentrated. The residue was purified by silica gel column chromatography (hexane/ethyl acetate=1:7 to 1:2) to give m (2.1 g, 31%).

To a solution of m (1.6 g, 5.8 mmol) in THF (40 mL) at r.t. was added PPh₃ (1.8 g, 7.0 mmol), DEAD (1.2 g, 7.0 mmol) and diphenylphosphorazidate (DPPA) (1.9 g, 7.0 mmol). The resulting yellow solution was stirred overnight before being concentrated. The residue was subjected to silica gel column chromatography (hexane/ethyl acetate)=1:10 to 1:1 to give the desired product n (1.32 g, 74%).

To a solution of n (1.00 g, 3.34 mmol) in THF (30 mL) was added PPh₃ (1.75 g, 6.68 mmol). The reaction mixture was stirred for 24 h before H₂O (10 mL was added. The resulting mixture was stirred for another 2 days before being concentrated. The residue was subjected to reverse phase column chromatography (CH₃CN/H₂)=5/95 to 95/5) to give the desired product o (0.75 g, 82%). The racemic mixture was separated by chiral AD column with (ethanol/methanol/hexane/DEA=3/2/95/0.1) to give the pure enantiomer 8 (Faster moving enantiomer) and 9 (Slower moving enantiomer).

2c1. Data for 8/9

$^1$H NMR (400 MHz, CD$_3$OD) δ 7.73 (broad, 1H), 7.40 (d, J=8.4 Hz, 1H), 7.30 (m, 2H), 2.69 (dd, J=2.0, 13.2 Hz, 1H), 2.56 (dd, J=2.8, 13.2 Hz, 1H), 2.20 (m, 2H), 1.80 (m, 2H), 2.28 (m, 2H), 1.60 (m, 2H), 1.50 (m, 3H); $^{13}$C NMR (100 MHz, CD$_3$OD) δ 150.75, 132.38, 130.19, 130.06, 127.64, 124.81, 77.28, 43.63, 43.45, 41.16, 26.38, 25.34, 22.06; ESI MS m/z 274.1, 276.0.
Compound 9 was converted to 2 via reductive amination with formaldehyde.
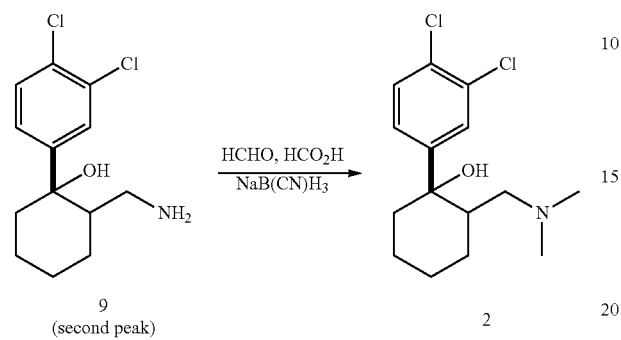
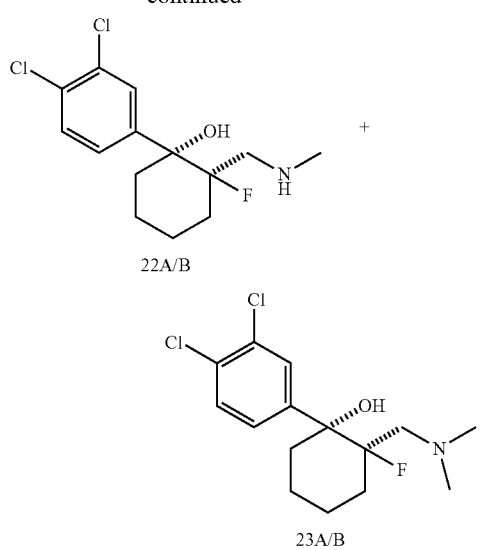
Example 3
3a. Experimental Procedures
Experimental conditions utilized for these syntheses were similar to those employed in Examples 1 and 2.
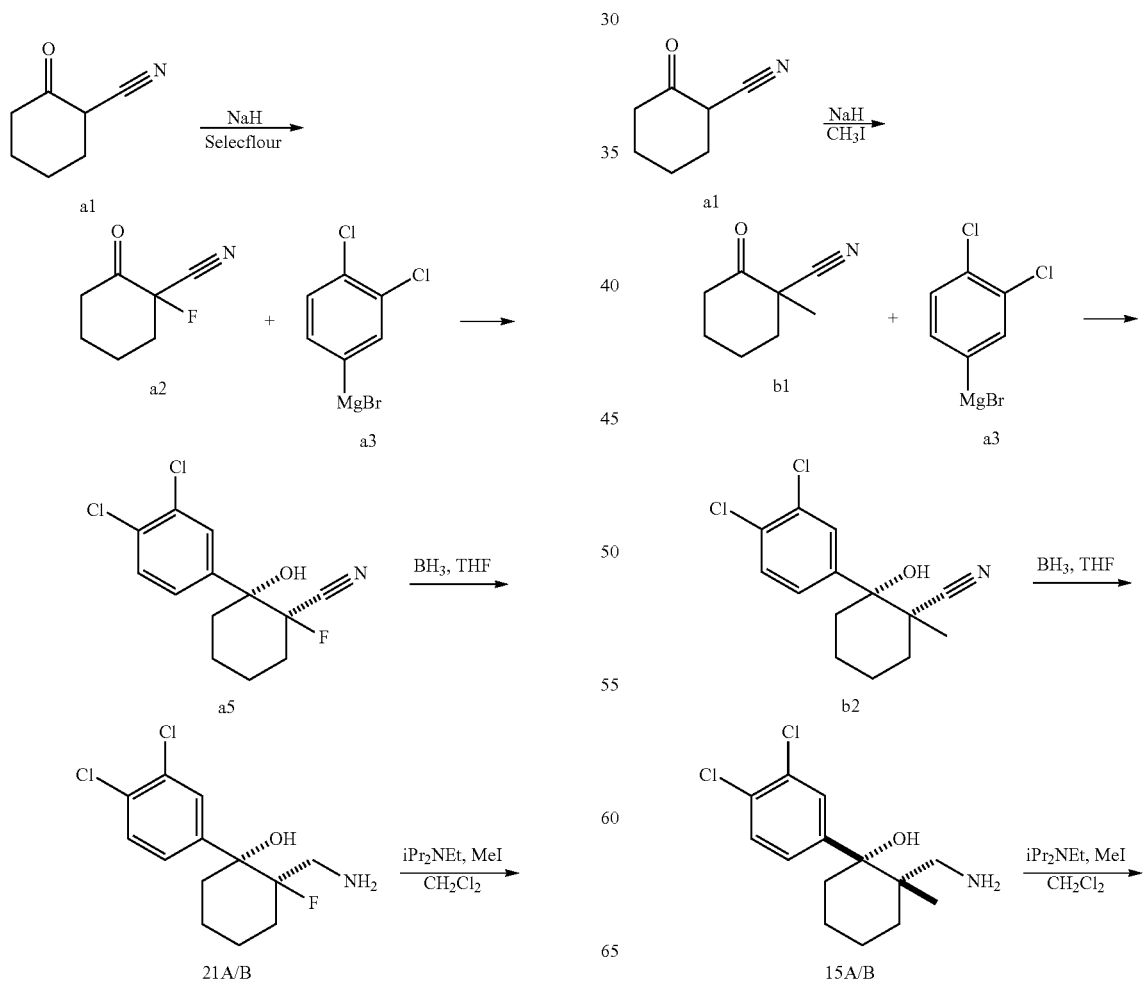

-continued

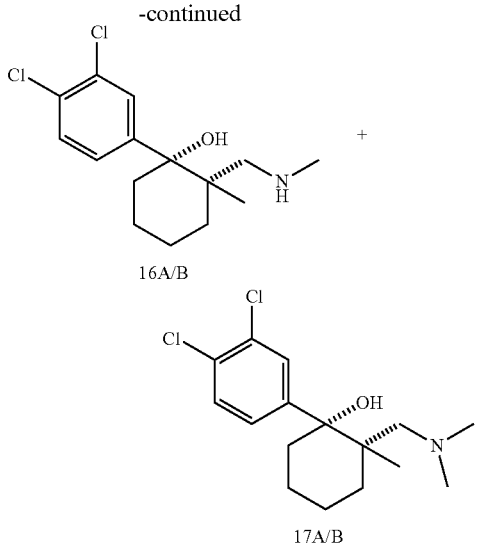

16A/B

17A/B

Experimental conditions utilized for these syntheses were similar to those employed in Examples 1 and 2.

Example 4

4a. In Vitro Human 5-HT/NE/DA Reuptake Inhibition Data

Compounds were tested for their inhibition of functional uptake of serotonin (5-HT), norepinephrine (NE), and dopamine (DA), in synaptosomes prepared from rat whole brain, hypothalamus, or corpus straiatum, respectively, and/or using recombinant human transporters. Details of the assays are described in US 2007/0203111 A1, which is incorporated by reference. Results for functional uptake assay for human reuptake transporters are shown below.

| Corporate ID | 5-HT IC$_{50}$ (nM) | NE IC$_{50}$ (nM) | DA IC$_{50}$ (nM) |
|---|---|---|---|
| 2 | +++ | * | # |
| 4 | ++++ | * | # |
| 9 | ++++ | *** | # |
| 1 | + | ** | ## |
| 8 | +++ | **** | ## |

| 5-HT IC50 | NE IC50 | DA IC50 |
|---|---|---|
| 1-2000 nM (+) | 10-200 nM (*) | 10-200 nM (#) |
| 2001-7000 nM (++) | 201-1000 nM (**) | 201-1000 nM (##) |
| 7001-10000 nM (+++) | 1001-5000 nM (***) | 1001-5000 nM (###) |
| >10001 nM (++++) | >5001 nM (****) | 5001-10000 nM (####) |

4b. In Vitro PK Data (Human Metabolic Stability, Inhibition of CYP450 Enzymes, Inhibition of HERG Current)

| Corporate ID | HLM t$_{1/2}$ (min) | HERG IC$_{50}$ (microM) | CYP inhibition IC$_{50}$ (microM) 5 isoforms (2D6, 2C9, 3A4, 2C19, 1a) |
|---|---|---|---|
| 2 | + | ** | ## |
| 4 | ++ | * | # |
| 1 | + | — | — |

| HLM t½ | HERG IC50 | CYPI IC50 |
|---|---|---|
| 25-175 min (+) | 1-15 μM (*) | >10 μM (#) |
| 176-325 min (++) | 16-30 μM (**) | >20 μM (##) |

4c. Tail Suspension Test, Locomotor Activity Test and Forced Swim Test

4c1. Mouse Tail Suspension Test

The method, which detects antidepressant activity, follows that described by Stéru et al (*Psychopharmacology*, 85: 367-370 (1985)). Rodents, suspended by the tail, rapidly become immobile. Antidepressants decrease the duration of immobility.

The behavior of the animal was recorded automatically for 5 minutes using a computerized device (Med-Associates Inc.) similar to that developed by Stéru et al (*Prog. Neuropsychopharmacol. Exp. Psychiatry* 11: 659-671 (1987)). Ten to twelve mice were tested in each group. Compounds were typically evaluated at 3 doses (1-30 mg/kg), administered orally one time: 30-60 minutes before the test, and compared with a vehicle control group. Desipramine (100 mg/kg), administered under the same experimental conditions, was used as the positive reference substance.

Data were analyzed by one way analysts of variance (ANOVA) followed by post-hoc comparisons where appropriate. An effect was considered significant if p<0.05. Data are represented as the mean and standard error to the mean (s.e.m).

4c2. Locomotor Activity

In order to ensure effects of the compounds on immobility time were not related to a general stimulant effect on baseline motor activity, locomotor activity was assessed using photocell monitored cages (Med-Associates Inc.). Each test chamber was equipped with infrared photocell beams to measure movement of the animals. Horizontal and vertical activity were measured.

Rats or mice were pretreated with vehicle or test compounds and placed back in home cage, following which they were individually placed in locomotor cages and activity was monitored in 1-5 minute intervals for intervals up to 60 min.

Data were analyzed by one way analysis of variance (ANOVA) followed by post-hoc comparisons where appropriate. An effect was considered significant if p<0.05. Data are represented as the mean and standard error to the mean (s.e.m).

4c3. Result Summary

Effects of compounds of the invention were evaluated in the mouse tail suspension and locomotor activity test. Results showed that all compounds tested exhibited an antidepressant-like profile (i.e., significantly decreased immobility time) with MED's in the range of 3-30 mg/kg, PO. At doses active in the tail suspension test, no change or a decrease in baseline motor activity was observed indicating that antidepressant-like activity was not due to a general stimulant effect.

Effects of compounds of the invention were also evaluated in the rat forced swim and locomotor activity tests. All compounds exhibited antidepressant-like effects with MED's in the range of 10-30 mg/kg, PO. The decrease in immobility produced by these compounds appeared to be due to increases in swimming and climbing behaviors indicative of mixed transporter activity (i.e., SNRI profiles). Similar to the mouse tail suspension results, the rat forced swim test also showed anti-depressant like activity for this compound.

| Treatment Dose (mg/kg, PO) | | Mouse Tail Suspension Mean Immobility Time ± S.E.M. | Mouse Locomotor Activity Total Distance Traveled ± S.E.M. |
|---|---|---|---|
| 2 | 0 | +++ | *** |
|   | 0.3 | +++ | ** |
|   | 1 | +++ | ** |
|   | 3 | + | *** |
| 2 | 0 | ++++ | ** |
|   | 3 | +++ | ** |
|   | 10 | + | **** |
|   | 30 | + | * |
| 4 | 1 | ++++ | ** |
|   | 3 | ++++ | ** |
|   | 10 | +++ | *** |
|   | 30 | + | * |

Mouse Tail Suspension
100-160 (+)
161-170 (++)
171-190 (+++)
>191 (++++)

Mouse Locomotor Activity
100-500 (*)
501-700 (**)
701-900 (***)
>901 (****)

After the TST, brain and plasma samples were collected from 4 representative mice from each treatment group for analysis of 2 and 4 exposure levels in these tissues. 2 exhibited a dose-dependent decrease in immobility in this test (see above). Significant levels of the 4 metabolite were found its plasma and brain levels subsequent to oral 2 administration.

4c4. Rat Forced Swim Test

The method, which detects antidepressant activity, followed that described by Porslt et al (*Eur. J. Pharmacol.*, 47: 379-391 (1978)) and modified by Lucki et al. (*Psychopharm.* 121: 66-72 (1995)). Rats forced to swim in a situation from which they cannot escape rapidly become immobile. Antidepressants decrease the duration of immobility. In addition, distinct patterns of active behaviors are produced by antidepressants that selectively inhibit norepinephrine (NE) and serotonin (5-HT) uptake in this test. Selective NE reuptake inhibitors decrease immobility by increasing climbing behaviors whereas selective 5-HT reuptake inhibitors decrease immobility by increasing swimming behaviors.

Rats were individually placed in a cylinder (Height=40 cm; Diameter=20 cm) containing 22 cm water (25° C.) for 15 minutes on the first day of the experiment (Session 1) and were then put back in the water 24 hours later for a 5 minute test (Session 2). The sessions were videotaped and duration of immobility as well as swimming and climbing behaviors during the 5 minute test were measured. Twelve rats were tested in each group. The test was performed blind. Compounds were typically evaluated at 3 doses (1-30 mg/kg), administered orally 2 times: 24 hours and 30-60 minutes before the test (Session 2), and compared with a vehicle control group. Desipramine (20 mg/kg i.p.), administered under the same experimental conditions, was used as the positive reference substance.

Data were analyzed by one way analysis of variance (ANOVA) followed by post-hoc comparisons where appropriate. An effect will be considered significant if $p<0.05$. Data are represented as the mean and standard error to the mean (s.e.m.).

| Treatment Dose (mg/kg, PO) | | Rat Forced Swim (Means ± S.E.M.) | | | Rat Locomotor Activity Total Distance Traveled ± S.E.M. |
|---|---|---|---|---|---|
| | | Immobility | Swimming | Climbing | |
| 2 | 0 | +++ | * | # | ° |
|   | 1 | +++ | * | ## | ° |
|   | 3 | +++ | * | # | ° |
|   | 10 | + | ** | ### | °°° |

Immobility            Swimming         Climbing         Total Distance Traveled
1-20 (+)              1-5 (*)          1-10 (#)         100-2500 (°)
21-40 (++)            6-9 (**)         11-20 (##)       2501-5000 (°°)
>41 (+++)             >10 (***)        >21 (###)        >5001 (°°°)

Example 5

5a. Ex Vivo Binding Assay

Receptor occupancy of central noradrenaline (NA), 5-HT and dopamine (DA) transporter sites following peripheral administration of compounds was determined using [$^3$H] nisoxetine, [$^3$H] citalopram and [$^3$H] WIN 35428 binding, respectively. Liquid scintillation counting was used to quantify the radioactivity.

C57BL/6 mice (25-30 g) were dosed orally with either vehicle or compound at 4 dose levels. Mice were sacrificed 60 minutes after treatment. Whole brains were removed and cortex and striata dissected out before being frozen on dry ice. The brain tissue was stored at −20° C. until the day of the assay. The cortex from each hemisphere was frozen separately. One was used to determine occupancy of NA transporter sites and the other occupancy of 5-HT transporter sites. Striatum was used to determine occupancy of DA transporter sites.

Frontal cortex from each hemisphere or striata was homogenized individually in ice-cold assay buffer using a tight fitting glass/Teflon homogenizer and used immediately in the binding assay.

5b. [$^3$H] Citalopram Binding to 5-HT Transporter (SERT) Sites in Mouse Brain

Cortical membranes (400 μL; equivalent to 1.25 mg wet weight of tissue/tube) were incubated with 50 μl of [$^3$H] citalopram at a single concentration of 1.3 nM and either 50 μl of buffer (total binding) or 50 μl of paroxetine (0.5 μM; non-specific binding) for 1 h at 27° C. For each animal, three tubes were used for the determination of total binding and three tubes were used for the determination of non-specific binding.

5c. [$^3$H] Nisoxetine Binding to Norepinephrine Transporter (NET) Sites in Mouse Brain Cortical membranes (400 μL; equivalent to 6.0 mg wet weight of tissue/tube) were incubated with 50 μL of [$^3$H] nisoxetine at a single concentration of 0.6 nM and either 50 μL of buffer (total binding) or 50 μL of mazindol (1 μM; non-specific binding) for 4 h at 4° C. For each animal, three tubes were used for the determination of total binding and three tubes were used for the determination of non-specific binding.

5d. [$^3$H] WIN 35428 Binding to DA Transporter (DAT) Sites in Mouse Brain

Striatal membranes (200 μL; equivalent to 2 mg wet weight of tissue/tube) were incubated with 25 μL of [$^3$H] WIN 35428 at a single concentration of 24 nM and either 25 μL of buffer (total binding) or 25 μL of GBR12935 (1 μM; non-specific binding) for 2 h at 4° C. For each animal, two tubes were used for the determination of total binding and two tubes for the determination of non-specific binding.

Membrane bound radioactivity was recovered by filtration under vacuum through Skatron 11731 filters, presoaked in 0.5% PEI, using a Skatron cell harvester. Filters were rapidly washed with ice-cold phosphate buffer and radioactivity (dpm) was determined by liquid scintillation counting (1 mL Packard MV Gold scintillator).

5e. Data Analysis

A value for specific binding (dpm) was generated by the subtraction of mean non-specific binding (dpm) from mean total binding (dpm) for each animal. Data are presented as mean specific binding (dpm) and as a percentage of the vehicle-treated control taken as 100%.

5f. Results Summary

Ex vivo SERT, NET and DAT binding/receptor occupancy data were generated for 2.

Ex Vivo Binding Profile of 2 in Mice

| Treatment Dose (mg/kg, PO) | Mean Specific Binding (dpm) ± S.E.M. (Values in Brackets Denote % Transporter Occupancy) | | |
|---|---|---|---|
| | NET | SERT | DAT |
| 2    0 | 1050 ± 34 | 3302 ± 111 | 43327 ± 4273 |
| 1 | 845 ± 44 (19)* | 2926 ± 119 (11) | 36886 ± 1873 (15) |
| 3 | 583 ± 20 (44)* | 3330 ± 176 (−1) | 21744 ± 1050 (50)* |
| 10 | 271 ± 12 (74)* | 3104 ± 131 (6) | 8941 ± 305 (79)* |
| 30 | 115 ± 13 (89)* | 3126 ± 204 (5) | 4236 ± 538 (90)* |

Example 6

Summary of selected in vitro data for test compounds

| | 5-HT IC50 nM | NE IC50 nM | DA IC50 nM |
|---|---|---|---|
| 1 | + | ** | ## |
| 2 | + | * | # |
| 4 | ++++ | * | # |
| 7 | ++ | ** | # |
| 8 | +++ | **** | ## |
| 9 | ++++ | *** | # |
| 10 | ++ | ** | # |
| 11 | + | ** | # |
| 12 A/B | +++ | **** | ### |
| 13 A/B | n.t | n.t | n.t |
| 14 A/B | ++ | **** | ## |
| 15 A/B | ++ | **** | ## |
| 16 A/B | + | **** | # |
| 17 A/B | ++ | **** | ## |
| 18 A/B | +++ | *** | # |
| 19 A/B | n.t. | n.t | n.t |
| 20 A/B | n.t. | n.t | n.t |
| 21 A/B | + | **** | # |
| 22 A/B | n.t. | n.t | n.t |
| 23 A/B | ++ | **** | ## |
| 24 | +++ | **** | #### |
| 25 | ++++ | * | # |
| 26 | + | *** | #### |
| 27 | ++ | * | ## |

5-HT IC50: 1-2000 nM (+), 2001-7000 nM (++), 7001-10000 nM (+++), >10001 nM (++++)
NE IC50: 10-200 nM (*), 201-1000 nM (), 1001-5000 nM (*), >5001 nM (****)
DA IC50: 10-200 nM (#), 201-1000 nM (##), 1001-5000 nM (###), 5001-10000 nM (####)
Human Liver Microsome = HLM; Rat Liver Microsome = RLM; Mouse Liver Microsome = MLM.

Example 7

7a. Reserpine Rat Model

The effects of compound 4 alone and in combination with L-DOPA were evaluated in the reserpine-treated rat Parkinson's disease model. The method, which detects antiparkinson activity (reversal of motor deficits and akinesia), follows that described by Johnston et al. (Exp Neurol. 101, 243-250, 2005). Eighteen hours prior to behavioural testing, rats were lightly anaesthetized with isoflurane and reserpine (3 mg/kg, sc) was injected along with saline (50 ml/kg) to prevent dehydration.

7b. Behavioral Assessment

Accelerating Rotarod: Performance on an accelerating rotarod was assessed using a 4-station rat rotarod (MedAssociates, USA). The speed of rotation of the rotarod was increased from 3.5 to 35 rpm over 5 minutes and the time for which the animal remained on the rod determined as the mean of three trials.

Catalepsy Test: Catalepsy was assessed by placing the rat's forepaws on top of a horizontal wooden rod suspended 6 cm above the bench surface. Time taken to remove both paws from the rod was recorded, up to a maximum of 120 seconds. Three trials per animal were conducted.

Open Field: Activity in an open field arena was assessed using automated activity monitors (Linton Instrumentation, UK). Rats were placed in the activity boxes and locomotor activity was recorded over a 240 minute period.

Drug Administration: For the monotherapy experiment, the effects of 5 different treatments were assessed: 1) vehicle (sterile water, PO), 2) 3 mg/kg compound 4 (PO), 3) 10 mg/kg compound 4 (PO), 4) 30 mg/kg compound 4 and 5) 80 mg/kg (IP) of the positive reference substance, L-DOPA (80 mg/kg). In the combination experiment, 5 different treatments were assessed: 1) compound 4 vehicle (PO)+L-DOPA vehicle (IP), 2) compound 4 (10 mg/kg, PO)+L-DOPA vehicle (IP), 3) compound 4 vehicle (PO)+L-DOPA (30 mg/kg, IP), 4) compound 4 (10 mg/kg, PO)+L-DOPA (30 mg/kg, IP) and 5) compound 4 vehicle (PO)+L-DOPA (80 mg/kg, IP). Treatments were given in a randomized fashion and each animal received all treatment conditions. Compound 4 was administered 60 minutes prior to behavioral assessment and L-DOPA was administered immediately prior to behavioral testing.

Figure 2:
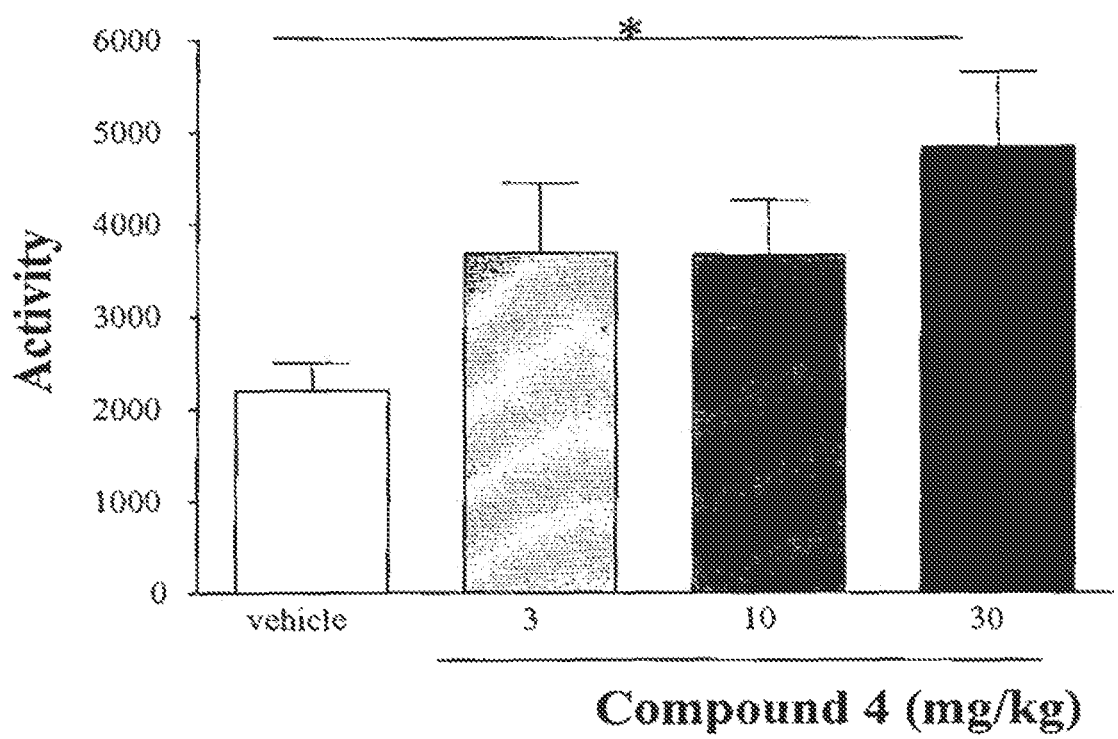
FIG. 2 is a graph showing effect of compound 4 on baseline locomotor activity in the reserpinized rat.
Figure 3:
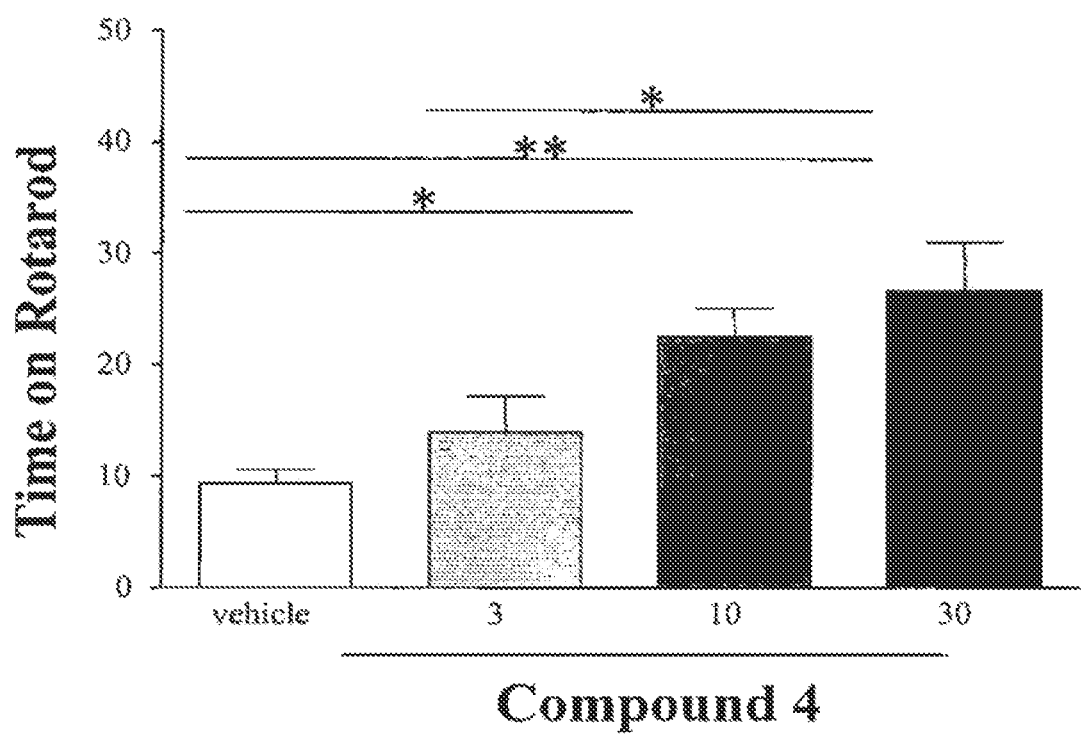
FIG. 3 is a graph showing effect of compound 4 on rotarod performance in the reserpinized rat.
Figure 4:
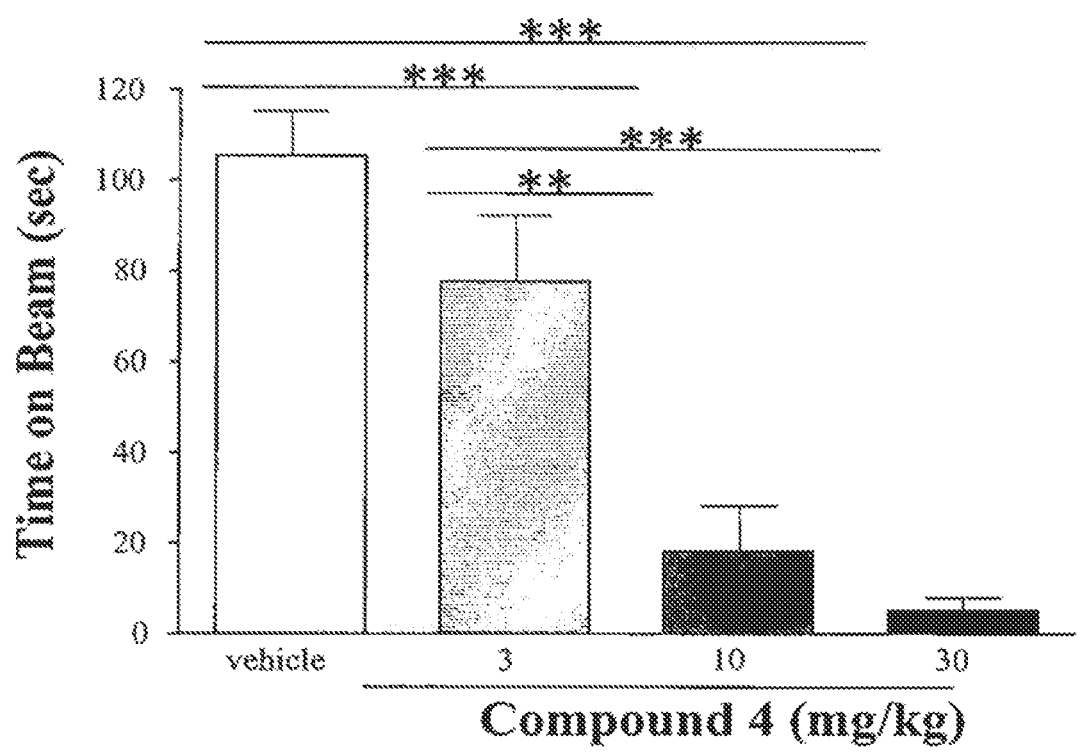
FIG. 4 is a graph showing effect of compound 4 on catalepsy in the reserpinized rat.
Figure 5:
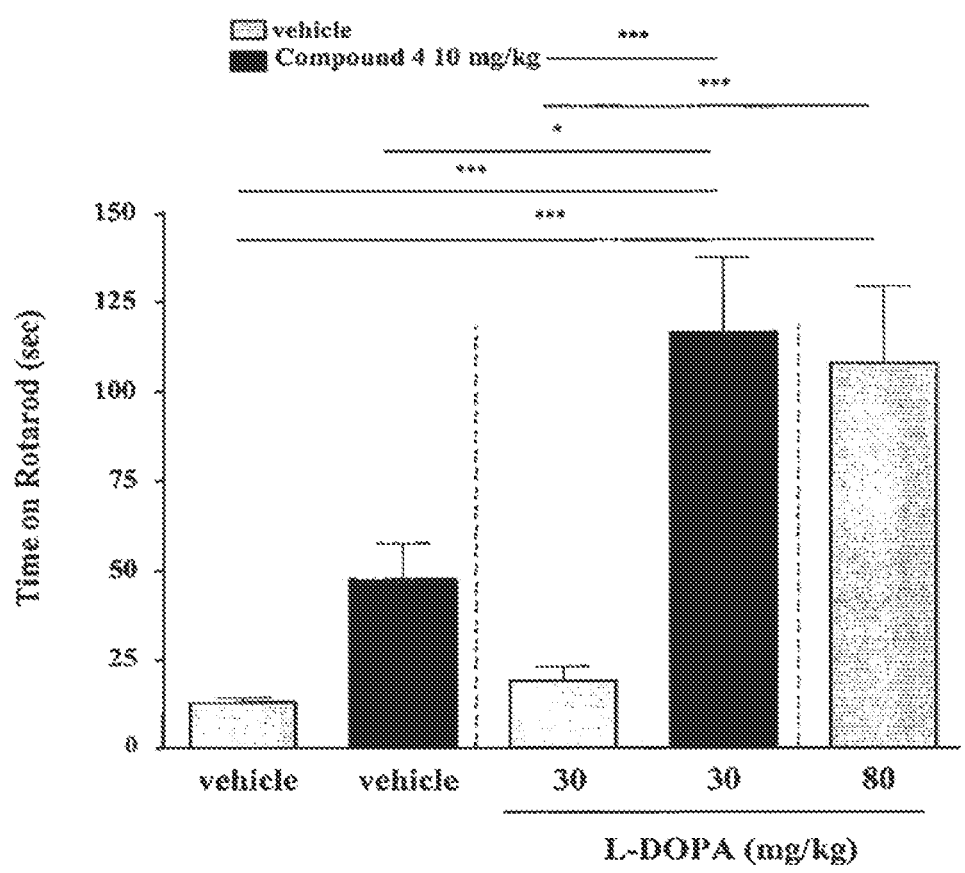
FIG. 5 is a graph showing combined compound 4 and low dose L-DOPA rotarod performance as compared to high dose L-DOPA.

Results showed that compound 4 (3-30 mg/kg, PO) alone dose-dependently improved performance in a variety of behavioral tests (baseline locomotor activity, FIG. 2, rotarod, FIG. 3, and catalepsy, FIG. 4). Depending upon the behavioral test, effects of compound 4 were similar or smaller than those observed with L-DOPA (80 mg/kg). In the coordination experiment, the combination of compound 4 (10 mg/kg, PO) and low dose L-DOPA (30 mg/kg) showed effects that were equal in magnitude and of longer duration than those provided by a higher dose L-DOPA dose (80 mg/kg), FIG. 5.

The data suggest that compound 4 may have some anti-parkinsonian actions as monotherapy although effects are not as powerful as L-DOPA. The combination compound 4 and low dose L-DOPA experiments indicated anti-parkinsonian actions that were equal in magnitude and of longer duration than those provided by a higher L-DOPA dose. Compound 4 could thus be described as "L-DOPA sparing".

Example 8

8a. Rat Unilateral 6-Hydroxydopamine (6-OHDA) Lesion Model

The effects of compound 4 alone and in combination with L-DOPA were evaluated in the rodent 6-OHDA-lesioned rat Parkinson's disease model. The method, which detects anti-parkinson activity (reversal of motor deficits and akinesia), follows that described by Henry et al. (Exp Neurol, 151(2): 334-42, 1998).

Animal Preparation: Prior to surgery, rats were administered pargyline (5 mg/kg, ip) and desipramine (25 mg/kg ip) to optimize subsequent 6-OHDA availability and increase specificity for toxicity to dopaminergic neurons. Rats were then anesthetized with isoflurane and placed in a stereotaxic frame. After exposure of Bregma, a burr hole was drilled in the skull above the right median forebrain bundle at co-ordinates: 2.8 mm posterior and 2 mm lateral to Bregma (according to the atlas of Paxinos and Watson, 1986). A 28 G Hamilton needle was then lowered 9 mm below the skull. Injection of 6-OHDA (12.5 μg in 2.5 μl) was then made (1 μl/min). The needle was then left in place for 4 minutes to ensure complete absorption of the solution. After slow retraction of the injection needle, the wound was closed and animals were administered saline (50 ml/kg, sc), an analgesic (Ketoprofen, 0.5 mg/kg) and a broad spectrum antibiotic (enrofloxacin, 75 mg/kg). Following surgery, animals were left untreated for 3 weeks to allow the lesion to develop and stabilize prior to the start of behavioral assessment.

8b. Behavioral Assessment

Paw Placing Test: The paw placing test assesses correct placing of each forepaw in response to a sensory stimulus. Rats were gently held by their torsos and each forepaw was restrained between thumb and forefinger whilst allowing the opposite paw to hang free. The rat was then held parallel to the edge of a table with the free forelimb placed adjacent to the edge. The animal was then moved towards the table and the vibrissae brushed against the table edge to elicit a forelimb placing response from the free limb. A total of ten trials were conducted in quick succession before repeating the procedure for the other paw. The test was quantified as the percentage of successful placing responses of the limb contralateral to the side of the 6-OHDA lesion. Placement of the limb ipsilateral to the side of the lesion was successful in 100% of cases in all animals.

Drug Administration: For the monotherapy experiment, the effects of 5 different treatments were assessed: 1) vehicle (sterile water, PO), 2) 3 mg/kg compound 4 (PO), 3) 10 mg/kg compound 4 (PO), 4) 30 mg/kg compound 4 and 5) 6.5 mg/kg (IP) of the positive reference substance, L-DOPA. In the combination experiment, 5 different treatments were assessed: 1) compound 4 vehicle (PO)+L-DOPA vehicle (IP), 2) compound 4 (10 mg/kg, PO)+L-DOPA vehicle (IP), 3) compound 4 vehicle (PO)+L-DOPA (2 mg/kg, IP), 4) compound 4 (10 mg/kg, PO)+L-DOPA (2 mg/kg, IP) and 5) compound 4 vehicle (PO)+L-DOPA (6.5 mg/kg, IP). Treatments were given in a randomized fashion and each animal received each treatment condition. Compound 4 was administered 60 minutes prior to behavioral assessment and L-DOPA was administered immediately prior to behavioral testing.

Figure 6:
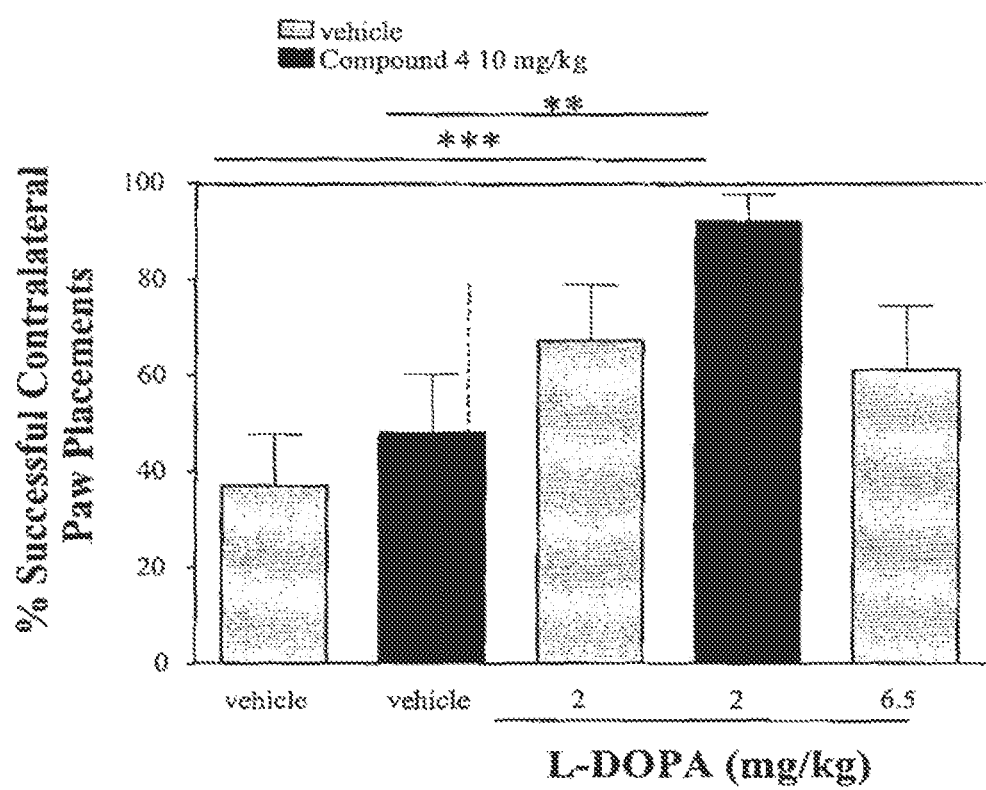
FIG. 6 is a graph showing the effect of combination of L-DOPA and compound 4 in the 6-OHDA lesioned rat.

Results showed that compound 4 (3-30 mg/kg, PO) alone produced little or no improvement in performance in the paw placement task. The combination of compound 4 (10 mg/kg, PO) and low dose L-DOPA significantly increased paw placement performance providing some evidence of synergy between actions of compound 4 and L-DOPA (FIG. 6).

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

All patents, patent applications, and other publications cited in this application are incorporated by reference herein in their entirely for all purposes.

What is claimed is:
1. A compound of Formula (Ia) or (Ib):

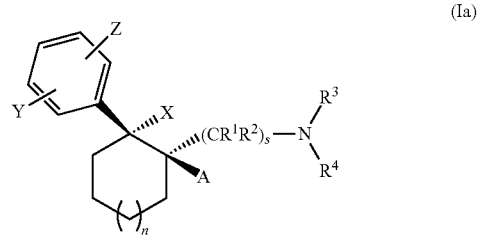

(Ia)

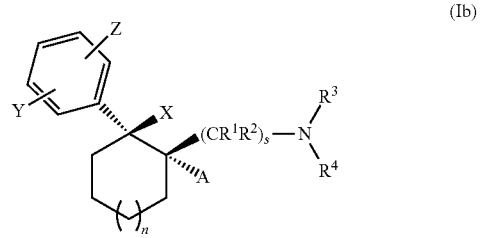

(Ib)

or a pharmaceutically acceptable salt thereof, wherein n is 1;

s is 1;

A is H, substituted or unsubstituted alkyl, halogen or substituted or unsubstituted haloalkyl;

X is H, halogen, substituted or unsubstituted alkyl, substituted or unsubstituted aryl, substituted or unsubstituted haloalkyl, or $OR^5$;

Y and Z are each independently halogen;

$R^1$ and $R^2$ are each independently H, halogen, CN, CF3, $OR^6$, substituted or unsubstituted alkyl, substituted or unsubstituted heteroalkyl, substituted or unsubstituted aryl, substituted or unsubstituted heteroaryl, or substituted or unsubstituted heterocycloalkyl;

$R^3$ and $R^4$ are each independently H, $OR^7$, acyl, $S(O)2R^8$, substituted or unsubstituted alkyl, substituted or unsubstituted heteroalkyl, substituted or unsubstituted aryl, substituted or unsubstituted heteroaryl, or substituted or unsubstituted heterocycloalkyl;

$R^5$ is H, substituted or unsubstituted alkyl, substituted or unsubstituted heteroalkyl, Substituted or unsubstituted aryl, substituted or unsubstituted heteroaryl, acyl, or $S(O)2R^{5a}$;

$R^{5a}$ is substituted or unsubstituted alkyl, substituted or unsubstituted heteroalkyl, substituted or unsubstituted aryl, substituted or unsubstituted heteroaryl, or substituted or unsubstituted heterocycloalkyl;

$R^6$ is H, substituted or unsubstituted alkyl, substituted or unsubstituted heteroalkyl, substituted or unsubstituted aryl, substituted or unsubstituted heteroaryl, or substituted or unsubstituted heterocycloalkyl;

$R^7$ is H, substituted or unsubstituted alkyl, substituted or unsubstituted heteroalkyl, substituted or unsubstituted aryl, substituted or unsubstituted heteroaryl, or substituted or unsubstituted heterocycloalkyl; and $R^8$ is substituted or unsubstituted alkyl, substituted or unsubstituted heteroalkyl, substituted or unsubstituted aryl, substituted or unsubstituted heteroaryl, or substituted or unsubstituted heterocycloalkyl.

2. The compound of claim 1, or a pharmaceutically acceptable salt thereof, wherein one of $R^3$ and $R^4$ is H and the other is substituted or unsubstituted $C_1$-$C_4$ alkyl.

3. The compound of claim 2, or a pharmaceutically acceptable salt thereof, wherein one of $R^3$ and $R^4$ is H and the other is $CH_3$.

4. The compound of claim 1, or a pharmaceutically acceptable salt thereof, wherein $R^3$ and $R^4$ are each H.

5. The compound of claim 1, or a pharmaceutically acceptable salt thereof, wherein $R^3$ and $R^4$ are each independently substituted or unsubstituted $C_1$-$C_4$ alkyl.

6. The compound of claim 5, or a pharmaceutically acceptable salt thereof, wherein $R^3$ and $R^4$ are each $CH_3$.

7. The compound of claim 1, or a pharmaceutically acceptable salt thereof, wherein $R^1$ and $R^2$ are each H.

8. The compound of claim 1, or a pharmaceutically acceptable salt thereof, wherein X is H, halogen, substituted or unsubstituted alkyl, or $OR^5$.

9. The compound of claim 8, or a pharmaceutically acceptable salt thereof, wherein X is H, halogen, OH or methoxy.

10. The compound of claim 9, or a pharmaceutically acceptable salt thereof, wherein X is OH.

11. The compound of claim 1, or a pharmaceutically acceptable salt thereof, wherein A is H, methyl or halogen.

12. The compound of claim 11, or a pharmaceutically acceptable salt thereof, wherein A is H.

13. The compound of claim 1, having a structure of Formula (IIb), (IIc), (IId), or (IIe), or a pharmaceutically acceptable salt thereof:

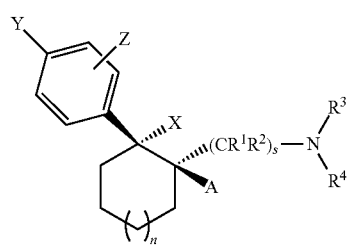
(IIb)

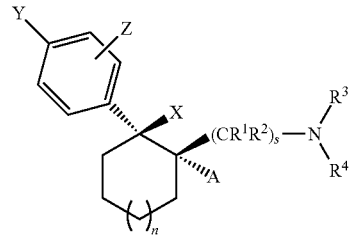
(IIc)

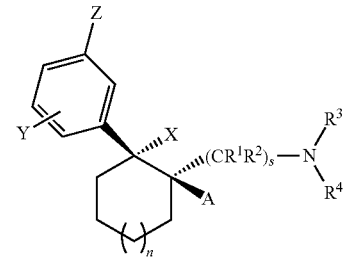
(IId)

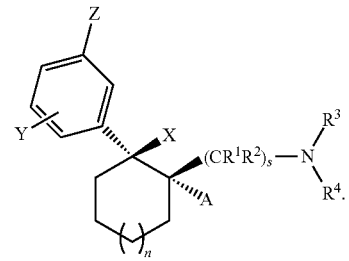
(IIe)

14. The compound of claim 1, having a structure of Formula (IVa) or (IVb), or a pharmaceutically acceptable salt thereof:

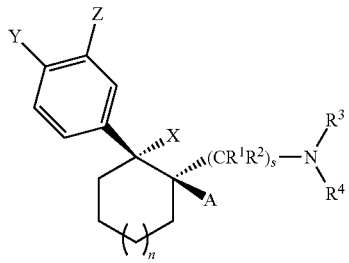
(IVa)

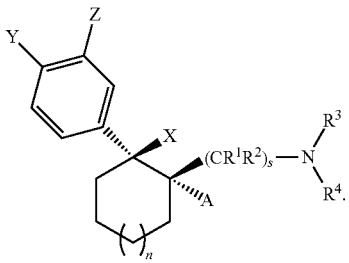
(IVb)

15. The compound of claim 14, wherein $R^1$ and $R^2$ are each H.

16. The compound of claim 15, wherein A is H, fluoro, or $CH_3$.

17. The compound of claim 16, wherein A is H.

18. The compound of claim 15, or a pharmaceutically acceptable salt thereof, wherein Y and Z are each independently chloro or fluoro.

19. The compound of claim 18, or a pharmaceutically acceptable salt thereof, wherein Y and Z are both chloro.

20. The compound of claim 19, wherein X is OH or methoxy.

21. The compound of claim 20, wherein X is OH.

22. The compound of claim 21, wherein $R^3$ and $R^4$ are each independently H or unsubstituted $C_1$-$C_4$ alkyl.

23. The compound of claim 1, having a structure of Formula (Ve) or (Vf), or a pharmaceutically acceptable salt thereof:

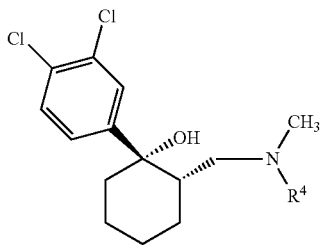

(Ve)

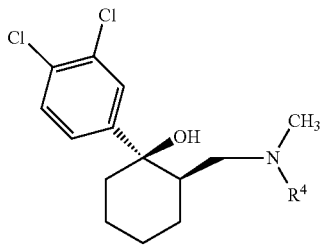

(Vf)

wherein $R^4$ is H or $CH_3$.

24. The compound of claim 23, or a pharmaceutically acceptable salt thereof, wherein $R^4$ is H.

25. The compound of claim 23, or a pharmaceutically acceptable salt thereof, wherein $R^4$ is $CH_3$.

26. A pharmaceutical formulation comprising a compound of claim 23, or a pharmaceutically acceptable salt thereof, in combination with a pharmaceutically acceptable excipient.

27. A pharmaceutical formulation comprising a compound of claim 1, or a pharmaceutically acceptable salt thereof, in combination with a pharmaceutically acceptable excipient.

* * * * *